United States Patent [19]

Kupke et al.

[11] Patent Number: 5,962,253
[45] Date of Patent: Oct. 5, 1999

[54] OXIDATIVE DECARBOXYLATION OF PEPTIDES CATALYZED BY FLAVOPROTEIN EPID

[75] Inventors: Thomas Kupke; Friedrich Götz; Christoph Kempter; Günther Jung, all of Tübingen, Germany

[73] Assignee: Boehringer Ingelheim International GmbH, Ingelheim am Rhein, Germany

[21] Appl. No.: 08/645,193

[22] Filed: May 13, 1996

[51] Int. Cl.[6] ............................. C12P 33/20; C12P 21/06; C12N 9/04; C12N 1/20

[52] U.S. Cl. ......................... 435/53; 435/68.1; 435/189; 435/190; 435/252.3

[58] Field of Search ................................. 435/189, 190, 435/252.3, 53, 68.1

[56] References Cited

U.S. PATENT DOCUMENTS

| 4,716,115 | 12/1987 | Gonzalez et al. | 435/172.3 |
| 5,231,013 | 7/1993 | Jung et al. | 435/71.3 |

FOREIGN PATENT DOCUMENTS

0 342 658 A1  11/1989  European Pat. Off. .

OTHER PUBLICATIONS

Kupke et al. (1994) J.Biol.Chem. 269, 5653–5659.
Kupke et al. (1995) J.Biol.Chem. 270, 11282–11289.
Allgaier, H. et al., "Epidermin: sequencing of a heterodet tetracyclic 21–peptide amide antibiotic," *Eur. J. Biochem.* 160:9–22 (1986).
Augustin, J. et al., "Identification of epidermin biosynthetic genes by complementation studies and heterologous expression," *Proc. 1st Intl. Workshop Lantibiotics. Nisin Nov. Lantibiotics*:277–286 (1991).
Augustin, J. et al., "Genetic analysis of epidermin biosynthetic genes and epidermin–negative mutants of *Staphylococcus epidermidis*," *Eur. J. Biochem.* 204:1149–1154 (1992).
Banerjee, S. and J.N. Hansen, "Structure and Expression of a Gene Encoding the Precursor of Subtilin, a Small Protein Antibiotic," *J. Biol. Chem.* 263(19):9508–9514 (1988).
Buchman, G.W. et al., "Structure, Expression, and Evolution of a Gene Encoding the Precursor of Nisin, a Small Protein Antibiotic," *J. Biol. Chem.* 263(31):16260–16266 (1988).
Entian, K.–D. et al., "Structure and DNA–sequence analysis of the staphylococcal lantibiotics epidermin and gallidermin," *Abstr. Ann. Meeting Am. Soc. Microbiol.* 89:182 abstr. H–78 (1989).
Fiedler, H.–P. et al., "Purification of the Hydrophilic Antibiotics Epidermin, Gallidermin and Nikkomycin Z Preparative Reversed–Phase HPLC," *Chromato.* 26:215–220 (1988).
Fiedler, H.–P. et al., "Purification of the hydrophilic antibiotics epidermin, gallidermin, and nikkomycin Z by preparative reversed–phase HPLC," *Chem. Abstr.* 110:583 abstr. 210845v (1989).

Gennaro, M.L. et al., "A Site–Specific Recombination Function in *Staphylococcus aureus* Plasmids," *J. Bacteriol.* 169(6):2601–2610 (1987).
Götz, F. et al., "Genetic and Biochemical Studies On The Biosynthesis Of Epidermin, An Antibiotic Peptide From Staphylococci," *Med. Microbiol. Immunol.* 182(4):188 abstr. 24 (1993).
Horinuchi, S. and B. Weisblum, "Nucleotide Sequence and Functional Map of pC194, a Plasmid That Specifies Inducible Chloramphenicol Resistance," *J. Bacteriol.* 150(2):815–825 (1982).
Jung, G., "Lantibiotics—Ribosomally Synthesized Biologically Active Polypeptides containing Sulfide Bridges and α,β–Didehydroamino Acids," *Angew. Chem. Int. Ed. Engl.* 30:1051–1068 (1991).
Kaletta, C. and K.–D. Entian, "Nisin, a Peptide Antibiotic: Cloning and Sequencing of the nisA Gene and Posttranslational Processing of Its Peptide Product," *J. Bacteriol.* 171(3):1597–1601 (1989).
Kaletta, C. et al., "Cloning of genes coding for Polypeptide antibiotics (Lantibiotics) and posttranslational processing of their peptide products," *DECHEMA Biotech. Conf.* 3(*part A*):233–235 (1989).
Kaletta, C. et al., "Pep5, a new lantibiotic: structural gene isolation and prepeptide sequence," *Arch. Microbiol.* 152:16–19 (1989).
Kellner, R. et al., "Gallidermin: a new lanthionine–containing polypeptide antibiotic," *Eur. J. Biochem.* 177:53–59 (1988).
Kellner, R. et al., "Gallidermin: a new lanthionine–containing polypeptide antibiotic," *Chem. Abstr.* 110:4245 abstr. 4243u (1989).
Khan, S.A. and R.P. Novick, "Complete Nucleotide Sequence of pT181, a Tetracycline–Resistance Plasmid from *Staphylococcus aureus*," *Plasmid* 10:251–259 (1983).
Klein, C. et al., "Analysis of Genes Involved in Biosynthesis of the Lantibiotic Subtilin," *Appl. Env. Microbiol.* 58(1):132–142 (1992).
Koide, Y. et al., "Cloning and Sequencing of the Major Intracellular Serine Protease Gene of *Bacillus subtilis*," *J. Bacteriol.* 167(1):110–116 (1986).
Kupke, T. et al., "Purification and Characterization of EpiD, a Flavoprotein Involved in the Biosynthesis of the Lantibiotic Epidermin," *J. Bacteriol.* 174(16):5354–5361 (1992).

(List continued on next page.)

*Primary Examiner*—Robert A. Wax
*Assistant Examiner*—Elizabeth Slobodyansky
*Attorney, Agent, or Firm*—Sterne, Kessler, Goldstein & Fox P.L.L.C.

[57] ABSTRACT

A method is described for oxidatively decarboxylating a peptide, comprising combining a peptide with EpiD, wherein the peptide comprises at its carboxy terminus the amino acid sequence $X_1X_2X_3X_4X_5X_6C$, wherein $X_1$, $X_2$, $X_3$ and $X_4$ are any one of the twenty common amino acids, $X_5$ is Tyr, Val, Met, Leu, Ile, Phe or Trp, and $X_6$ is Cys, Ala, Ser, Val, or Thr, whereby the oxidative decarboxylation of the peptide occurs.

13 Claims, 42 Drawing Sheets

OTHER PUBLICATIONS

Kupke, T. et al., "Purification and characterization of EpiA, the peptide substrate for post–translational modifications involved in epidermin biosynthesis," *FEMS Microbiol. Lett.* *112*:43–48 (1993).

Kupke, T. et al., "Mass Spectroscopic Analysis of a Novel Enzymatic Reaction," *J. Biol. Chem.* *269*(8):5653–5659 (1994).

Kupke, T. et al., "Characterization of the Flavoprotein EpiD (EpiD II)," 2nd International Workshop on Lantibiotics (1994).

Kupke, T. et al., "Oxidative Decarboxylierung von Peptiden," Presented at the 2nd Deutsches Peptidkolloquium, Tübingen (Mar. 1995).

Kupke, T. et al., "Oxidative Decarboxylation of Peptides Catalyzed by Flavoprotein EpiD," *J. Biol. Chem.* *270*(19):11282–11289 (May 1995).

Kupke, T. et al., "Oxidative Decarboxylation Of Peptides Catalyzed By Flavoprotein EpiD: Determination Of Substrate Specificity Using Peptide Libraries And Neutral Loss Mass Spectrometry," Presented at the 28th Diskussionstagung der Arbeitsgemeinschaft Massenspektrometrie, Tübingen (Jun. 1995).

Kupke, T. and F. Götz, "Characterization of enzymes EpiC, and EpiP involved in biosynthesis of lantibiotic epidermin," Presented at the Gordon Conference: Staphylococcal diseases, Irse, Germany (Oct. 1995).

Schnell, N. et al., "Prepeptide sequence of epidermin, a ribosomally synthesized antibiotic with four sulphide–rings," *Nature* *333*:276–278 (1988).

Schnell, N. et al., "Prepeptide sequence of epidermin, a ribosomally synthesized antibiotic with four sulfide–rings," *Chem. Abstr.* *109*:288 abstr. 144800c (1988).

Schnell, N. et al., "Structural gene isolation and prepeptide sequence of gallidermin, a new lantionine containing antibiotic," *FEMS Microbiol. Lett.* *58*:263–268 (1989).

Schnell, N. et al., "The operon–like organisation of lantibiotic epidermin biosynthesis genes," *Proc. 1st Intl. Workshop Lantibiotics. Nisin Nov. Lantibiotics*:269:276 (1991).

Schnell, N. et al., "Analysis of genes involved in the biosynthesis of lantibiotic epidermin," *Eur. J. Biochem.* *204*(1):57–68 (1992).

Shiba, T. and T. Wakamiya, "Lanthionine Peptide," *Kagaku* *40*(6):416–417 (1985) (with English language translation).

Shiba, T. and T. Wakamiya, "Lanthionine Peptide," *Chem. Abstr.* *104*:206 abstr. 2246z (1986).

Vieira, J. and J. Messing, "The pUC plasmids, an M13mp7–derived system for insertion mutagenesis and sequencing with synthetic universal primers," *Gene* *19*:259–268 (1982).

Yanisch–Perron, C. et al., "Improved M13 phage cloning vectors and host strains: nucleotide sequences of the M13mp18 and pUC19 vectors," *Gene* *33*:103–119 (1985).

TTTAAACTTTATATCATTAATAATGTTTAGGAAAAGTAGAAGAAAAATTACACTTTTGTAATTTCTGAATATACATA
                                                                           am

GTATTTATTTGGGGAGTACTAAAAATAATTGAAAAGGGTTTATAATCCTTTTTAATAAAATTTT AGGAGT GTTT

AAA ATG GAA GCA GTA AAA GAA AAA GAA AAA AAT GAT CTT TTT AAT CTT GAT GTT AAA GTT AAT GCA
    M   E   A   V   K   E   K   E   K   N   D   L   F   N   L   D   V   K   V   N   A
    -30                                      -20

AAA GAA TCT AAC GAT TCA GGA GCT GAA CCA AGA ATT GCT AGT AAA TTT ATA TGT ACT CCT
 K   E   S   N   D   S   G   A   E   P   R   I   A   S   K   F   I   C   T   P
        -10                              -1  +1

GGA TGT GCA AAA ACA GGT AGT TTT AAC AGT TAT TGT TGT TAATTCAGAAGAATTAGATTGGCAGG
 G   C   A   K   T   G   S   F   N   S   Y   C   C    oc
    +10                          +20
                                                              400

CTTCAATAGAGGCTCTGTCTTAATTTTGAGGTGAAATAGAATTGGATAATAATATATTGTTCCATCGAATATATATGGT
          am

FIG.1

EMS 5 plus pCuGal (Gallidermin)

```
ESTD
   RT         AREA     TYPE   CAL #    AMOUNT
  0.73    8.4107E+07   1SBH             0.000
  0.88       434710    DTBB             0.000
  1.01    3.7223E+07    SHH             0.000
  1.29      4978700     SHH             0.000
  1.38    5.3775E+07   ISHH             0.000
  1.53       349830     TBB             0.000
  2.78       343360     TPB             0.000
  3.78       444590     TBY             0.000
  4.03       218110     TYY             0.000
  7.54       408470     TYB      1     11.519
  9.63       132570     TBP             0.000

TOTAL AREA = 1.8242E+08
MIN FACTOR = 1.0000E+00
```

Gallidermin- Standard

ESTD

| RT | AREA | TYPE | CAL # | AMOUNT |
|---|---|---|---|---|
| 0.80 | 111200 | YH | | 0.000 |
| 0.87 | 1.0928E+07 | SHB | | 0.000 |
| 0.99 | 153190 | DTBB | | 0.000 |
| 5.92 | 156570 | PY | | 0.000 |
| 6.36 | 967060 | YY | | 0.000 |
| 7.15 | 580800 | PY | | 0.000 |
| 7.54 | 7492100 | YB | 1 | 211.280 |
| 8.65 | 212540 | BB | | 0.000 |
| 9.61 | 413430 | PY | | 0.000 |
| 9.68 | 256920 D | YY | | 0.000 |
| 9.94 | 255140 I | YH | | 0.000 |

TOTAL AREA = 2.1527E+07
MIN FACTOR = 1.0000E+00

```
      BglII            20                    40
     AGATCTTGTGTTATATAACTAAACAAATTTCTCCATTCGTATTTAGAAAATTGACT
        D  Q  T  I  Y  S  F  L  N  R  W  E  Y  K  S  F  Q  S 60              80             100                120
    TTTATCAAGTTTATCCAAATATATATTTCCAGTATATTCTGTATTTAACCCAGCTAATATATTT
      D  L  K  K  D  L  Y  I  N  G  T  Y  E  T  N  L  G  A  L  I  N 140            160            180
    AATAATGTACTTTTTCCACACCCACTTTCACCTATAATATTGTAGATATAACCTTTATGAAGAT
      L  L  T  S  K  G  C  G  S  E  G  I  I  N  Y  I  Y  G  K  H  L  D 200            220            240
    CCAAACTTATAGAATTTATTATTTGTTTATTGTCTTTTGTGAAGTTCAAATCATTTATTTCCAT
      L  S  I  S  N  I  I  Q  K  N  D  K  T  F  N  L  D  N  I  E  M 260            280            300
    TTTTTGAACAAAGTTATTGTAAGTTGTTTTAATAGTTAATACCTCTTCTGGTTCTTTATTTATT
      K  Q  V  F  N  N  Y  T  T  K  I  T  L  V  E  E  P  E  K  N  I 320            340            360
    TTTAAAATTCTATCTGAAGATCCAATTGCTCGTTGTACTTCCGTCCAATAAGATGTAATAGATA
      K  L  I  R  D  S  S  G  I  A  R  Q  V  E  T  W  Y  S  T  I  S  V 380            400            420               440
    CTATTGGATTAATAATTTGAAATAAATATAAAACATAAGCAAACATATCTCCGCTTTTCATCAT
       I  P  N  I  I  Q  E  L  Y  L  V  Y  A  F  M  D  G  S  K  M  M 460            480            500
    ATTATTTTCCATTAAGTAATAACCCAAAAATAAAATACCAAAAATGTTAATAAATAGAATTAAG
       N  N  E  H  L  Y  Y  G  L  F  L  I  G  F  I  N  I  F  L  I  L 520            540            560
    TTCATAATTGGTTCGAAAAAAGATAATACTTTGATCTTATGTAACTCTATATCGAATATATTTT
      N  M  I  P  E  F  F  S  L  V  K  I  K  H  L  E  I  D  F  I  N  K 580            600            620
    TTAATAGGGTATAGTTTTTTATTTTTTCGATATTATATGTACTTAAAGTTTTTATTAATTTTAT
      L  L  T  Y  N  K  I  K  E  I  N  Y  T  S  L  T  K  I  L  K  I 640            660            680
    TGTAGATAATCTATTACTATAATAAGAAGATAATTTAGCAGTAGCTTCTTGAGATTTACTTGAT
       T  S  L  R  N  S  Y  Y  S  S  L  K  A  T  A  E  Q  S  K  S  S 700            720            740               760
    ACTCTTTTCATTATATTTCCTATAGGTAGTATTACAATTATCAATATAGGTAATGTACACACTA
       V  R  K  M  I  N  G  I  P  L  I  V  I  I  L  I  P  L  T  C  V  L
```

FIG.9A

```
                  780                    800                     820
AATATAATGTCAAGGTTTTGTTAATTATATATAAAAATATTAGTGATACTATAACTGAAAATAA
   Y  L  T  L  T  K  N  I  I  Y  L  F  I  L  S  V  I  V  S  F  L
                        oc  N  Y  I  F  I  N  T  I  S  Y  S  F  I  F 840                    860                    880
ATTCTACAGAAAAAACTCTAGTTATGTTCATAGTATCGTTTACTAACCTACTAGTTAAGTTACT
  N  am
     E  V  S  F  V  R  T  I  N  M  T  D  N  V  L  R  S  T  L  N  S 900                    920                    940
TGCTGAGTTTTTTAAGTGAAAACTATAAGGTAACTTTATCACTTTATTCCATGTAACACTTCTA
  A  S  N  K  L  H  F  S  Y  P  L  K  I  V  K  N  W  T  V  S  R 960                    980                    1000
ATGTTTTGTATTATTTTTTGACCTATATATCCAAGAATATAAGTAGAAACACCAGAAAATATTA
  I  N  Q  I  I  K  Q  G  I  Y  G  L  I  Y  T  S  V  G  S  F  I  L 1020                   1040                   1060                   1080
AAGTCAGACCAAAACATATAATAATGATTACAATTTTATCTGTTGATAAGCTAGATTTGTTTAA
   T  L  G  F  C  I  I  I  I  V  I  K  D  T  S  L  S  S  K  N  L 1100                   1120                   1140
GGCATTTCTAATTATTAAAGGAATGTATAATGAAAAACTAGTTCCAATCAAACTAAATATTAGT
   A  N  R  I  I  L  P  I  Y  L  S  F  S  T  G  I  L  S  F  I  L 1160                   1180                   1200
CCAATACTTAAAAGTAGAGTGTTAGGTTTGGTTATTTTCCATAAATCATATAGACCTTTGATAA
   G  I  S  L  L  L  T  N  P  K  T  I  K  W  L  D  Y  L  G  K  I  I

S/D                 1240                   1260
TATCATCACCTTTTAAACTTTATATCATTAATATAATGTTTAGGAAAAGTAGAAGAAAATTACA
    D  D  G  K  L  S  <  epiY IR  1280                   1300                   1320
CTTTTGTAATTTTCTGAATATACATAGTATTTATTTTGGGGGAGTACTAAAATAATAATTGAAA 1340    IR             1360        S/D     1380epiA >              1400
AGGGTTTTATAATCCTTTTTAATAAATTTTTAGGAGTGTTTAAAATGGAAGCAGTAAAAGAAAA
                                                 M  E  A  V  K  E  K 1420                   1440                   1460
AAATGATCTTTTTAATCTTGATGTTAAAGTTAATGCAAAAGAATCTAACGATTCAGGAGCTGAA
   N  D  L  F  N  L  D  V  K  V  N  A  K  E  S  N  D  S  G  A  E
```

FIG. 9B

```
                    1480                    1500                    1520
         CCAAGAATTGCTAGTAAATTTATATGTACTCCTGGATGTGCAAAAACAGGTAGTTTTAACAGTT
           P  R  I  A  S  K  F  I  C  T  P  G  C  A  K  T  G  S  F  N  S 1540                    1560                    1580
         ATTGTTGTTAATTCAGAAGAATTAGATTGGCAGGGCTTCAATAGAGGCTCTGTCTTAATTTTGA
           Y  C  C  oc                                                epiB >

S/D1600                    1620                    1640
         GGTGAAATAGAATTGGATAATATATTTGTTCCATCGAATATATATATGGTAAGAACTCCTATAT
           G  E  I  E  L  D  N  I  F  V  P  S  N  I  Y  M  V  R  T  P  I 1660                    1680                    1700                    1720
         TTTCAATTGAATTATATAATCAATTCTTAAAATCTGACAATATAGATTATGACTTAATTTTACA
           F  S  I  E  L  Y  N  Q  F  L  K  S  D  N  I  D  Y  D  L  I  L  Q 1740                    1760                    1780
         AAACGATATTTTTAAAGAATCTATAATGACAACGACATATAATCTTTATCAAAGTATTGGCAAA
           N  D  I  F  K  E  S  I  M  T  T  T  Y  N  L  Y  Q  S  I  G  K 1800                    1820                    1840
         ATAGACTGGGAAAAGGATAATAAAAAAACCAGAAATGTAAAAGAAAGTTTATTAAAATATCTCA
           I  D  W  E  K  D  N  K  K  T  R  N  V  K  E  S  L  L  K  Y  L 1860                    1880                    1900
         TAAGAATGAGTACTAGAAGTACACCATATGGAATGCTAAGCGGTGTAGCTTTAGGGGAATTTAG
           I  R  M  S  T  R  S  T  P  Y  G  M  L  S  G  V  A  L  G  E  F  S 1920                    1940                    1960
         TGAAAATAATAATATTAAAATTAAGGACTCTTCGTTTCATAAAAAAGATGTAAAAATAGATGGG
           E  N  N  I  K  I  K  D  S  S  F  H  K  K  D  V  K  I  D  G 1980                    2000                    2020                    2040
         CAATGGTTATATAAATTAGTCCATTATTTAGAAAGCGATTACACATATTATAAAGACAGTTTTG
           Q  W  L  Y  K  L  V  H  Y  L  E  S  D  Y  T  Y  Y  K  D  S  F 2060                    2080                    2100
         TCATATGGAATCAACAAAATTATATTTATAACAATCGTTTATATTTAGATAATAATTCATCAAT
           V  I  W  N  Q  Q  N  Y  I  Y  N  N  R  L  Y  L  D  N  N  S  S  I 2120                    2140                    2160
         CACTGAAAATAAAAGAAATGATGTATTATCTGTCAAATACAATTCTATATTAGTGTTTATACAT
           T  E  N  K  R  N  D  V  L  S  V  K  Y  N  S  I  L  V  F  I  H
```

FIG.9C

```
         EcoRI  2180                2200                2220
        GAGAATTCTAAAAAAAATATTACTTATGAAGAACTTGTACAATTGATATCTAGTAAGTACAGTA
         E  N  S  K  K  N  I  T  Y  E  E  L  V  Q  L  I  S  S  K  Y  S 2240                2260                2280
        TAGAAAATAAAGAAGAAGTAAAAGTATTTGTTCAAGAACTCATAAATAAAGAAATTATATTTTC
         I  E  N  K  E  E  V  K  V  F  V  Q  E  L  I  N  K  E  I  F  S 2300                2320                2340                2360
        TGATTTGAGACCTACATTAGAGAATAAAAATCCTTTAGATTACATTATTAATAGTTTAAATCCA
         D  L  R  P  T  L  E  N  K  N  P  L  D  Y  I  I  N  S  L  N  P 2380                2400                2420
        AAAAATAGTTTAGTTGGAACACTTATTAATATTTCTAATGAAATTACAAAATATTCTAAAATGC
         K  N  S  L  V  G  T  L  I  N  I  S  N  E  I  T  K  Y  S  K  M 2440                2460                2480
        CTTTAGGAAAAGGAGAATATAAATATTTAGATATTGTTAATTTAATGTCACAATTATTTGTTTC
         P  L  G  K  G  E  Y  K  Y  L  D  I  V  N  L  M  S  Q  L  F  V  S 2500                2520                2540
        TAAAAACTATTTGCAAATAGATACCTATATAGATTATTCAAGAAATGAATTAAAACAAAGTTTA
         K  N  Y  L  Q  I  D  T  Y  I  D  Y  S  R  N  E  L  K  Q  S  L 2560                2580                2600
        GCTGATAATATTAGTGAAGCAGCATATATTCTCTGGTTATTATCTCCTAATCATTTTGGTACAA
         A  N  D  I  S  E  A  A  Y  I  L  W  L  L  S  P  N  H  F  G  T 2620                2640                2660                2680
        AAACTATTAGGAATTATCACGAATTTTTTATGGATAAATATGGATTTGAACAACTAGTAAATTT
         K  T  I  R  N  Y  H  E  F  F  M  D  K  Y  G  F  E  Q  L  V  N  L 2700                2720                2740
        AAAGCAATTGCTCTCAGATATAAATGGATTTGGCTATCCCAAAAAAGACAGTTATAGTTTTTCT
         K  Q  L  L  S  D  I  N  G  F  G  Y  P  K  K  D  S  Y  S  F  S 2760                2780                2800
        AATAACATTGCATTTTTAAAAGAAAAGTATTTGCTTGCAATTCAAAATAACAGCCATATTGAAA
         N  N  I  A  F  L  K  E  K  Y  L  L  A  I  Q  N  N  S  H  I  E 2820                2840                2860
        TAACAGAAAACGACGTTAAAAATTTAGAAAAGAATAATACAGTTTCTAAAATCAATGCGCCTGT
         I  T  E  N  D  V  K  N  L  E  K  N  N  T  V  S  K  I  N  A  P  V
```

FIG.9D

```
       2880              2900              2920
TTCAACTGAAATATATAGTGAGATATATTTTGGAAATTCAATAAAAGGTTATGAGGATTTTGCC
  S  T  E  I  Y  S  E  I  Y  F  G  N  S  I  K  G  Y  E  D  F  A 2940              2960              2980              3000
GTGATAAGTCCAATATTAGGATCTTTTAATGCCGGTGCAACTTTTGGAAGGTTTACGGGAAATT
  V  I  S  P  I  L  G  S  F  N  A  G  A  T  F  G  R  F  T  G  N 3020              3040              3060
TCAATATAAAGAAAAAAAATCAATTACAAAAAGAAATAGTGCATCATTACAATAATTACATGAA
  F  N  I  K  K  K  N  Q  L  Q  K  E  I  V  H  H  Y  N  N  Y  M  N 3080              3100              3120
TGAAAATGGTTTAGAAATAAGCCAATTAAATGAAGGTCCTCTTAACTCAAGAAATGTAAATATT
   E  N  D  L  E  I  S  Q  L  N  E  A  P  L  N  S  R  N  V  N  I 3140              3160              3180
TTGAATAATAATAGAATATATAATACTTGTTTAAATTTAAATTTACCTAAAAGTGATATAGATA
  L  N  N  N  R  I  Y  N  T  C  L  N  L  P  K  S  D  I  D 3200              3220              3240
TAAATGACATATTTATTGGAGCTACATTTAACAAACTTTATCTATATTCTGAAAAACATGATTC
  I  N  D  I  F  I  G  A  T  F  N  K  L  Y  L  Y  S  E  K  H  D  S 3260              3280              3300              3320
AAGAATTGTATTCGTATCTAATTCAATGTTTAATTATGAGTTTGGATCTGAATTATACAAATTT
   R  I  V  F  V  S  N  S  M  F  N  Y  E  F  G  S  E  L  Y  K  F 3340              3360              3380
TTAAGAGAAATTTCATTTGAAAAAACAAAATTTATACAACCTATAACTGAAGAAGGCATTGACT
  L  R  E  I  S  F  E  K  T  K  F  I  Q  P  I  T  E  E  G  I  D 3400              3420              3440
CATTACCTTTTTGTCCAAGAATTATTTATAAAAATATTATTTTAAAACCAGCTACTTGGAAAAT
  S  L  P  F  C  P  R  I  I  Y  K  N  I  I  L  K  P  A  T  W  K  I 3460              3480              3500
AAATTCAGAAATGTTTTCTGAAACTGAAAATTGGTTAAATAGGTTCGCAACTATTAGAGAAAAA
  N  S  E  M  F  S  E  T  E  N  W  L  N  R  F  A  T  I  R  E  K 3520              3540              3560
TGGCATATTCCAAAAGATGTAATTATTGCTTTTGGAGATAATCGATTGCTATTAAATTTATTAA
  W  H  I  P  K  D  V  I  I  A  F  G  D  N  R  L  L  L  N  L  L
```

FIG.9E

```
             3580                3600                3620                3640
ATGACAAGCATCTCATTATACTAAAAAAAGAACTAAAAAAACATGGTAGGATTCGAATATTAGA
  N  D  K  H  L  I  I  L  K  K  E  L  K  K  H  G  R  I  R  I  L  E

HindIII          3660                3680                3700
AAGCTTTATCAATGAATCTAATAATGAGAGAATGTTAGAAATTGTTACGCCATTATATAAAAAA
   S  F  I  N  E  S  N  N  E  R  M  L  E  I  V  T  P  L  Y  K  K 3720                3740                3760
ACTAGTTTAAAAGAACAATCTTTCATTATACCTAAAAATAGAAATAAGCACTTCAATAATCTTA
   T  S  L  K  E  Q  S  F  I  I  P  K  N  R  N  K  H  F  N  N  L 3780                3800                3820
AAGATTGGTTTTCAATTCATTTAAGTATTCCTAAAACATACCAAGATAATTTTATTCAAGATTA
   K  D  W  F  S  I  H  L  S  I  P  K  T  Y  Q  D  N  F  I  Q  D  Y 3840                3860                3880
TCTATTACCATTTATAACGGAATTAAAAGTTAATAATTTTATTAATAAATTTTTTTACATAAAA
   L  L  P  F  I  T  E  L  K  V  N  N  F  I  N  K  F  F  Y  I  K 3900                3920                3940                3960
TTTAAAGAAGATGAAGATTTTATAAAATTAAGATTATTAAGAGAAGATGAAGATTATTCTCAAA
  F  K  E  D  E  D  F  I  K  L  R  L  L  R  E  D  E  D  Y  S  Q 3980                4000                4020
TTTATTCTTTCATAAAAAATTGGAAAGATTATTGCTTATTAAATAGTGAATTATATGACTATTC
  I  Y  S  F  I  K  N  W  K  D  Y  C  L  L  N  S  E  L  Y  D  Y  S 4040                4060                4080
TATAGTTGATTATGTTCCTGAAGTATATAGATATGGTGGTCCACACGTAATTGAAGATATTGAG
   I  V  D  Y  V  P  E  V  Y  R  Y  G  G  P  H  V  I  E  D  I  E 4100                4120                4140
AATTTTTTTATGTATGATAGTCTATTATCAATAAATATAATACAATCAGAGTTCAAAATTCCAA
   N  F  F  M  Y  D  S  L  L  S  I  N  I  I  Q  S  E  F  K  I  P 4160                4180                4200
AAGAATTTATCGTTGCTATATCAATAGATTTTTTATTAGATTATTTAGAAATTAATAAAAGTGA
   K  E  F  I  V  A  I  S  I  D  F  L  L  D  Y  L  E  I  N  K  S  E 4220                4240                4260                4280
GAAAGAAGAAATTTTAATTAATAATGCGGAAGATTTATATCGTAGTAATGACATAAGAGAATAT
   K  E  E  I  L  I  N  N  A  E  D  L  Y  R  S  N  D  I  R  E  Y
```

FIG.9F

```
                4300              4320              4340
AAAAATTTATTAGCTAAACTTACCAATCCTAAAAATGACTATGAAATTTTAAAAAAAGAATTTC
 K  N  L  L  A  K  L  T  N  P  K  N  D  Y  E  I  L  K  K  E  F 4360              4380              4400
CGAATCTTCATGAATTTCTATTTAATAAAATTAGTATTTTAGAAAATCTTAAAAAGACACTACA
 P  N  L  H  E  F  L  F  N  K  I  S  I  L  E  N  L  K  K  T  L  Q

HindIII            S/D  epiC >      4460
AAAAAGCTTATATACTTCACGTTCTAGGATAATTGGCAGTTTTATACACATGCGTTGTAATAGA
  K  S  L  Y  T  S  R  S  R  I  I  G  S  F  I  H  M  R  C  N  R
                                    L  A  V  L  Y  T  C  V  V  I  E 4480              4500              4520
ATATTCGGTATTAATCCTGAAAAAGAAAAATTTGTTTTATCTATTTTTAATGAAATTACAAAAA
  I  F  G  I  N  P  E  K  E  K  F  V  L  S  I  F  N  E  I  T  K
   Y  S  V  L  I  L  K  K  K  N  L  F  Y  L  F  L  M  K  L  Q  K 4540              4560              4580              4600
CTAAAAAATATTGGGATGGTTGTGATTAATATTAATAACATTAAAAAAATTTTAGAAAATAAAA
 T  K  K  Y  W  D  G  C  D oc      oc oc
    L  K  N  I  G  M  V  V  I  N  I  N  N  I  K  K  I  L  E  N  K 4620              4640              4660
TCACCTTTTTGTCTGACATTGAAAAAGCTACATATATTATAGAAAATCAAAGTGAGTATTGGGA
 I  T  F  L  S  D  I  E  K  A  T  Y  I  I  E  N  Q  S  E  Y  W  D 4680              4700              4720
TCCTTATACTCTATCTCATGGTTATCCAGGTATAATACTTTTTTTAAGCGCATCAGAAAAAGTA
  P  Y  T  L  S  H  G  Y  P  G  I  I  L  F  L  S  A  S  E  K  V 4740              4760              4780
TTTCATAAAGATTTAGAAAAAGTAATACATCAATATATTAGAAAACTAGGCCCTTATTTAGAAA
 F  H  K  D  L  E  K  V  I  H  Q  Y  I  R  K  L  G  P  Y  L  E 4800              4820              4840
GTGGTATTGATGGATTTTCACTTTTTAGTGGTCTTTCCGGAATTGGATTTGCGCTAGACATTGC
 S  G  I  D  G  F  S  L  F  S  G  L  S  G  I  G  F  A  L  D  I  A 4860              4880              4900              4920
GTCTGATAAACAGTACTCTTATCAAAGTATCTTAGAACAAATTGATAATTTACTTGTTCAATAT
  S  D  K  Q  Y  S  Y  Q  S  I  L  E  Q  I  D  N  L  L  V  Q  Y 4940              4960              4980
GTTTTTGATTTTTTAAATAACGATGCATTGGAAGTAACCCCTACTAACTATGATATAATACAAG
 V  F  D  F  L  N  N  D  A  L  E  V  T  P  T  N  Y  D  I  I  Q
```

FIG.9G

```
                5000                5020                5040
GATTTTCTGGTATAGGAAGGTACTTGTTAAATAGAATATCGTATAATTATAATGCAAAAAAAGC
 G  F  S  G  V  G  R  Y  L  L  N  R  I  S  Y  N  Y  N  A  K  K  A 5060                5080                5100
ATTAAAGCATATACTTAATTACTTCAAAACAATTCATTACTCTAAAGACAATTGGTTAGTTTCA
 L  K  H  I  L  N  Y  F  K  T  I  H  Y  S  K  D  N  W  L  V  S 5120            5140                5160
AATGAACATCAATTTTTAGATATAGATAAGCAAAATTTTCCGTCAGGAAATATAAATTTAGGAT
 N  E  H  Q  F  L  D  I  D  K  Q  N  F  P  S  G  N  I  N  L  G 5180                5200                5220                5240
TAGCGCATGGTATTTTAGGTCCTCTATCATTAACAGCTTTGAGTAAAATGAATGGGATTGAAAT
 L  A  H  G  I  L  G  P  L  S  L  T  A  L  S  K  M  N  G  I  E  I 5260                5280          EcoRI
CGAAGGCCATGAAGAGTTTTTACAAGACTTCACTTCATTTTTGCTCAAACCTGAATTCAAAAAT
 E  G  H  E  E  F  L  Q  D  F  T  S  F  L  L  K  P  E  F  K  N 5320                5340                5360
AATAATGAATGGTTCGATCGCTATGATATATTAGAAAAATTATATACCTAATTATTCCGTCAGAA
 N  N  E  W  F  D  R  Y  D  I  L  E  N  Y  I  P  N  Y  S  V  R 5380                5400                5420
ACGGTTGGTGTTACGGTGATACAGGGATTATGAATACATTACTTTTGTCTGGTAAAGCCTTAAA
 N  G  W  C  Y  G  D  T  G  I  M  N  T  L  L  S  G  K  A  L  N 5440                5460            5480
TAATGAAGGCTTAATTAAAATGTCTAAAAATATTTTAATTAACATAATAGATAAGAATAATGAT
 N  E  G  L  I  K  M  S  K  N  I  L  I  N  I  I  D  K  N  N  D 5500                5520                5540                5560
GATTTAATCAGTCCAACCTTCTGTCACGGACTAGCATCGCACTTAACCATTATTCATCAAGCGA
 D  L  I  S  P  T  F  C  H  G  L  A  S  H  L  T  I  I  H  Q  A 5580                5600                5620
ATAAATTCTTTAATCTATCTCAAGTAAGCACATATATCGATACCATTGTCAGAAAAATTATTAG
 N  K  F  F  N  L  S  Q  V  S  T  Y  I  D  T  I  V  R  K  I  I  S 5640                5660                5680
TCATTATTCTGAAGAAAGTAGTTTTATGTTCCAAGACATAGAGTACTCATACGGACAAAAAATT
 H  Y  S  E  E  S  S  F  M  F  Q  D  I  E  Y  S  Y  G  Q  K  I

5700    EcoRI    5720                5740
TATAAAAACAAAGTGGGAATTCTAGAGGGTGAATTAGGTGTTCTTTTAGCTTTACTAGATTATA
 Y  K  N  K  V  G  I  L  E  G  E  L  G  V  L  L  A  L  L  D  Y
```

FIG.9H

```
        5760                5780                5800         S/D
TTGATACACAAAACCAATCAAGGAAAAATTGGAAAAATATGTTTTTAATAACATAATAGGAGGA
 I  D  T  Q  N  Q  S  R  K  N  W  K  N  M  F  L  I  T oc 5820   epiD >       5840                5860                5880
ATAAGATATGTATGGAAAATTATTGATATGCGCTACAGCATCGATAAATGTAATTAATATTAAT
        M  Y  G  K  K  L  L  C  A  T  A  S  I  N  V  I  N  I  N 5900                5920                5940
CACTACATAGTTGAGTTAAAGCAACATTTTGATGAAGTTAATATATTATTTAGTCCTAGTAGTA
 H  Y  I  V  E  L  K  Q  H  F  D  E  V  N  I  L  F  S  P  S  S 5960                5980                6000
AAAATTTTATAAATACTGATGTTCTCAAGTTATTTTGTGATAACTTGTACGATGAAATTAAAGA
 K  N  F  I  N  T  D  V  L  K  L  F  C  D  N  L  Y  D  E  I  K  D 6020                6040                6060
TCCTCTTTTAAATCATATCAATATTGTAGAAAATCATGAATATATTTTAGTATTACCTGCATCA
  P  L  L  N  H  I  N  I  V  E  N  H  E  Y  I  L  V  L  P  A  S 6080                6100                6120
GCAAATACTATTAATAAAATAGCTAATGGTATATGTGATAATCTTTTAACTACTGTATGTTTAA
  A  N  T  I  N  K  I  A  N  G  I  C  D  N  L  L  T  T  V  C  L EcoRV           6160                6180                6200
CCGGATATCAAAAATTATTTATATTTCCAAATATGAACATAAGAATGTGGGGAAATCCATTTTT
  T  G  Y  Q  K  L  F  I  F  P  N  M  N  I  R  M  W  G  N  P  F  L 6220                6240                6260
ACAAAAAAATATTGATTTACTTAAAAATAATGATGTGAAAGTGTATTCCCCTGATATGAATAAA
  Q  K  N  I  D  L  L  K  N  N  D  V  K  V  Y  S  P  D  M  N  K 6280                6300                6320
TCATTCGAAATATCTAGTGGCCGTTACAAAAACAATATCACAATGCCTAATATTGAAAATGTAC
  S  F  E  I  S  S  G  R  Y  K  N  N  I  T  M  P  N  I  E  N  V 6340           6360 Terminator    6380
TAAATTTTGTATTAAATAACGAAAAAAGACCTTTGGATTAACAAAGGTCTTTTCTAATTAAAAT
  L  N  F  V  L  N  N  E  K  R  P  L  D oc
                                        oc C  L  D  K  R  I  L  I 6400                6400                6440
TTTATATCCGAGTTTACGTTCATTAATAATTTCTATCTCTTTACAATTTTTTAAACTATCCCTT
  K  Y  G  L  K  R  E  N  I  I  E  I  E  K  C  N  K  L  S  D  R
```

FIG.91

```
              6460              6480              6500              6520
AATCGATGGATATATACATTTATTGTATTAGAATCAACAAAGTCTTCTGTATCCCACACTCCCT
 L  R  H  I  Y  V  N  I  T  N  S  D  V  F  D  E  T  D  W  V  G  K 6540              6560              6580
TTTTTAATTCCTCTTTTGATACATATCTTCCAAGATTAATATATAAGCACCGTAGAATTTTTAA
  K  L  E  E  K  S  V  Y  R  G  L  N  I  Y  L  C  R  L  I  K  L 6600              6620              6640
TTCTATATTAGAAAGATTAACTAAGTAATTATTAAACACAAATTGATGGTTTTCAAAGTCTATA
  E  I  N  S  L  N  V  L  Y  N  N  F  V  F  Q  H  N  E  F  D  I 6660              6680              6700
AAATCATCATTAACATATTTAATATACTTTTTTATTTCATTTAAAATTCTACATAATATTAAAC
 F  D  D  N  V  Y  K  I  Y  K  K  I  E  N  L  I  R  C  L  I  L  S 6720              6740              6760
TTTTGCTTTCATTATTTTTTATAATATATAAATCTATGCCTAAACTATAAAAATAACACTTCCT
  K  S  E  N  N  K  I  I  Y  L  D  I  G  L  S  Y  F  Y  C  K  R 6780              6800              6820              6840
ACTATAGCTAGTATTACCTGTTATTATAACTATTGGAATTTTTCCTATAAATTCTTTTAAAAAC
  S  Y  S  T  N  G  T  I  I  V  I  P  I  K  G  I  F  E  K  L  F 6860              6880              6900
GTATAATACTCATCAAACTTTTCATACACAATTATAAAATTTGGGTCTATATTTGAAGAATTAA
  T  Y  Y  E  D  F  K  E  Y  V  I  I  F  N  P  D  I  N  S  S  N  I 6920              6940              6960
TTGTAATTCTTCTATCTAATTCTAAAATACTTTCAATAAGAATAGAATCTACCTCACCGACAAT
  T  I  R  R  D  L  E  L  I  S  E  I  L  I  S  D  V  E  G  V  I

6980      S/D   7000              7020
ATTAATAGAAATCATTTTATTCCCTTCATTCTTTAAGTAATTTGTATACGTCAGTTTTCCATT
  N  I  S  I  M < epiQ   op    E  K  L  L  K  Y  V  D  L  K  G  N 7040              7060              7080
ACCATAATGTTTTTTATCCATATATTTTTCTTTTTCTATCCCTTTTTTCTTAAATAACTCTATA
  G  Y  H  K  K  D  M  Y  K  E  K  E  I  G  K  K  K  F  L  E  I 7100              7120              7140              7160
GCTGTTTCGGGTTGGTCTTTTAATTGATACTTATCAATTTCTAGTGCTAAAGCTCCAGAAACCT
  A  T  E  P  Q  D  K  L  Q  Y  K  D  I  E  L  A  L  A  G  S  V  K
```

FIG.9J

```
              7180                  7200                  7220
TGGGTGCAGCAAGTGATGTCCCTGATTGATATATGTATCTTCCATTAGAAGAAGTACTTAAAAC
  P  A  A  L  S  T  G  S  Q  Y  I  Y  R  G  N  S  S  T  S  L  V 7240                  7260                  7280
ACTTTGTTTTTGCATATATCCTTTTTCTAACCAAGCATCTTTTCCATACTTATCTAAAAGTTTA
  S  Q  K  Q  M  Y  G  K  E  L  W  A  D  K  G  Y  K  D  L  L  K 7300                  7320                  7340
TAAGAACCTCCTATCGTCATTAAATCTATAAAATTATTTCCATAATTAGAAAACTCAGAAATAT
  Y  S  G  G  I  T  M  L  D  I  F  N  N  G  Y  N  S  F  E  S  I  Y

7360       BamHI   7380                  7400
AATCATTATCATCGATGGATCCTACAGTCATAACATTATTTAGATTTGCTGGGCTATCATATAC
  D  N  D  D  I  S  G  V  T  M  V  N  N  L  N  A  P  S  D  Y  V 7420                  7440                  7460                  7480
CTTTTTTGATGTTTTAGAATTTAGATTTCTTTTTTTATTTATTTCTTTTACTTTTTTTACATTG
  K  K  S  T  K  S  N  L  N  R  K  K  N  I  E  K  V  K  K  V  N 7500                  7520                  7540
ATACCGTCATTACCCACAGCTGCAACAACAATACTACCTTTTTTTTGAGCATAGTTTATAGCTT
  I  G  D  N  G  V  A  A  V  V  I  S  G  K  K  Q  A  Y  N  I  A  K 7560                  7580                  7600
TCTGTAGTGCATCGTAATCAACTTTTTCATCATCTCTTAATTTTTTTTATTTTGATTATCTTT
  Q  L  A  D  Y  D  V  K  E  D  D  R  L  K  K  N  Q  N  D  K 7620                  7640                  7660
AATTAAATAATTTCCTAAACTAACGTTGATTACATCATTGTCATCATTTGCTGCATCAATAATT
  I  L  Y  N  G  L  S  V  N  I  V  D  N  D  D  N  A  A  D  I  I 7680                  7700                  7720
CCTTTAGATACCCAAAGCATTTCACTTTTCTTTGAGCCAAATACTCGGTATACATTCATCTCTA
  G  K  S  V  W  L  M  E  S  K  K  S  G  F  V  R  Y  V  N  M  E  V 7740                  7760                  7780                  7800
CTCCAGGGTTTACACCTTTTAAATTACCGTTTGCTCCTATTTGTCCTGCTACTAATGTACCATG
  G  P  N  V  G  K  L  N  G  A  G  I  Q  G  A  V  L  T  G  H 7820                  7840                  7860
ATTCAATTTATCTTCTTCAAAATTTTTATTTCCTGATTCATCGTTTTCGCTACCTCTAAAACCA
  N  L  K  D  E  E  F  N  K  N  G  S  E  D  N  E  S  G  R  F  G
```

FIG. 9K

```
           7880                7900                  7920
TTTTTAGGCACTTCATTAACTATCTTATTTATACTCTTTAAATCTGTATGACTACTATTCACAC
 N  K  P  V  E  N  V  I  K  N  I  S  K  L  D  T  H  S  S  N  V  G 7940                7960                  7980
CAGAATCTACTAAAGCAACTTTTGCTTTTTTTCTATCTGGACTTAGCTTATAACTTTTACCTTC
  S  D  V  L  A  V  K  A  K  K  R  D  P  S  L  K  Y  S  K  G  E 8000                8020                 8040
ATTTGTTATTTTTCGCATATCCCATTGTCTGTCAAATAAATCATGGCTGCCATTTTTTTTATTA
  N  T  I  K  R  M  D  W  Q  R  D  F  L  D  H  S  G  N  K  K  N 8060                8080               8100                   8120
TTTAAATTTTTTCCTGTCTTTACAGATTTTTCAACTACACAAGTGGAACAGGTAGGATTTACAA
 N  L  N  K  G  T  K  V  S  K  E  V  V  C  T  S  C  T  P  N  V  F 8140                8160                 8180
ACTTGACGTTTTTATTACTCTTTATTAGTGAATTTAATTTTGATTTGCTAGTTTTAATTTGTGC
   K  V  N  K  N  S  K  I  L  S  N  L  K  S  K  S  T  K  I  Q  A

8200        HindII 8220                8240
TGTATGTAGTTCAGGAATTTTATAAGTTAACTCGATATTTTTTGTTTAATGGATTCTTTAAAA
  T  H  L  E  P  I  K  Y  T  L  E  I  N  K  Q  K  I  S  E  K  F 8260                8280                 8300
GTTTTTGCATTATCATATTCAACACTATAATAACTTAATTCTTCATTTAGTGAACTTCCAAAAG
  T  K  A  N  D  Y  E  V  S  Y  Y  S  L  E  E  N  L  S  S  G  F  A 8320                8340                8360
CATACTCATTTTGCAAAAAAACTAATGACAATATTAAAAAAACAATGAAAAATTTAAATTTGTT
    Y  E  N  Q  L  F  V  L  S  L  I  L  F  V  I  F  F  K  F  K  N 8380     S/D                 8400              8420                 8440
CATATAGCACCTCTAACATATTATTTATATTAAACATTAATTTAACACTTATGTTTTTACTTTT
  M  <  epiP 8460              8480                  8500
TTATTTATATTATCTTTAATAATGTTCTGTTGCAAGATGAAAAATACGAGGTATCAAAGTACCG 8520              8540                  8560
ATACAGCGAGTATTACACTCAATTAATTAAAAATAAAATATGTTGTGATTAAAATTTATTTTAT 8580              8600        KpaII
AAAAGTATGGGCAATTTATTATTATTCAAGTTAAAACAAAGAGTCCGGGACATAAAGTTTCAGC 8640              8660              8680
CTCTTCGTCCTAATTACCAAAAAAACTTACTCCAAAATCCTTTTTTAGATTGGTTTTTTCTAATT

8700
TTTT                   FIG.9L
```

Active site I:

```
EPIP    130   EGKSYKLSPDRKKAKVALVDSGVNSSHTDLKSINKIVNEVP   170
              ..:::.:::..:::::
SUBSI   119   APALHSQGYTGSNVKVAVIDSGIDSSHPDLNVRGGASFVPS   159
              ..  :::...:: ::::::.:::.
ISPI     31   APEMWAKGVKGKNIKVAVLDTGCDTSHPDLKNQIIGGKNFS    71
              ::.:.::.::.:.:::
SUMYTV   19   QAPQAWDIAEGSGAKIAIVDTGVQSNHPDLAGKVVGGWDFV    59
```

Active site II:

```
EPIP    170   PKNGFRGSENDESGNKNFEEDKLNHGTLVAGQIGANGNLKGVNPGVEMNVY   220
              :. . :::...  .....  .:  .:::  :::  :::  .:   ::
SUBSI   146   PDLNVRGGASFVPSETNPYQDGSSHGTHVAGTIAALNNSIGVLGVSPSASL   196
              .:.......    .:    .::: :::  ......   ..
ISPI    163   QIIGGKNFSDDDGGKEDAISDYNGHGTHVAGTIAANDSNGGIAGVAPEASL   113
              :::   ::
SUMYTV   67                           NGNGHGTHCAGIAAAVTNNST                87
```

Active site III:

```
EPIP    380   YMQKQSVLSTSSNGRYIYQSGTSLAAPKVSGALALEIDKYQ   420
              :.  ::  ...  :    .::::.:::::::  ::   ...:
SUBSI   305   MAPGVSIQSTLPGGTYGAYNGTSMATPHVAGAAALILSKHP   345
              .......:: ..   .:::::.::::::::::::::  :::::.
ISPI    224   VAPGENILSTLPNKKYGKLTGTSMAAPHVSGALAL-ISKYE   263
              . ::  ...  :      :::::::::::::::    .:
SUMYTV  203   AAPGSWIYSTYPTSTYASLSGTSMATPHVAGVAGLLASQGR   243
```

FIG. 11

```
              10         20         30        40         50         60
EPIQ    MISINIVGEVDSILIESILELDRRITINSSNIDPNFIIVYEKFDEYYTFLKEFIGKIPIV
                                                               ::.:
PHOB    VLEQNGFQPVEAEDYDSAVNQLNEPWPDLILLDWMLPGGSGIQFIKHLKRESMTRDIPVV
              30        40         50        60         70         80

70        80         90       100        110
EPIQ    IITGNTSYSRKCYFYSLFIDLYIIKNNESKSLILCRILNEIKKYIKYVNDDFID-----F
         ..  ..   .   . : ::.:   .....  ::   ...   .. :.       .
PHOB    MLTARGEEEDRVRGLETGADDYITKPFSPKELV-ARIKAVMRRISPMAVEEVIEMQGLSL
              90       100        110       120         130

120        130        140       150        160       170
EPIQ    E---NHQFVFNNYLVNLSNIELKILRCLYINLGRYVSKEELKKGVWDTEDFVDSNTINVYI
         .::  .  ..   ....  .:::.:   . .:  :::.: . ::::. ..:::::.:.:
PHOB    DPTSHRVMAGEEPLEMGPTEFKLLHFFMTHPERVYSREQLLNHVWGTNVYVEDRTVDVHI
             150        160        170       180         190

180        190       200
EPIQ    HRLRDSLKNCKEIEIINE-RKLGYKILIRKDLC
         .::::..   .... :  .... ..
PHOB    RRLRKALEPGGHDRMVQTVRGTGYRFSTRF
             200        210         220
```

FIG. 12

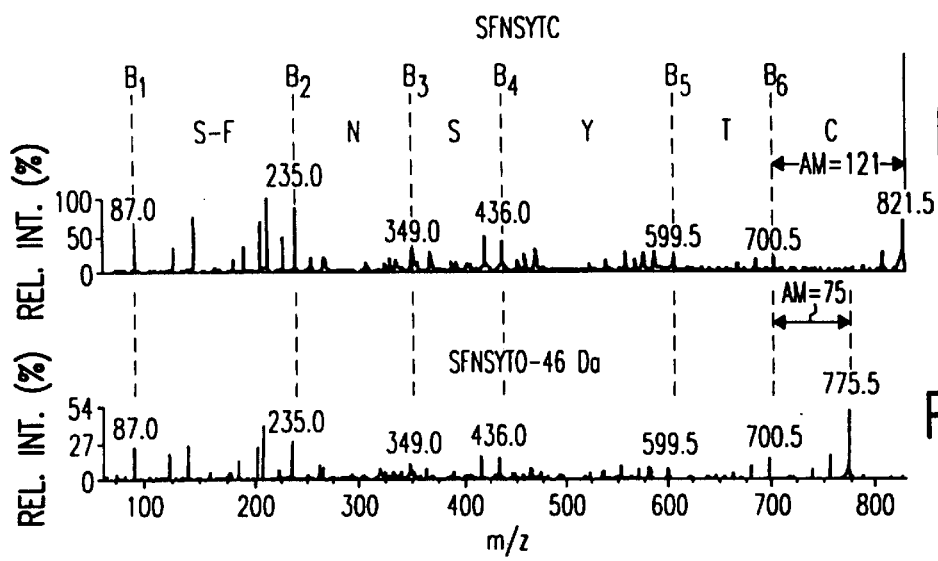
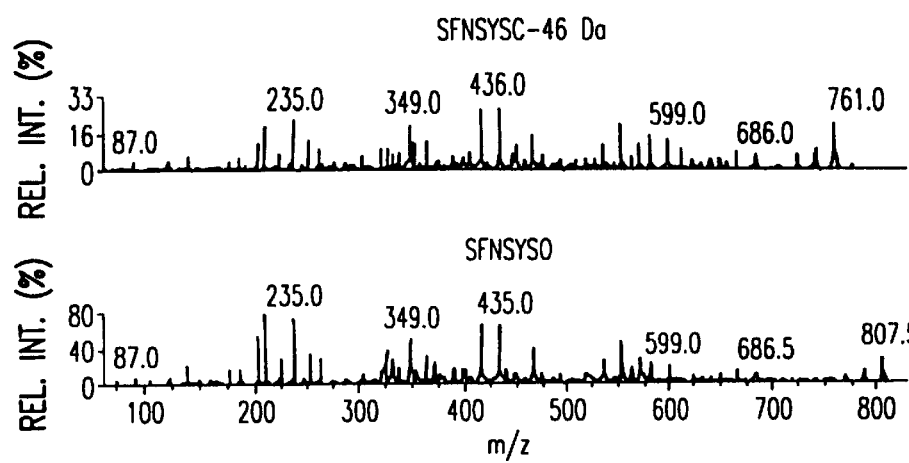

SEQUENCE LISTING (1) GENERAL INFORMATION:

(iii) NUMBER OF SEQUENCES: 70

(2) INFORMATION FOR SEQ ID NO:1:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:1:

Xaa Xaa Xaa Xaa Xaa Xaa Cys
1               5

(2) INFORMATION FOR SEQ ID NO:2:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:2:

Ser Phe Asn Ser Tyr Cys Cys
1               5

(2) INFORMATION FOR SEQ ID NO:3:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:3:

Ser Phe Asn Ser Phe Cys Cys
1               5

(2) INFORMATION FOR SEQ ID NO:4:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:4:

Ser Phe Asn Ser Trp Cys Cys
1               5

(2) INFORMATION FOR SEQ ID NO:5:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:5:

Ser Phe Asn Ser Tyr Ser Cys
1               5

(2) INFORMATION FOR SEQ ID NO:6:

(i) SEQUENCE CHARACTERISTICS:
    (A) LENGTH: 7 amino acids
    (B) TYPE: amino acid
    (C) STRANDEDNESS: single
    (D) TOPOLOGY: Not Relevant (ii) MOLECULE TYPE: peptide (xi) SEQUENCE DESCRIPTION: SEQ ID NO:6:

Xaa Phe Asn Ser Tyr Cys Cys
1               5

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:7:

Ser Xaa Asn Ser Tyr Cys Cys
1               5

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:8:

Ser Phe Xaa Ser Tyr Cys Cys
1               5

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:9:

Ser Phe Asn Xaa Tyr Cys Cys
1               5

(2) INFORMATION FOR SEQ ID NO:10:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:10:

Ser Phe Asn Ser Xaa Cys Cys
1               5

(2) INFORMATION FOR SEQ ID NO:11:

```
       (i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:11:

Ser Phe Asn Ser Tyr Xaa Cys
1               5

(2) INFORMATION FOR SEQ ID NO:12:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:12:

Ser Phe Asn Ser Xaa Xaa Cys
1               5

(2) INFORMATION FOR SEQ ID NO:13:

(i) SEQUENCE CHARACTERISTICS:
            (A) LENGTH: 148 amino acids
            (B) TYPE: amino acid
            (C) STRANDEDNESS: single
            (D) TOPOLOGY: Not Relevant (ii) MOLECULE TYPE: protein (xi) SEQUENCE DESCRIPTION: SEQ ID NO:13:

Ser Leu Lys Gly Asp Asp Ile Ile Lys Gly Leu Tyr Asp Leu Trp Lys
1               5                  10                  15

Ile Thr Lys Pro Asn Thr Leu Leu Ser Ile Gly Leu Ile Phe Ser
                20                  25                  30

Leu Ile Gly Thr Ser Phe Ser Leu Tyr Ile Pro Leu Ile Ile Arg Asn
            35                  40                  45

Ala Leu Asn Lys Ser Ser Leu Ser Thr Asp Lys Ile Val Ile Ile Ile
        50                  55                  60

Ile Cys Phe Gly Leu Thr Leu Ile Phe Ser Gly Val Ser Thr Tyr Ile
65                  70                  75                  80

Leu Gly Tyr Ile Gly Gln Lys Ile Ile Gln Asn Ile Arg Ser Val Thr
                85                  90                  95

Trp Asn Lys Val Ile Lys Leu Pro Tyr Ser Phe His Leu Lys Asn Ser
                100                 105                 110

Ala Ser Asn Leu Thr Ser Arg Leu Val Asn Asp Thr Met Asn Ile Thr
            115                 120                 125

Arg Val Phe Ser Val Glu Phe Ile Phe Ser Tyr Ser Ile Thr Asn Ile
    130                 135                 140

Phe Ile Tyr Asn
145

(2) INFORMATION FOR SEQ ID NO:14:

(i) SEQUENCE CHARACTERISTICS:
            (A) LENGTH: 52 amino acids
            (B) TYPE: amino acid
            (C) STRANDEDNESS: single
            (D) TOPOLOGY: Not Relevant
```

(ii) MOLECULE TYPE: protein (xi) SEQUENCE DESCRIPTION: SEQ ID NO:14:

Met Glu Ala Val Lys Glu Lys Asn Asp Leu Phe Asn Leu Asp Val Lys
1               5                   10                  15

Val Asn Ala Lys Glu Ser Asn Asp Ser Gly Ala Glu Pro Arg Ile Ala
            20                  25                  30

Ser Lys Phe Ile Cys Thr Pro Gly Cys Ala Lys Thr Gly Ser Phe Asn
        35                  40                  45

Ser Tyr Cys Cys
        50

(2) INFORMATION FOR SEQ ID NO:15:

(i) SEQUENCE CHARACTERISTICS:
        (A) LENGTH: 990 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:15:

Gly Glu Ile Glu Leu Asp Asn Ile Phe Val Pro Ser Asn Ile Tyr Met
1               5                   10                  15

Val Arg Thr Pro Ile Phe Ser Ile Glu Leu Tyr Asn Gln Phe Leu Lys
            20                  25                  30

Ser Asp Asn Ile Asp Tyr Asp Leu Ile Leu Gln Asn Asp Ile Phe Lys
        35                  40                  45

Glu Ser Ile Met Thr Thr Thr Tyr Asn Leu Tyr Gln Ser Ile Gly Lys
    50                  55                  60

Ile Asp Trp Glu Lys Asp Asn Lys Lys Thr Arg Asn Val Lys Glu Ser
65              70                  75                  80

Leu Leu Lys Tyr Leu Ile Arg Met Ser Thr Arg Ser Thr Pro Tyr Gly
                85                  90                  95

Met Leu Ser Gly Val Ala Leu Gly Glu Phe Ser Glu Asn Asn Asn Ile
            100                 105                 110

Lys Ile Lys Asp Ser Ser Phe His Lys Lys Asp Val Lys Ile Asp Gly
        115                 120                 125

Gln Trp Leu Tyr Lys Leu Val His Tyr Leu Glu Ser Asp Tyr Thr Tyr
    130                 135                 140

Tyr Lys Asp Ser Phe Val Ile Trp Asn Gln Gln Asn Tyr Ile Tyr Asn
145                 150                 155                 160

Asn Arg Leu Tyr Leu Asp Asn Asn Ser Ser Ile Thr Glu Asn Lys Arg
                165                 170                 175

Asn Asp Val Leu Ser Val Lys Tyr Asn Ser Ile Leu Val Phe Ile His
            180                 185                 190

Glu Asn Ser Lys Lys Asn Ile Thr Tyr Glu Glu Leu Val Gln Leu Ile
        195                 200                 205

Ser Ser Lys Tyr Ser Ile Glu Asn Lys Glu Glu Val Lys Val Phe Val
    210                 215                 220

Gln Glu Leu Ile Asn Lys Glu Ile Phe Ser Asp Leu Arg Pro Thr
225                 230                 235                 240

Leu Glu Asn Lys Asn Pro Leu Asp Tyr Ile Ile Asn Ser Leu Asn Pro
                245                 250                 255

Lys Asn Ser Leu Val Gly Thr Leu Ile Asn Ile Ser Asn Glu Ile Thr
            260                 265                 270

```
Lys Tyr Ser Lys Met Pro Leu Gly Lys Gly Glu Tyr Lys Tyr Leu Asp
        275                 280                 285

Ile Val Asn Leu Met Ser Gln Leu Phe Val Ser Lys Asn Tyr Leu Gln
        290                 295                 300

Ile Asp Thr Tyr Ile Asp Tyr Ser Arg Asn Glu Leu Lys Gln Ser Leu
305                 310                 315                 320

Ala Asp Asn Ile Ser Glu Ala Ala Tyr Ile Leu Trp Leu Leu Ser Pro
                325                 330                 335

Asn His Phe Gly Thr Lys Thr Ile Arg Asn Tyr His Glu Phe Phe Met
            340                 345                 350

Asp Lys Tyr Gly Phe Glu Gln Leu Val Asn Leu Lys Gln Leu Leu Ser
        355                 360                 365

Asp Ile Asn Gly Phe Gly Tyr Pro Lys Lys Asp Ser Tyr Ser Phe Ser
        370                 375                 380

Asn Asn Ile Ala Phe Leu Lys Glu Lys Tyr Leu Leu Ala Ile Gln Asn
385                 390                 395                 400

Asn Ser His Ile Glu Ile Thr Glu Asn Asp Val Lys Asn Leu Glu Lys
                405                 410                 415

Asn Asn Thr Val Ser Lys Ile Asn Ala Pro Val Ser Thr Glu Ile Tyr
            420                 425                 430

Ser Glu Ile Tyr Phe Gly Asn Ser Ile Lys Gly Tyr Glu Asp Phe Ala
        435                 440                 445

Val Ile Ser Pro Ile Leu Gly Ser Phe Asn Ala Gly Ala Thr Phe Gly
        450                 455                 460

Arg Phe Thr Gly Asn Phe Asn Ile Lys Lys Asn Gln Leu Gln Lys
465                 470                 475                 480

Glu Ile Val His His Tyr Asn Asn Tyr Met Asn Glu Asn Asp Leu Glu
                485                 490                 495

Ile Ser Gln Leu Asn Glu Ala Pro Leu Asn Ser Arg Asn Val Asn Ile
                500                 505                 510

Leu Asn Asn Asn Arg Ile Tyr Asn Thr Cys Leu Asn Leu Asn Leu Pro
            515                 520                 525

Lys Ser Asp Ile Asp Ile Asn Asp Ile Phe Ile Gly Ala Thr Phe Asn
        530                 535                 540

Lys Leu Tyr Leu Tyr Ser Glu Lys His Asp Ser Arg Ile Val Phe Val
545                 550                 555                 560

Ser Asn Ser Met Phe Asn Tyr Glu Phe Gly Ser Glu Leu Tyr Lys Phe
                565                 570                 575

Leu Arg Glu Ile Ser Phe Glu Lys Thr Lys Phe Ile Gln Pro Ile Thr
            580                 585                 590

Glu Glu Gly Ile Asp Ser Leu Pro Phe Cys Pro Arg Ile Ile Tyr Lys
        595                 600                 605

Asn Ile Ile Leu Lys Pro Ala Thr Trp Lys Ile Asn Ser Glu Met Phe
        610                 615                 620

Ser Glu Thr Glu Asn Trp Leu Asn Arg Phe Ala Thr Ile Arg Glu Lys
625                 630                 635                 640

Trp His Ile Pro Lys Asp Val Ile Ile Ala Phe Gly Asp Asn Arg Leu
                645                 650                 655

Leu Leu Asn Leu Leu Asn Asp Lys His Leu Ile Ile Leu Lys Lys Glu
            660                 665                 670

Leu Lys Lys His Gly Arg Ile Arg Ile Leu Glu Ser Phe Ile Asn Glu
        675                 680                 685

Ser Asn Asn Glu Arg Met Leu Glu Ile Val Thr Pro Leu Tyr Lys Lys
```

```
                690                 695                 700
Thr Ser Leu Lys Glu Gln Ser Phe Ile Ile Pro Lys Asn Arg Asn Lys
705                 710                 715                 720

His Phe Asn Asn Leu Lys Asp Trp Phe Ser Ile His Leu Ser Ile Pro
                725                 730                 735

Lys Thr Tyr Gln Asp Asn Phe Ile Gln Asp Tyr Leu Leu Pro Phe Ile
                740                 745                 750

Thr Glu Leu Lys Val Asn Asn Phe Ile Asn Lys Phe Tyr Ile Lys
            755                 760                 765

Phe Lys Glu Asp Glu Asp Phe Ile Lys Leu Arg Leu Leu Arg Glu Asp
770                 775                 780

Glu Asp Tyr Ser Gln Ile Tyr Ser Phe Ile Lys Asn Trp Lys Asp Tyr
785                 790                 795                 800

Cys Leu Leu Asn Ser Glu Leu Tyr Asp Tyr Ser Ile Val Asp Tyr Val
                805                 810                 815

Pro Glu Val Tyr Arg Tyr Gly Gly Pro His Val Ile Glu Asp Ile Glu
                820                 825                 830

Asn Phe Phe Met Tyr Asp Ser Leu Leu Ser Ile Asn Ile Ile Gln Ser
                835                 840                 845

Glu Phe Lys Ile Pro Lys Glu Phe Ile Val Ala Ile Ser Ile Asp Phe
850                 855                 860

Leu Leu Asp Tyr Leu Glu Ile Asn Lys Ser Glu Lys Glu Ile Leu
865                 870                 875                 880

Ile Asn Asn Ala Glu Asp Leu Tyr Arg Ser Asn Asp Ile Arg Glu Tyr
                885                 890                 895

Lys Asn Leu Leu Ala Lys Leu Thr Asn Pro Lys Asn Asp Tyr Glu Ile
                900                 905                 910

Leu Lys Lys Glu Phe Pro Asn Leu His Glu Phe Leu Phe Asn Lys Ile
                915                 920                 925

Ser Ile Leu Glu Asn Leu Lys Lys Thr Leu Gln Lys Ser Leu Tyr Thr
                930                 935                 940

Ser Arg Ser Arg Ile Ile Gly Ser Phe Ile His Met Arg Cys Asn Arg
945                 950                 955                 960

Ile Phe Gly Ile Asn Pro Glu Lys Glu Lys Phe Val Leu Ser Ile Phe
                965                 970                 975

Asn Glu Ile Thr Lys Thr Lys Lys Tyr Trp Asp Gly Cys Asp
                980                 985                 990

(2) INFORMATION FOR SEQ ID NO:16:

(i) SEQUENCE CHARACTERISTICS:
          (A) LENGTH: 78 amino acids
          (B) TYPE: amino acid
          (C) STRANDEDNESS: single
          (D) TOPOLOGY: Not Relevant (ii) MOLECULE TYPE: peptide (xi) SEQUENCE DESCRIPTION: SEQ ID NO:16:

Ala Pro Ala Leu His Ser Gln Gly Tyr Thr Gly Ser Asn Val Lys Val
1               5                   10                  15

Ala Val Ile Asp Ser Gly Ile Asp Ser Ser His Pro Asp Leu Asn Val
                20                  25                  30

Arg Gly Gly Ala Ser Phe Val Pro Ser Glu Thr Asn Pro Tyr Gln Asp
            35                  40                  45

Gly Ser Ser His Gly Thr His Val Ala Gly Thr Ile Ala Ala Leu Asn
        50                  55                  60
```

```
Asn Ser Ile Gly Val Leu Gly Val Ser Pro Ser Ala Ser Leu
 65                  70                  75
```

(2) INFORMATION FOR SEQ ID NO:17:

(i) SEQUENCE CHARACTERISTICS:
  (A) LENGTH: 41 amino acids
  (B) TYPE: amino acid
  (C) STRANDEDNESS: single
  (D) TOPOLOGY: Not Relevant (ii) MOLECULE TYPE: peptide (xi) SEQUENCE DESCRIPTION: SEQ ID NO:17:

```
Met Ala Pro Gly Val Ser Ile Gln Ser Thr Leu Pro Gly Gly Thr Tyr
 1               5                  10                  15

Gly Ala Tyr Asn Gly Thr Ser Met Ala Thr Pro His Val Ala Gly Ala
                20                  25                  30

Ala Ala Leu Ile Leu Ser Lys His Pro
            35                  40
```

(2) INFORMATION FOR SEQ ID NO:18:

(i) SEQUENCE CHARACTERISTICS:
  (A) LENGTH: 8700 base pairs
  (B) TYPE: nucleic acid
  (C) STRANDEDNESS: both
  (D) TOPOLOGY: both (ii) MOLECULE TYPE: cDNA (xi) SEQUENCE DESCRIPTION: SEQ ID NO:18:

```
AGATCTTGTG TTATATAACT AAACAAATTT CTCCATTCGT ATTTAGAAAA TTGACTTTTA    60

TCAAGTTTAT CCAAATATAT ATTTCCAGTA TATTCTGTAT TTAACCCAGC TAATATATTT   120

AATAATGTAC TTTTTCCACA CCCACTTTCA CCTATAATAT TGTAGATATA ACCTTTATGA   180

AGATCCAAAC TTATAGAATT TATTATTTGT TTATTGTCTT TTGTGAAGTT CAAATCATTT   240

ATTTCCATTT TTTGAACAAA GTTATTGTAA GTTGTTTTAA TAGTTAATAC CTCTTCTGGT   300

TCTTTATTTA TTTTTAAAAT TCTATCTGAA GATCCAATTG CTCGTTGTAC TTCCGTCCAA   360

TAAGATGTAA TAGATACTAT TGGATTAATA ATTTGAAATA AATATAAAAC ATAAGCAAAC   420

ATATCTCCGC TTTTCATCAT ATTATTTTCC ATTAAGTAAT AACCCAAAAA TAAAATACCA   480

AAAATGTTAA TAAATAGAAT TAAGTTCATA ATTGGTTCGA AAAAAGATAA TACTTTGATC   540

TTATGTAACT CTATATCGAA TATATTTTTT AATAGGGTAT AGTTTTTTAT TTTTTCGATA   600

TTATATGTAC TTAAAGTTTT TATTAATTTT ATTGTAGATA ATCTATTACT ATAATAAGAA   660

GATAATTTAG CAGTAGCTTC TTGAGATTTA CTTGATACTC TTTTCATTAT ATTTCCTATA   720

GGTAGTATTA CAATTATCAA TATAGGTAAT GTACACACTA AATATAATGT CAAGGTTTTG   780

TTAATTATAT ATAAAAATAT TAGTGATACT ATAACTGAAA ATAAATTCTA CAGAAAAAAC   840

TCTAGTTATG TTCATAGTAT CGTTTACTAA CCTACTAGTT AAGTTACTTG CTGAGTTTTT   900

TAAGTGAAAA CTATAAGGTA ACTTTATCAC TTTATTCCAT GTAACACTTC TAATGTTTTG   960

TATTATTTTT TGACCTATAT ATCCAAGAAT ATAAGTAGAA ACACCAGAAA ATATTAAAGT  1020

CAGACCAAAA CATATAATAA TGATTACAAT TTTATCTGTT GATAAGCTAG ATTTGTTTAA  1080

GGCATTTCTA ATTATTAAAG GAATGTATAA TGAAAAACTA GTTCCAATCA ACTAAATAT   1140

TAGTCCAATA CTTAAAAGTA GAGTGTTAGG TTTGGTTATT TTCCATAAAT CATATAGACC  1200

TTTGATAATA TCATCACCTT TTAAACTTTA TATCATTAAT ATAATGTTTA GGAAAAGTAG  1260
```

```
AAGAAAATTA CACTTTTGTA ATTTTCTGAA TATACATAGT ATTTATTTTG GGGGAGTACT      1320

AAAATAATAA TTGAAAAGGG TTTTATAATC CTTTTTAATA AATTTTTAGG AGTGTTTAAA      1380

ATGGAAGCAG TAAAAGAAAA AAATGATCTT TTTAATCTTG ATGTTAAAGT TAATGCAAAA      1440

GAATCTAACG ATTCAGGAGC TGAACCAAGA ATTGCTAGTA AATTTATATG TACTCCTGGA      1500

TGTGCAAAAA CAGGTAGTTT TAACAGTTAT TGTTGTTAAT TCAGAAGAAT TAGATTGGCA      1560

GGGCTTCAAT AGAGGCTCTG TCTTAATTTT GAGGTGAAAT AGAATTGGAT AATATATTTG      1620

TTCCATCGAA TATATATATG GTAAGAACTC CTATATTTTC AATTGAATTA TATAATCAAT      1680

TCTTAAAATC TGACAATATA GATTATGACT TAATTTTACA AAACGATATT TTTAAAGAAT      1740

CTATAATGAC AACGACATAT AATCTTTATC AAAGTATTGG CAAAATAGAC TGGGAAAAGG      1800

ATAATAAAAA AACCAGAAAT GTAAAGAAAA GTTATTAAA ATATCTCATA AGAATGAGTA      1860

CTAGAAGTAC ACCATATGGA ATGCTAAGCG GTGTAGCTTT AGGGGAATTT AGTGAAAATA      1920

ATAATATTAA AATTAAGGAC TCTTCGTTTC ATAAAAAAGA TGTAAAAATA GATGGGCAAT      1980

GGTTATATAA ATTAGTCCAT TATTTAGAAA GCGATTACAC ATATTATAAA GACAGTTTTG      2040

TCATATGGAA TCAACAAAAT TATATTTATA ACAATCGTTT ATATTTAGAT AATAATTCAT      2100

CAATCACTGA AAATAAAAGA AATGATGTAT TATCTGTCAA ATACAATTCT ATATTAGTGT      2160

TTATACATGA GAATTCTAAA AAAAATATTA CTTATGAAGA ACTTGTACAA TTGATATCTA      2220

GTAAGTACAG TATAGAAAAT AAAGAAGAAG TAAAAGTATT TGTTCAAGAA CTCATAAATA      2280

AAGAAATTAT ATTTTCTGAT TGAGACCTA CATTAGAGAA TAAAAATCCT TTAGATTACA       2340

TTATTAATAG TTTAAATCCA AAAAATAGTT TAGTTGGAAC ACTTATTAAT ATTTCTAATG      2400

AAATTACAAA ATATTCTAAA ATGCCTTTAG GAAAAGGAGA ATATAAATAT TTAGATATTG      2460

TTAATTTAAT GTCACAATTA TTTGTTTCTA AAAACTATTT GCAAATAGAT ACCTATATAG      2520

ATTATTCAAG AAATGAATTA AAACAAAGTT TAGCTGATAA TATTAGTGAA GCAGCATATA      2580

TTCTCTGGTT ATTATCTCCT AATCATTTTG GTACAAAAAC TATTAGGAAT TATCACGAAT      2640

TTTTTATGGA TAAATATGGA TTTGAACAAC TAGTAAATTT AAAGCAATTG CTCTCAGATA      2700

TAAATGGATT TGGCTATCCC AAAAAAGACA GTTATAGTTT TTCTAATAAC ATTGCATTTT      2760

TAAAAGAAAA GTATTTGCTT GCAATTCAAA ATAACAGCCA TATTGAAATA ACAGAAAACG      2820

ACGTTAAAAA TTTAGAAAAG AATAATACAG TTTCTAAAAT CAATGCGCCT GTTTCAACTG      2880

AAATATATAG TGAGATATAT TTTGGAAATT CAATAAAAGG TTATGAGGAT TTTGCCGTGA      2940

TAAGTCCAAT ATTAGGATCT TTTAATGCCG GTGCAACTTT TGGAAGGTTT ACGGGAAATT      3000

TCAATATAAA GAAAAAAAAT CAATTACAAA AAGAAATAGT GCATCATTAC AATAATTACA      3060

TGAATGAAAA TGGTTTAGAA ATAAGCCAAT TAAATGAAGG TCCTCTTAAC TCAAGAAATG      3120

TAAATATTTT GAATAATAAT AGAATATATA ATACTTGTTT AAATTTAAAT TTACCTAAAA      3180

GTGATATAGA TATAAATGAC ATATTTATTG GAGCTACATT TAACAAACTT TATCTATATT      3240

CTGAAAAACA TGATTCAAGA ATTGTATTCG TATCTAATTC AATGTTTAAT TATGAGTTTG      3300

GATCTGAATT ATACAAATTT TTAAGAGAAA TTTCATTTGA AAAACAAAA TTTATACAAC       3360

CTATAACTGA AGAAGGCATT GACTCATTAC CTTTTTGTCC AAGAATTATT TATAAAAATA      3420

TTATTTTAAA ACCAGCTACT TGGAAAATAA ATTCAGAAAT GTTTTCTGAA ACTGAAAATT      3480

GGTTAAAATAG GTTCGCAACT ATTAGAGAAA ATGGCATAT TCCAAAAGAT GTAATTATTG      3540

CTTTTGGAGA TAATCGATTG CTATTAAATT TATTAAATGA CAAGCATCTC ATTATACTAA      3600

AAAAAGAACT AAAAAAACAT GGTAGGATTC GAATATTAGA AAGCTTTATC AATGAATCTA      3660
```

```
ATAATGAGAG AATGTTAGAA ATTGTTACGC CATTATATAA AAAAACTAGT TTAAAAGAAC    3720

AATCTTTCAT TATACCTAAA AATAGAAATA AGCACTTCAA TAATCTTAAA GATTGGTTTT    3780

CAATTCATTT AAGTATTCCT AAAACATACC AAGATAATTT TATTCAAGAT TATCTATTAC    3840

CATTTATAAC GGAATTAAAA GTTAATAATT TTATTAATAA ATTTTTTTAC ATAAAATTTA    3900

AAGAAGATGA AGATTTTATA AAATTAAGAT TATTAAGAGA AGATGAAGAT TATTCTCAAA    3960

TTTATTCTTT CATAAAAAAT TGGAAAGATT ATTGCTTATT AAATAGTGAA TTATATGACT    4020

ATTCTATAGT TGATTATGTT CCTGAAGTAT ATAGATATGG TGGTCCACAC GTAATTGAAG    4080

ATATTGAGAA TTTTTTTATG TATGATAGTC TATTATCAAT AAATATAATA CAATCAGAGT    4140

TCAAAATTCC AAAAGAATTT ATCGTTGCTA TATCAATAGA TTTTTTATTA GATTATTTAG    4200

AAATTAATAA AAGTGAGAAA GAAGAAATTT TAATTAATAA TGCGGAAGAT TTATATCGTA    4260

GTAATGACAT AAGAGAATAT AAAAATTTAT TAGCTAAACT TACCAATCCT AAAAATGACT    4320

ATGAAATTTT AAAAAAGAA TTTCCGAATC TTCATGAATT TCTATTTAAT AAAATTAGTA    4380

TTTTAGAAAA TCTTAAAAAG ACACTACAAA AAAGCTTATA TACTTCACGT TCTAGGATAA    4440

TTGGCAGTTT TATACACATG CGTTGTAATA GAATATTCGG TATTAATCCT GAAAAGAAA    4500

AATTTGTTTT ATCTATTTTT AATGAAATTA CAAAAACTAA AAAATATTGG GATGGTTGTG    4560

ATTAATATTA ATAACATTAA AAAAATTTTA GAAAATAAAA TCACCTTTTT GTCTGACATT    4620

GAAAAAGCTA CATATATTAT AGAAAATCAA AGTGAGTATT GGGATCCTTA TACTCTATCT    4680

CATGGTTATC CAGGTATAAT ACTTTTTTTA AGCGCATCAG AAAAAGTATT TCATAAAGAT    4740

TTAGAAAAAG TAATACATCA ATATATTAGA AAACTAGGCC CTTATTTAGA AAGTGGTATT    4800

GATGGATTTT CACTTTTTAG TGGTCTTTCC GGAATTGGAT TTGCGCTAGA CATTGCGTCT    4860

GATAAACAGT ACTCTTATCA AAGTATCTTA GAACAAATTG ATAATTTACT TGTTCAATAT    4920

GTTTTTGATT TTTAAATAA CGATGCATTG GAAGTAACCC CTACTAACTA TGATATAATA    4980

CAAGGATTTT CTGGTATAGG AAGGTACTTG TTAAATAGAA TATCGTATAA TTATAATGCA    5040

AAAAAAGCAT TAAAGCATAT ACTTAATTAC TTCAAAACAA TTCATTACTC TAAAGACAAT    5100

TGGTTAGTTT CAAATGAACA TCAATTTTTA GATATAGATA AGCAAAATTT TCCGTCAGGA    5160

AATATAAATT TAGGATTAGC GCATGGTATT TTAGGTCCTC TATCATTAAC AGCTTTGAGT    5220

AAAATGAATG GGATTGAAAT CGAAGGCCAT GAAGAGTTTT TACAAGACTT CACTTCATTT    5280

TTGCTCAAAC CTGAATTCAA AAATAATAAT GAATGGTTCG ATCGCTATGA TATATTAGAA    5340

AATTATATAC CTAATTATTC CGTCAGAAAC GGTTGGTGTT ACGGTGATAC AGGGATTATG    5400

AATACATTAC TTTTGTCTGG TAAAGCCTTA AATAATGAAG GCTTAATTAA AATGTCTAAA    5460

AATATTTTAA TTAACATAAT AGATAAGAAT AATGATGATT TAATCAGTCC AACCTTCTGT    5520

CACGGACTAG CATCGCACTT AACCATTATT CATCAAGCGA ATAAATTCTT TAATCTATCT    5580

CAAGTAAGCA CATATATCGA TACCATTGTC AGAAAAATTA TTAGTCATTA TTCTGAAGAA    5640

AGTAGTTTTA TGTTCCAAGA CATAGAGTAC TCATACGGAC AAAAAATTTA TAAAAACAAA    5700

GTGGGAATTC TAGAGGGTGA ATTAGGTGTT CTTTTAGCTT TACTAGATTA TATTGATACA    5760

CAAAACCAAT CAAGGAAAAA TTGGAAAAAT ATGTTTTTAA TAACATAATA GGAGGAATAA    5820

GATATGTATG GAAAATTATT GATATGCGCT ACAGCATCGA TAAATGTAAT TAATATTAAT    5880

CACTACATAG TTGAGTTAAA GCAACATTTT GATGAAGTTA ATATATTATT TAGTCCTAGT    5940

AGTAAAAATT TTATAAATAC TGATGTTCTC AAGTTATTTT GTGATAACTT GTACGATGAA    6000

ATTAAAGATC CTCTTTTAAA TCATATCAAT ATTGTAGAAA ATCATGAATA TATTTTAGTA    6060
```

| | |
|---|---|
| TTACCTGCAT CAGCAAATAC TATTAATAAA ATAGCTAATG GTATATGTGA TAATCTTTTA | 6120 |
| ACTACTGTAT GTTTAACCGG ATATCAAAAA TTATTTATAT TTCCAAATAT GAACATAAGA | 6180 |
| ATGTGGGAA ATCCATTTTT ACAAAAAAAT ATTGATTAC TTAAAAATAA TGATGTGAAA | 6240 |
| GTGTATTCCC CTGATATGAA TAAATCATTC GAAATATCTA GTGGCCGTTA CAAAAACAAT | 6300 |
| ATCACAATGC CTAATATTGA AAATGTACTA AATTTTGTAT TAAATAACGA AAAAAGACCT | 6360 |
| TTGGATTAAC AAAGGTCTTT TCTAATTAAA ATTTTATATC CGAGTTTACG TTCATTAATA | 6420 |
| ATTTCTATCT CTTTACAATT TTTTAAACTA TCCCTTAATC GATGGATATA TACATTTATT | 6480 |
| GTATTAGAAT CAACAAAGTC TTCTGTATCC CACACTCCCT TTTTTAATTC CTCTTTTGAT | 6540 |
| ACATATCTTC CAAGATTAAT ATATAAGCAC CGTAGAATTT TTAATTCTAT ATTAGAAAGA | 6600 |
| TTAACTAAGT AATTATTAAA CACAAATTGA TGGTTTTCAA AGTCTATAAA ATCATCATTA | 6660 |
| ACATATTTAA TATACTTTTT TATTTCATTT AAAATTCTAC ATAATATTAA ACTTTTGCTT | 6720 |
| TCATTATTTT TTATAATATA TAAATCTATG CCTAAACTAT AAAAATAACA CTTCCTACTA | 6780 |
| TAGCTAGTAT TACCTGTTAT TATAACTATT GGAATTTTTC CTATAAATTC TTTTAAAAAC | 6840 |
| GTATAATACT CATCAAACTT TTCATACACA ATTATAAAAT TTGGGTCTAT ATTTGAAGAA | 6900 |
| TTAATTGTAA TTCTTCTATC TAATTCTAAA ATACTTTCAA TAAGAATAGA ATCTACCTCA | 6960 |
| CCGACAATAT TAATAGAAAT CATTTTATTC CCTTCATTCT TTAAGTAATT TGTATACGTC | 7020 |
| TAGTTTTCCA TTACCATAAT GTTTTTTATC CATATATTTT TCTTTTTCTA TCCCTTTTTT | 7080 |
| CTTAAATAAC TCTATAGCTG TTTCGGGTTG GTCTTTTAAT TGATACTTAT CAATTTCTAG | 7140 |
| TGCTAAAGCT CCAGAAACCT TGGGTGCAGC AAGTGATGTC CCTGATTGAT ATATGTATCT | 7200 |
| TCCATTAGAA GAAGTACTTA AAACACTTTG TTTTTGCATA TATCCTTTTT CTAACCAAGC | 7260 |
| ATCTTTTCCA TACTTATCTA AAAGTTTATA AGAACCTCCT ATCGTCATTA AATCTATAAA | 7320 |
| ATTATTTCCA TAATTAGAAA ACTCAGAAAT ATAATCATTA TCATCGATGG ATCCTACAGT | 7380 |
| CATAACATTA TTTAGATTTG CTGGGCTATC ATATACCTTT TTTGATGTTT TAGAATTTAG | 7440 |
| ATTTCTTTTT TTATTTATTT CTTTTACTTT TTTTACATTG ATACCGTCAT TACCCACAGC | 7500 |
| TGCAACAACA ATACTACCTT TTTTTTGAGC ATAGTTTATA GCTTTCTGTA GTGCATCGTA | 7560 |
| ATCAACTTTT TCATCATCTC TTAATTTTTT TTTATTTTGA TTATCTTTAA TTAAATAATT | 7620 |
| TCCTAAACTA ACGTTGATTA CATCATTGTC ATCATTTGCT GCATCAATAA TTCCTTTAGA | 7680 |
| TACCCAAAGC ATTTCACTTT TCTTTGAGCC AAATACTCGG TATACATTCA TCTCTACTCC | 7740 |
| AGGGTTTACA CCTTTTAAAT TACCGTTTGC TCCTATTTGT CCTGCTACTA ATGTACCATG | 7800 |
| ATTCAATTTA TCTTCTTCAA AATTTTTATT TCCTGATTCA TCGTTTTCGC TACCTCTAAA | 7860 |
| ACCATTTTTA GGCACTTCAT TAACTATCTT ATTTATACTC TTTAAATCTG TATGACTACT | 7920 |
| ATTCACACCA GAATCTACTA AAGCAACTTT TGCTTTTTTT CTATCTGGAC TTAGCTTATA | 7980 |
| ACTTTTACCT TCATTTGTTA TTTTTCGCAT ATCCCATTGT CTGTCAAATA AATCATGGCT | 8040 |
| GCCATTTTTT TTATTATTTA AATTTTTTCC TGTCTTTACA GATTTTTCAA CTACACAAGT | 8100 |
| GGAACAGGTA GGATTTACAA ACTTGACGTT TTTATTACTC TTTATTAGTG AATTTAATTT | 8160 |
| TGATTGCTA GTTTTAATTT GTGCTGTATG TAGTTCAGGA ATTTTATAAG TTAACTCGAT | 8220 |
| ATTTTTTTGT TTAATGGATT CTTTAAAAGT TTTTGCATTA TCATATTCAA CACTATAATA | 8280 |
| ACTTAATTCT TCATTTAGTG AACTTCCAAA AGCATACTCA TTTTGCAAAA AAACTAATGA | 8340 |
| CAATATTAAA AAAACAATGA AAAATTTAAA TTTGTTCATA TAGCACCTCT AACATATTAT | 8400 |
| TTATATTAAA CATTAATTTA ACACTTATGT TTTTACTTTT TTATTTATAT TATCTTTAAT | 8460 |

```
AATGTTCTGT TGCAAGATGA AAAATACGAG GTATCAAAGT ACCGATACAG CGAGTATTAC      8520

ACTCAATTAA TTAAAAATAA AATATGTTGT GATTAAAATT TATTTTATAA AAGTATGGGC      8580

AATTTATTAT TATTCAAGTT AAAACAAAGA GTCCGGGACA TAAAGTTTCA GCCTCTTCGT      8640

CCTAATTACC AAAAAACTTA CTCCAAAATC CTTTTTTAGA TTGGTTTTTT CTAATTTTTT      8700
```

(2) INFORMATION FOR SEQ ID NO:19:

(i) SEQUENCE CHARACTERISTICS:
        (A) LENGTH: 275 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:19:

```
Asn Leu Phe Ser Val Ile Val Ser Leu Ile Phe Leu Tyr Ile Ile Asn
  1               5                  10                  15

Lys Thr Leu Thr Leu Tyr Leu Val Cys Thr Leu Pro Ile Leu Ile Ile
                 20                  25                  30

Val Ile Leu Pro Ile Gly Asn Ile Met Lys Arg Val Ser Ser Lys Ser
             35                  40                  45

Gln Glu Ala Thr Ala Lys Leu Ser Ser Tyr Tyr Ser Asn Arg Leu Ser
 50                  55                  60

Thr Ile Lys Leu Ile Lys Thr Leu Ser Thr Tyr Asn Ile Glu Lys Ile
 65                  70                  75                  80

Lys Asn Tyr Thr Leu Leu Lys Asn Ile Phe Asp Ile Glu Leu His Lys
                 85                  90                  95

Ile Lys Val Leu Ser Phe Phe Glu Pro Ile Met Asn Leu Ile Leu Phe
            100                 105                 110

Ile Asn Ile Phe Gly Ile Leu Phe Leu Gly Tyr Tyr Leu His Glu Asn
            115                 120                 125

Asn Met Met Lys Ser Gly Asp Met Phe Ala Tyr Val Leu Tyr Leu Glu
130                 135                 140

Gln Ile Ile Asn Pro Ile Val Ser Ile Thr Ser Tyr Trp Thr Glu Val
145                 150                 155                 160

Gln Arg Ala Ile Gly Ser Ser Asp Arg Ile Leu Lys Ile Asn Lys Glu
                165                 170                 175

Pro Glu Glu Val Leu Thr Ile Lys Thr Thr Tyr Asn Asn Phe Val Gln
            180                 185                 190

Lys Met Glu Ile Asn Asp Leu Asn Phe Thr Lys Asp Asn Lys Gln Ile
            195                 200                 205

Ile Asn Ser Ile Ser Leu Asp Leu His Lys Gly Tyr Ile Tyr Asn Ile
210                 215                 220

Ile Gly Glu Ser Gly Cys Gly Lys Ser Thr Leu Leu Asn Ile Leu Ala
225                 230                 235                 240

Gly Leu Asn Thr Glu Tyr Thr Gly Asn Ile Tyr Leu Asp Lys Lys Leu
                245                 250                 255

Asp Ser Gln Phe Ser Lys Tyr Glu Trp Arg Asn Leu Phe Ser Tyr Ile
                260                 265                 270

Thr Gln Asp
275
```

(2) INFORMATION FOR SEQ ID NO:20:

(i) SEQUENCE CHARACTERISTICS:

(A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:20:

Ser Phe Xaa Xaa Tyr Cys Cys
1               5

(2) INFORMATION FOR SEQ ID NO:21:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:21:

Ser Xaa Xaa Xaa Tyr Cys Cys
1               5

(2) INFORMATION FOR SEQ ID NO:22:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:22:

Xaa Xaa Xaa Xaa Tyr Cys Cys
1               5

(2) INFORMATION FOR SEQ ID NO:23:

(i) SEQUENCE CHARACTERISTICS:
            (A) LENGTH: 455 amino acids
            (B) TYPE: amino acid
            (C) STRANDEDNESS: single
            (D) TOPOLOGY: Not Relevant (ii) MOLECULE TYPE: protein (xi) SEQUENCE DESCRIPTION: SEQ ID NO:23:

Leu Ala Val Leu Tyr Thr Cys Val Val Ile Glu Tyr Ser Val Leu Ile
1               5                   10                  15

Leu Lys Lys Lys Asn Leu Phe Tyr Leu Phe Leu Met Lys Leu Gln Lys
                20                  25                  30

Leu Lys Asn Ile Gly Met Val Val Ile Asn Ile Asn Asn Ile Lys Lys
                35                  40                  45

Ile Leu Glu Asn Lys Ile Thr Phe Leu Ser Asp Ile Glu Lys Ala Thr
50                  55                  60

Tyr Ile Ile Glu Asn Gln Ser Glu Tyr Trp Asp Pro Tyr Thr Leu Ser
65                  70                  75                  80

His Gly Tyr Pro Gly Ile Ile Leu Phe Leu Ser Ala Ser Glu Lys Val
                85                  90                  95

Phe His Lys Asp Leu Glu Lys Val Ile His Gln Tyr Ile Arg Lys Leu
                100                 105                 110

Gly Pro Tyr Leu Glu Ser Gly Ile Asp Gly Phe Ser Leu Phe Ser Gly
                115                 120                 125

```
Leu Ser Gly Ile Gly Phe Ala Leu Asp Ile Ala Ser Asp Lys Gln Tyr
    130                 135                 140

Ser Tyr Gln Ser Ile Leu Glu Gln Ile Asp Asn Leu Leu Val Gln Tyr
145                 150                 155                 160

Val Phe Asp Phe Leu Asn Asn Asp Ala Leu Glu Val Thr Pro Thr Asn
                165                 170                 175

Tyr Asp Ile Ile Gln Gly Phe Ser Gly Val Gly Arg Tyr Leu Leu Asn
                180                 185                 190

Arg Ile Ser Tyr Asn Tyr Asn Ala Lys Lys Ala Leu Lys His Ile Leu
            195                 200                 205

Asn Tyr Phe Lys Thr Ile His Tyr Ser Lys Asp Asn Trp Leu Val Ser
    210                 215                 220

Asn Glu His Gln Phe Leu Asp Ile Asp Lys Gln Asn Phe Pro Ser Gly
225                 230                 235                 240

Asn Ile Asn Leu Gly Leu Ala His Gly Ile Leu Gly Pro Leu Ser Leu
                245                 250                 255

Thr Ala Leu Ser Lys Met Asn Gly Ile Glu Ile Glu Gly His Glu Glu
                260                 265                 270

Phe Leu Gln Asp Phe Thr Ser Phe Leu Leu Lys Pro Glu Phe Lys Asn
    275                 280                 285

Asn Asn Glu Trp Phe Asp Arg Tyr Asp Ile Leu Glu Asn Tyr Ile Pro
290                 295                 300

Asn Tyr Ser Val Arg Asn Gly Trp Cys Tyr Gly Asp Thr Gly Ile Met
305                 310                 315                 320

Asn Thr Leu Leu Leu Ser Gly Lys Ala Leu Asn Asn Glu Gly Leu Ile
                325                 330                 335

Lys Met Ser Lys Asn Ile Leu Ile Asn Ile Asp Lys Asn Asn Asp
                340                 345                 350

Asp Leu Ile Ser Pro Thr Phe Cys His Gly Leu Ala Ser His Leu Thr
            355                 360                 365

Ile Ile His Gln Ala Asn Lys Phe Phe Asn Leu Ser Gln Val Ser Thr
    370                 375                 380

Tyr Ile Asp Thr Ile Val Arg Lys Ile Ile Ser His Tyr Ser Glu Glu
385                 390                 395                 400

Ser Ser Phe Met Phe Gln Asp Ile Glu Tyr Ser Tyr Gly Gln Lys Ile
                405                 410                 415

Tyr Lys Asn Lys Val Gly Ile Leu Glu Gly Glu Leu Gly Val Leu Leu
            420                 425                 430

Ala Leu Leu Asp Tyr Ile Asp Thr Gln Asn Gln Ser Arg Lys Asn Trp
        435                 440                 445

Lys Asn Met Phe Leu Ile Thr
450                 455

(2) INFORMATION FOR SEQ ID NO:24:

(i) SEQUENCE CHARACTERISTICS:
        (A) LENGTH: 181 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:24:

Met Tyr Gly Lys Lys Leu Leu Cys Ala Thr Ala Ser Ile Asn Val Ile
1               5                   10                  15
```

Asn Ile Asn His Tyr Ile Val Glu Leu Lys Gln His Phe Asp Glu Val
            20                  25                  30

Asn Ile Leu Phe Ser Pro Ser Lys Asn Phe Ile Asn Thr Asp Val
            35                  40                  45

Leu Lys Leu Phe Cys Asp Asn Leu Tyr Asp Glu Ile Lys Asp Pro Leu
 50                  55                  60

Leu Asn His Ile Asn Ile Val Glu Asn His Glu Tyr Ile Leu Val Leu
 65                  70                  75                  80

Pro Ala Ser Ala Asn Thr Ile Asn Lys Ile Ala Asn Gly Ile Cys Asp
                85                  90                  95

Asn Leu Leu Thr Thr Val Cys Leu Thr Gly Tyr Gln Lys Leu Phe Ile
                100                 105                 110

Phe Pro Asn Met Asn Ile Arg Met Trp Gly Asn Pro Phe Leu Gln Lys
                115                 120                 125

Asn Ile Asp Leu Leu Lys Asn Asn Asp Val Lys Val Tyr Ser Pro Asp
130                 135                 140

Met Asn Lys Ser Phe Glu Ile Ser Ser Gly Arg Tyr Lys Asn Asn Ile
145                 150                 155                 160

Thr Met Pro Asn Ile Glu Asn Val Leu Asn Phe Val Leu Asn Asn Glu
                165                 170                 175

Lys Arg Pro Leu Asp
            180

(2) INFORMATION FOR SEQ ID NO:25:

(i) SEQUENCE CHARACTERISTICS:
        (A) LENGTH: 205 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:25:

Met Ile Ser Ile Asn Ile Val Gly Glu Val Asp Ser Ile Leu Ile Glu
 1               5                  10                  15

Ser Ile Leu Glu Leu Asp Arg Arg Ile Thr Ile Asn Ser Ser Asn Ile
            20                  25                  30

Asp Pro Asn Phe Ile Ile Val Tyr Glu Lys Phe Asp Glu Tyr Tyr Thr
            35                  40                  45

Phe Leu Lys Glu Phe Ile Gly Lys Ile Pro Ile Val Ile Ile Thr Gly
 50                  55                  60

Asn Thr Ser Tyr Ser Arg Lys Cys Tyr Phe Tyr Ser Leu Gly Ile Asp
 65                  70                  75                  80

Leu Tyr Ile Ile Lys Asn Asn Glu Ser Lys Ser Leu Ile Leu Cys Arg
                85                  90                  95

Ile Leu Asn Glu Ile Lys Lys Tyr Ile Lys Tyr Val Asn Asp Asp Phe
                100                 105                 110

Ile Asp Phe Glu Asn His Gln Phe Val Phe Asn Asn Tyr Leu Val Asn
                115                 120                 125

Leu Ser Asn Ile Glu Leu Lys Ile Leu Arg Cys Leu Tyr Ile Asn Leu
130                 135                 140

Gly Arg Tyr Val Ser Lys Glu Leu Lys Lys Gly Val Trp Asp Thr
145                 150                 155                 160

Glu Asp Phe Val Asp Ser Asn Thr Ile Asn Val Tyr Ile His Arg Leu
                165                 170                 175

Arg Asp Ser Leu Lys Asn Cys Lys Glu Ile Glu Ile Ile Asn Glu Arg

```
                180                 185                 190
Lys Leu Gly Tyr Lys Ile Leu Ile Arg Lys Asp Leu Cys
            195                 200                 205

(2) INFORMATION FOR SEQ ID NO:26:

(i) SEQUENCE CHARACTERISTICS:
        (A) LENGTH: 461 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:26:

Met Asn Lys Phe Lys Phe Phe Ile Val Phe Leu Ile Leu Ser Leu Val
1               5                   10                  15

Phe Leu Gln Asn Glu Tyr Ala Phe Gly Ser Ser Leu Asn Glu Glu Leu
            20                  25                  30

Ser Tyr Tyr Ser Val Glu Tyr Asp Asn Ala Lys Thr Phe Lys Glu Ser
        35                  40                  45

Ile Lys Gln Lys Asn Ile Glu Leu Thr Tyr Lys Ile Pro Glu Leu His
    50                  55                  60

Thr Ala Gln Ile Lys Thr Ser Lys Ser Lys Leu Asn Ser Leu Ile Lys
65                  70                  75                  80

Ser Asn Lys Asn Val Lys Phe Val Asn Pro Thr Cys Ser Thr Cys Val
                85                  90                  95

Val Glu Lys Ser Val Lys Thr Gly Lys Asn Leu Asn Asn Lys Lys Asn
            100                 105                 110

Gly Ser His Asp Leu Phe Asp Arg Gln Trp Asp Met Arg Lys Ile Thr
        115                 120                 125

Asn Glu Gly Lys Ser Tyr Lys Leu Ser Pro Asp Arg Lys Lys Ala Lys
    130                 135                 140

Val Ala Leu Val Asp Ser Gly Val Asn Ser Ser His Thr Asp Leu Lys
145                 150                 155                 160

Ser Ile Asn Lys Ile Val Asn Glu Val Pro Lys Asn Gly Phe Arg Gly
                165                 170                 175

Ser Glu Asn Asp Glu Ser Gly Asn Lys Asn Phe Glu Glu Asp Lys Leu
            180                 185                 190

Asn His Gly Thr Leu Val Ala Gly Gln Ile Gly Ala Asn Gly Asn Leu
        195                 200                 205

Lys Gly Val Asn Pro Gly Val Glu Met Asn Val Tyr Arg Val Phe Gly
    210                 215                 220

Ser Lys Lys Ser Glu Met Leu Trp Val Ser Lys Gly Ile Ile Asp Ala
225                 230                 235                 240

Ala Asn Asp Asp Asn Asp Val Ile Asn Val Ser Leu Gly Asn Tyr Leu
                245                 250                 255

Ile Lys Asp Asn Gln Asn Lys Lys Leu Arg Asp Asp Glu Lys Val
            260                 265                 270

Asp Tyr Asp Ala Leu Gln Lys Ala Ile Asn Tyr Ala Gln Lys Lys Gly
        275                 280                 285

Ser Ile Val Val Ala Ala Val Gly Asn Asp Gly Ile Asn Val Lys Lys
    290                 295                 300

Val Lys Glu Ile Asn Lys Lys Arg Asn Leu Asn Ser Lys Thr Ser Lys
305                 310                 315                 320

Lys Val Tyr Asp Ser Pro Ala Asn Leu Asn Asn Val Met Thr Val Gly
                325                 330                 335
```

```
Ser Ile Asp Asp Asn Asp Tyr Ile Ser Glu Phe Ser Asn Tyr Gly Asn
            340                 345                 350

Asn Phe Ile Asp Leu Met Thr Ile Gly Gly Ser Tyr Lys Leu Leu Asp
            355                 360                 365

Lys Tyr Gly Lys Asp Ala Trp Leu Glu Lys Gly Tyr Met Gln Lys Gln
            370                 375                 380

Ser Val Leu Ser Thr Ser Ser Asn Gly Arg Tyr Ile Tyr Gln Ser Gly
385                 390                 395                 400

Thr Ser Leu Ala Ala Pro Lys Val Ser Gly Ala Leu Ala Leu Glu Ile
                405                 410                 415

Asp Lys Tyr Gln Leu Lys Asp Gln Pro Glu Thr Ala Ile Glu Leu Phe
            420                 425                 430

Lys Lys Lys Gly Ile Glu Lys Glu Lys Tyr Met Asp Lys Lys His Tyr
            435                 440                 445

Gly Asn Gly Lys Leu Asp Val Tyr Lys Leu Leu Lys Glu
450                 455                 460
```

(2) INFORMATION FOR SEQ ID NO:27:

(i) SEQUENCE CHARACTERISTICS:
        (A) LENGTH: 4 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:27:

```
Ser Tyr Cys Cys
1
```

(2) INFORMATION FOR SEQ ID NO:28:

(i) SEQUENCE CHARACTERISTICS:
        (A) LENGTH: 41 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:28:

```
Ala Pro Glu Met Trp Ala Lys Gly Val Lys Gly Lys Asn Ile Lys Val
1               5                   10                  15

Ala Val Leu Asp Thr Gly Cys Asp Thr Ser His Pro Asp Leu Lys Asn
                20                  25                  30

Gln Ile Ile Gly Gly Lys Asn Phe Ser
            35                  40
```

(2) INFORMATION FOR SEQ ID NO:29:

(i) SEQUENCE CHARACTERISTICS:
        (A) LENGTH: 41 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:29:

```
Gln Ala Pro Gln Ala Trp Asp Ile Ala Glu Gly Ser Gly Ala Lys Ile
1               5                   10                  15

Ala Ile Val Asp Thr Gly Val Gln Ser Asn His Pro Asp Leu Ala Gly
```

```
                            20                  25                  30
Lys Val Val Gly Gly Trp Asp Phe Val
                35                  40
```

(2) INFORMATION FOR SEQ ID NO:30:

(i) SEQUENCE CHARACTERISTICS:
        (A) LENGTH: 209 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:30:

```
Val Leu Glu Gln Asn Gly Phe Gln Pro Val Glu Ala Glu Asp Tyr Asp
1               5                   10                  15

Ser Ala Val Asn Gln Leu Asn Glu Pro Trp Pro Asp Leu Ile Leu Leu
                20                  25                  30

Asp Trp Met Leu Pro Gly Gly Ser Gly Ile Gln Phe Ile Lys His Leu
            35                  40                  45

Lys Arg Glu Ser Met Thr Arg Asp Ile Pro Val Val Met Leu Thr Ala
50                  55                  60

Arg Gly Glu Glu Glu Asp Arg Val Arg Gly Leu Glu Thr Gly Ala Asp
65                  70                  75                  80

Asp Tyr Ile Thr Lys Pro Phe Ser Pro Lys Glu Leu Val Ala Arg Ile
                85                  90                  95

Lys Ala Val Met Arg Arg Ile Ser Pro Met Ala Val Glu Glu Val Ile
                100                 105                 110

Glu Met Gln Gly Leu Ser Leu Asp Pro Thr Ser His Arg Val Met Ala
            115                 120                 125

Gly Glu Glu Pro Leu Glu Met Gly Pro Thr Glu Phe Lys Leu Leu His
130                 135                 140

Phe Phe Met Thr His Pro Glu Arg Val Tyr Ser Arg Glu Gln Leu Leu
145                 150                 155                 160

Asn His Val Trp Gly Thr Asn Val Tyr Val Glu Asp Arg Thr Val Asp
                165                 170                 175

Val His Ile Arg Arg Leu Arg Lys Ala Leu Glu Pro Gly Gly His Asp
            180                 185                 190

Arg Met Val Gln Thr Val Arg Gly Thr Gly Tyr Arg Phe Ser Thr Arg
            195                 200                 205

Phe
```

(2) INFORMATION FOR SEQ ID NO:31:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:31:

```
Ser Phe Asn Ser Tyr Thr Cys
1               5
```

(2) INFORMATION FOR SEQ ID NO:32:

(i) SEQUENCE CHARACTERISTICS:
        (A) LENGTH: 7 amino acids

```
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:32:

Ser Phe Asn Ser Met Cys Cys
1               5

(2) INFORMATION FOR SEQ ID NO:33:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:33:

Ser Phe Asn Ser Val Cys Cys
1               5

(2) INFORMATION FOR SEQ ID NO:34:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:34:

Ser Phe Asn Ser Tyr Gly Cys
1               5

(2) INFORMATION FOR SEQ ID NO:35:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:35:

Ser Phe Asn Ser Tyr Val Cys
1               5

(2) INFORMATION FOR SEQ ID NO:36:

(i) SEQUENCE CHARACTERISTICS:
            (A) LENGTH: 14 base pairs
            (B) TYPE: nucleic acid
            (C) STRANDEDNESS: both
            (D) TOPOLOGY: linear (ii) MOLECULE TYPE: cDNA (xi) SEQUENCE DESCRIPTION: SEQ ID NO:36:

GTRCADATRA AYTT                                                      14

(2) INFORMATION FOR SEQ ID NO:37:

(i) SEQUENCE CHARACTERISTICS:
            (A) LENGTH: 4 amino acids
            (B) TYPE: amino acid
```

(C) STRANDEDNESS: single
            (D) TOPOLOGY: Not Relevant (ii) MOLECULE TYPE: peptide (xi) SEQUENCE DESCRIPTION: SEQ ID NO:37:

Pro Xaa Gly Pro
1

(2) INFORMATION FOR SEQ ID NO:38:

(i) SEQUENCE CHARACTERISTICS:
            (A) LENGTH: 4 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:38:

Xaa Pro Arg Tyr
1

(2) INFORMATION FOR SEQ ID NO:39:

(i) SEQUENCE CHARACTERISTICS:
            (A) LENGTH: 5 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:39:

Xaa Asp Asp Lys Tyr
1               5

(2) INFORMATION FOR SEQ ID NO:40:

(i) SEQUENCE CHARACTERISTICS:
            (A) LENGTH: 51 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:40:

Leu Ser Ala Glu Pro Ala Val Gly Ala Ile Gly Gly Asn Ser Asp Asn
1               5                   10                  15

Ala Ala Ile Thr Gly Ala Val His Thr Gly His Gly Asn Tyr Asp Ser
                20                  25                  30

Ile Ala Asp Glu Lys Gly Gly Asp Asp Ser Phe Asn Lys Gly Gly
            35                  40                  45

Ile Ile Gln
    50

(2) INFORMATION FOR SEQ ID NO:41:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:41:

```
Ser Phe Asn Ser Tyr Cys Ser
1               5
```

(2) INFORMATION FOR SEQ ID NO:42:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:42:

```
Ser Phe Asn Ser Tyr Cys Met
1               5
```

(2) INFORMATION FOR SEQ ID NO:43:

(i) SEQUENCE CHARACTERISTICS:
        (A) LENGTH: 6 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:43:

```
Ser Phe Asn Ser Tyr Cys
1               5
```

(2) INFORMATION FOR SEQ ID NO:44:

(i) SEQUENCE CHARACTERISTICS:
        (A) LENGTH: 8 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:44:

```
Thr Leu Thr Ser Glu Cys Ile Cys
1               5
```

(2) INFORMATION FOR SEQ ID NO:45:

(i) SEQUENCE CHARACTERISTICS:
        (A) LENGTH: 8 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:45:

```
Ser Phe Asn Ser Cys Xaa Xaa Cys
1               5
```

(2) INFORMATION FOR SEQ ID NO:46:

(i) SEQUENCE CHARACTERISTICS:
        (A) LENGTH: 15 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:46:

CACATCCAGG AGTAC  15

(2) INFORMATION FOR SEQ ID NO:47:

(i) SEQUENCE CHARACTERISTICS:
        (A) LENGTH: 36 base pairs
        (B) TYPE: nucleic acid
        (C) STRANDEDNESS: both
        (D) TOPOLOGY: Not Relevant (ii) MOLECULE TYPE: cDNA (xi) SEQUENCE DESCRIPTION: SEQ ID NO:47:

GGGTTTTAGG NATCCTTTTT AATAAATTTT TAGGAG  36

(2) INFORMATION FOR SEQ ID NO:48:

(i) SEQUENCE CHARACTERISTICS:
        (A) LENGTH: 36 base pairs
        (B) TYPE: nucleic acid
        (C) STRANDEDNESS: both
        (D) TOPOLOGY: Not Relevant (ii) MOLECULE TYPE: cDNA (xi) SEQUENCE DESCRIPTION: SEQ ID NO:48:

CCTCAAAATT AAGACGAGAT GCCTCTATTG AAGCCC  36

(2) INFORMATION FOR SEQ ID NO:49:

(i) SEQUENCE CHARACTERISTICS:
        (A) LENGTH: 16 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:49:

GGTTTGGTTA TTTTCC  16

(2) INFORMATION FOR SEQ ID NO:50:

(i) SEQUENCE CHARACTERISTICS:
        (A) LENGTH: 23 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:50:

CCTCAAAATT AAGACAGAGC CTC  23

(2) INFORMATION FOR SEQ ID NO:51:

(i) SEQUENCE CHARACTERISTICS:
        (A) LENGTH: 16 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:51:

ATGGAAGCAG TAAAAG  16

(2) INFORMATION FOR SEQ ID NO:52:

(i) SEQUENCE CHARACTERISTICS:
        (A) LENGTH: 32 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:52:

CTGAATTAAC TACAATAACT GTTAAAACTA CC                                  32

(2) INFORMATION FOR SEQ ID NO:53:

(i) SEQUENCE CHARACTERISTICS:
        (A) LENGTH: 28 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:53:

CTGAATTATC AACAATAACT GTTAAAAC                                       28

(2) INFORMATION FOR SEQ ID NO:54:

(i) SEQUENCE CHARACTERISTICS:
        (A) LENGTH: 32 base pairs
        (B) TYPE: nucleic acid
        (C) STRANDEDNESS: both
        (D) TOPOLOGY: Not Relevant (ii) MOLECULE TYPE: cDNA (xi) SEQUENCE DESCRIPTION: SEQ ID NO:54:

CTGAATTAAC AACAATAAGC GTTAAAACTA CC                                  32

(2) INFORMATION FOR SEQ ID NO:55:

(i) SEQUENCE CHARACTERISTICS:
        (A) LENGTH: 11 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:55:

Ala Lys Thr Gly Ser Phe Asn Ser Tyr Cys Cys
1               5                   10

(2) INFORMATION FOR SEQ ID NO:56:

(i) SEQUENCE CHARACTERISTICS:
        (A) LENGTH: 6 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:56:

Phe Asn Ser Tyr Cys Cys
1               5

(2) INFORMATION FOR SEQ ID NO:57:

(i) SEQUENCE CHARACTERISTICS:
        (A) LENGTH: 5 amino acids
        (B) TYPE: amino acid (C) STRANDEDNESS: single
            (D) TOPOLOGY: Not Relevant (ii) MOLECULE TYPE: peptide (xi) SEQUENCE DESCRIPTION: SEQ ID NO:57:

Asn Ser Tyr Cys Cys
1               5

(2) INFORMATION FOR SEQ ID NO:58:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:58:

Ala Phe Asn Ser Tyr Cys Cys
1               5

(2) INFORMATION FOR SEQ ID NO:59:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:59:

Ser Ala Asn Ser Tyr Cys Cys
1               5

(2) INFORMATION FOR SEQ ID NO:60:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:60:

Ser Phe Ala Ser Tyr Cys Cys
1               5

(2) INFORMATION FOR SEQ ID NO:61:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:61:

Ser Phe Asn Ala Tyr Cys Cys
1               5

(2) INFORMATION FOR SEQ ID NO:62:

(i) SEQUENCE CHARACTERISTICS:
            (A) LENGTH: 7 amino acids
            (B) TYPE: amino acid

```
        (C) STRANDEDNESS: single
        (D) TOPOLOGY: Not Relevant (ii) MOLECULE TYPE: peptide (xi) SEQUENCE DESCRIPTION: SEQ ID NO:62:

Ser Phe Asn Ser Ala Cys Cys
1               5

(2) INFORMATION FOR SEQ ID NO:63:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:63:

Ser Phe Asn Tyr Tyr Cys Cys
1               5

(2) INFORMATION FOR SEQ ID NO:64:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:64:

Ser Tyr Asn Ser Tyr Cys Cys
1               5

(2) INFORMATION FOR SEQ ID NO:65:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:65:

Ser Trp Asn Ser Tyr Cys Cys
1               5

(2) INFORMATION FOR SEQ ID NO:66:

(i) SEQUENCE CHARACTERISTICS:
        (A) LENGTH: 40 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:66:

Val Ala Pro Gly Glu Asn Ile Leu Ser Thr Leu Pro Asn Lys Lys Tyr
1               5                   10                  15

Gly Lys Leu Thr Gly Thr Ser Met Ala Ala Pro His Val Ser Gly Ala
                20                  25                  30

Leu Ala Leu Ile Lys Ser Tyr Glu
            35                  40
```

(2) INFORMATION FOR SEQ ID NO:67:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:67:

```
Ser Phe Asn Ser Tyr Ala Cys
1               5
```

(2) INFORMATION FOR SEQ ID NO:68:

(i) SEQUENCE CHARACTERISTICS:
        (A) LENGTH: 21 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:68:

```
Asn Gly Asn Gly His Gly Thr His Cys Ala Gly Ile Ala Ala Ala Val
1               5                   10                  15

Thr Asn Asn Ser Thr
            20
```

(2) INFORMATION FOR SEQ ID NO:69:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:69:

```
Ser Phe Asn Ser Tyr Cys Xaa
1               5
```

(2) INFORMATION FOR SEQ ID NO:70:

(i) SEQUENCE CHARACTERISTICS:
        (A) LENGTH: 41 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:70:

```
Ala Ala Pro Gly Ser Trp Ile Tyr Ser Thr Tyr Pro Thr Ser Thr Tyr
1               5                   10                  15

Ala Ser Leu Ser Gly Thr Ser Met Ala Thr Pro His Val Ala Gly Val
                20                  25                  30

Ala Gly Leu Leu Ala Ser Gln Gly Arg
                35                  40
```

OXIDATIVE DECARBOXYLATION OF PEPTIDES CATALYZED BY FLAVOPROTEIN EPID

BACKGROUND OF THE INVENTION

1. Field of the Invention

This invention relates to a method of oxidatively decarboxylating a peptide, comprising combining a peptide with EpiD, wherein the peptide comprises at its carboxy terminus the amino acid sequence $X_1X_2X_3X_4X_5X_6C$, (SEQ ID NO:1) wherein $X_1$, $X_2$, $X_3$ and $X_4$ are any one of the twenty common amino acids, $X_5$ is Tyr, Val, Met, Phe, Leu, Ile or Trp, and $X_6$ is Cys, Ala, Ser, Val, or Thr, with the proviso that the carboxy terminus of said peptide is not SFNSYCC, (SEQ ID NO:2) SFNSFCC, (SEQ ID NO:3) SFNSWCC (SEQ ID NO:4) or SFNSYSC, (SEQ ID NO:5) whereby the oxidative decarboxylation of the peptide occurs.

2. Related Art

Some polypeptide antibiotics such as nisin, subtilin, duramycin, cinnamycin, ancovenin, Ro 09-0198 and epidermin contain dehydroamino acids and lanthionine bridges. These polypeptides are produced by various respective strains of microorganism. Nisin for example can be produced by cultivating strains of *Streptococcus lactin*, and subtilin by cultivation of *Bacillus subtilis*.

The genetic basis for the biosynthesis of these antibiotics has not, hitherto, been elucidated. Thus, it has not been known, for example, whether biosynthesis of such antibiotics and, in particular, the formation of the unusual amino acids found therein occurs via ribosomal synthesis or via multi-enzyme complexes.

It addition it was not known whether the precursor proteins of such antibiotics were coded by distinct structural genes or were the degradation products of larger proteins.

In the course of work carried out to establish the structural gene of epidermine, it has been established that surprisingly the above mentioned antibiotics, in particular epidermin, are each coded by a distinct structural gene, and that processing of a presequence polypeptide is carried out by an enzymatic complex which effects formation of dehydroamino residues and/or thioether bridges.

Furthermore, the multi-enzyme complex may be involved in the secretion of the protein through the cell membrane into the culture supernatant, as well as processing a pre-polypeptide. In this connection, such activity may be associated with a pre-sequence possessed by the pre-polypeptide, e.g., as in the case of the –30 to –1 sequence of pre-epidermin as described below.

It has unexpectedly been determined that the multienzyme complex responsible for the posttranslational modification of pre-epidermin is located on the 54 kb plasmid pTü32 of *Staphylococcus epidermis* Tü 3298/DSM 3095.

The six genes (ORFs) responsible for the production of epidermin are designated herein epi A, B, C, D, Q and P and are clustered within 8 kb and the proteins for which they code are designated Epi A, B, C, D, Q and P respectively; epi A encodes the 52 amino acid-long pre-epidermin. As described below, epi B, C and D are involved in the four enzymatic modification reactions (i) water elimination by a serine/threonine dehydratase, (ii) sulfur addition by a lanthinonine synthase, (iii) C-terminal decarboxylation by a cysteine decarboxylase and (iv) double bond formation. Epi P protein is believed to be responsible for cleaving the mature epidermin from the N-terminal leader peptide, based on its striking homologies with the essential domain of serine proteases (Koide et al., *J. Bacteriol.* 167:110–116 (1986); Meloun et al., *FEBS Lett.* 183:195–200 (1985); and Stahl et al., *J. Bacteriol.* 158:411–418 (1984)) while Epi Q is believed to be a regulatory protein regulating epidermin biosynthesis, based on its distinct homology to the pho B gene of *E. coli* (Makino et al., *J. Mol. Biol.* 190:37–44 (1986)), the fact that both proteins are of a similar size with 205 (epi Q) and 229 (pho B) amino acid residues, the observed homology of 24.2% extending over the 153 C-terminal amino acid residues and the hydrophilicity plots of both proteins.

The enzyme EpiD has been purified and identified as a flavoprotein with flavin mononucleotide as coenzyme (Kupke, T. et al., *J. Bacteriol.* 174:5354–5361 (1992)). The EpiD* gene of the epi-mutant *S. epidermis* TUS3298/EMS 11 has been expressed as a maltose-binding protein (MBP)-EpiD* fusion protein in *Escherichia coli*. Unlike MBP-EpiD, this fusion protein MBP-EpiD* cannot bind the flavin coenzyme. DNA sequencing of EpiD* identified a point mutation that led to replacement of $Gly^{93}$ with Asp (Kupke, T. et al., *J. Bacteriol.* 174:5354–5361 (1992)).

The substrate peptide EpiA and the mutated peptide EpiAR-1Q have been purified by factor Xa cleavage from MBP fusions. The identity of purified EpiA and EpiAR-1Q have been confirmed by electrospray mass spectrometry (ES-MS) and amino acid sequencing (Kupke, T., et al., *FEMS Lett* 112:43–48 (1993)). EpiA consists of an $NH_2$-terminal leader peptide (amino acids –30 to –1 ) and a COOH-terminal proepidermin (amino acids +1 to +22) (Schnell, N., et al, *Nature* 333:276–278 (1988)). The last two amino acids of EpiA are cysteine residues.

Recently, it was demonstrated that under reducing conditions, EpiD reacts with unmodified precursor peptides EpiA and EpiAR-1Q and with the COOH-terminal proepidermin fragment of EpiA as shown by reversed phase chromatography and ES-MS (Kupke, T., et al., *J. Biol. Chem.* 269:5653–5659 (1994)). A decrease in mass by 46 Da was observed, and an increase in absorbance at 260 nm of the modified peptides. Sequence analysis of modified proepidermin indicates that one of the two last cysteine residues of proepidermin is modified by EpiD. A model has been proposed that EpiD catalyzes the removal of two reducing equivalents from the side chain of the COOH-terminal cysteine residue (Kupke, T., et al., *J. Biol. Chem.* 269:5653–5659 (1994)). A double bond is formed, and the flavin mononucleotide coenzyme is reduced. The COOH-terminal carboxyl group is then removed by a decarboxylation reaction resulting in the COOH-terminal enethiol side chain. The oxidated and decarboxylated peptide is unstable and is nonenzymatically converted to less hydrophobic peptides. The reaction is inhibited by $Zn^{2+}$, and the oxidative decarboxylated peptide is probably stabilized by $Zn^{2+}$ (Kupke, T., et al, *J. Biol Chem.* 269:5653–5659 (1994)). It was concluded that the oxidoreductase EpiD is involved in formation of the COOH-terminal S-[(Z)-2-aminovinyl]-D-cysteine.

Clearly, further characterization of this novel posttranslational modification reaction is necessary. One major question regarding posttranslational modifications concerns the specificity of the processing reactions in selecting only a few or sometimes even only one residue for modification (Yan, S. C. B., et al., *Trends Biochem. Sci.* 14:264–268 (1989)).

SUMMARY OF THE INVENTION

Therefore, the invention relates to an investigation of the substrate specificity of the enzyme EpiD using mutated precursor peptides, synthetic peptides, and peptide libraries. Synthetic peptide libraries are useful new tools for the identification of optimal peptide ligands, for example the determination of antigenic peptides (Houghten, R. A., et al., Nature 354:84–86 (1991); Lam, K. S., et al, Nature 354:82–84 (1991)). Even complex peptide libraries can be analyzed by ES-MS (Metzger, J. W., et al., Anal. Biochem. 210:261–277 (1994)). The enzymatic reaction products were characterized by tandem mass spectrometry and isoelectric focusing. In addition, the protein-peptide interaction between EpiD and EpiA coupled to NHS-activated HiTrap was investigated. These studies allowed the determination of the substrate specificity of EpiD.

Thus, the invention provides a method of oxidatively decarboxylating a peptide, comprising combining a peptide with EpiD, wherein the peptide comprises at its carboxy terminus the amino acid sequence $X_1X_2X_3X_4X_5X_6C$, (SEQ ID NO:1) wherein $X_1$, $X_2$, $X_3$ and $X_4$ are any one of the twenty common amino acids, $X_5$ is Tyr, Val, Ile, Leu, Met, Phe or Trp, and $X_6$ is Cys, Ala, Ser, Val, or Thr, whereby the oxidative decarboxylation of said peptide occurs.

In a preferred embodiment, the peptide comprises an amino acid sequence selected from the group consisting of $X_1$FNSYCC; (SEQ ID NO:6) $SX_2$NSYCC; (SEQ ID NO:7) $SFX_3$SYCC; (SEQ ID NO:8) $SFNX_4$YCC; (SEQ ID NO:9) $SFNSX_5$CC; (SEQ ID NO:10) $SFNSYX_6$C; (SEQ ID NO:11) $SFNSX_5X_6$C; (SEQ ID NO:12) $SFX_3X_4$YCC; (SEQ ID NO:20) $SX_2X_3X_4$YCC; (SEQ ID NO:21) and $X_1X_2X_3X_4$YCC, (SEQ ID NO:22) wherein $X_1$, $X_2$, $X_3$ and $X_4$ are any one of the twenty common amino acids, $X_5$ is Tyr, Val, Met, Leu, Ile, Phe or Trp, and $X_6$ is Cys, Ala, Ser, Val, or Thr, with the proviso that the carboxy terminus of said peptide is not SFNSYCC, (SEQ ID NO:2) SFNSFCC, (SEQ ID NO:3) SFNSWCC (SEQ ID NO:4) or SFNSYSC (SEQ ID NO:5).

In another preferred embodiment, the carboxy terminus of the peptide comprises the amino acid sequence $SFNSX_5X_6C$, (SEQ ID NO:12) wherein $X_5$ is Tyr, Val, Met, Leu, Ile, Phe or Trp, and $X_6$ is Cys, Ala, Ser, Val, or Thr.

In yet another preferred embodiment, the carboxy terminus of the peptide comprises the amino acid sequence $SFNSX_5CC$, (SEQ ID NO:15) wherein $X_5$ is Val, Met, Leu, Ile, Phe or Trp.

In another preferred embodiment, the carboxy terminus of the peptide comprises the amino acid sequence $SFNSYX_6C$, (SEQ ID NO:11) wherein $X_6$ is Ala, Ser, Val, or Thr.

In another preferred embodiment, the carboxy terminus of the peptide comprises the amino acid sequence SFNSYCC (SEQ ID NO: 2).

In another preferred embodiment, the method of oxidatively decarboxylating a peptide comprises combining a peptide with a fusion protein comprising EpiD, wherein the peptide comprises at its carboxy terminus the amino acid sequence $X_1X_2X_3X_4X_5X_6C$, (SEQ ID NO:1) wherein $X_1$, $X_2$, $X_3$ and $X_4$ are any one of the twenty common amino acids, $X_5$ is Tyr, Val, Met, Phe, Ile, Leu or Trp, and $X_6$ is Cys, Ala, Ser, Val, or Thr, whereby the oxidative decarboxylation of said peptide occurs.

In a more preferred embodiment, the fusion protein is Maltose Binding Protein-EpiD.

The invention also relates to a method of oxidatively decarboxylating a peptide, comprising combining a peptide with EpiD, wherein the peptide comprises at its carboxy terminus the amino acid sequence SYCC, (SEQ ID NO:27) whereby the decarboxylation of the peptide occurs.

In another preferred embodiment, the oxidative decarboxylation occurs in vitro in the presence of a substance capable of reducing disulphide bridges. In a more preferred embodiment, the substance is selected from the group consisting of dithiothreitol, β-mercaptoethanol, and glutathione. In a still more preferred embodiment, the substance is dithiothreitol.

In another preferred embodiment, the method of oxidative decarboxylation of a peptide occurs in a bacterial host capable of expressing
   (a) a recombinant DNA molecule encoding the peptide; and
   (b) a recombinant DNA molecule encoding the protein EpiD having the amino acid sequence set forth in FIG. 9.

In another preferred embodiment, the invention relates to a bacterial host cell capable of expressing
   (a) a recombinant DNA molecule encoding a peptide capable of being oxidatively decarboxylated by EpiD; and
   (b) a recombinant DNA molecule encoding the protein EpiD having the amino acid sequence set forth in FIG. 9.

BRIEF DESCRIPTION OF THE FIGURES

FIG. 1 depicts the nucleotide sequence (SEQ ID NO:18) of the epidermin structural gene (epiA) and the deduced amino acid sequence (SEQ ID NO:14) of pre-epidermin. A Shine-Dalgarno sequence is boxed and the proteolytic cleavage site at which the propeptide is processed is indicated by an arrow. Inverted repeats are underlined and potential stop codons are noted as am (amber) and oc (ochre).

8C: Southern hybridization of pTü32 digested with different restriction enzymes (EcoRI, EcoRV, BglIII, SphI) using a 15-mer oligonucleotide (5'CACATCCAGGAGTAC-3' (SEQ ID NO:46)) specific of epiA.

FIG. 9A–L show a nucleotide sequence (SEQ ID NO:18) of the BglII/HpaII fragment of pTü32 containing reading frames epiA,(SEQ ID NO:14) B, (SEQ ID NO:15) C, (SEQ ID NO:23) D, (SEQ ID NO:24) P, (SEQ ID NO:26) Q, (SEQ ID NO:25) Y' (SEQ ID NO:13) and Y" (SEQ ID NO: 19) and the deduced amino acid sequences of the respective proteins. S/D sequences and termination structures are overlined. IR indicates inverted repeats. The start of the open reading frames of epiY, epiA, epiB, epiC, EpiD, epiQ and epiP are indicated by bold letters. The N-terminal amino acid residues (possible translational start sites) are boxed.

Figures 10A, 10B:
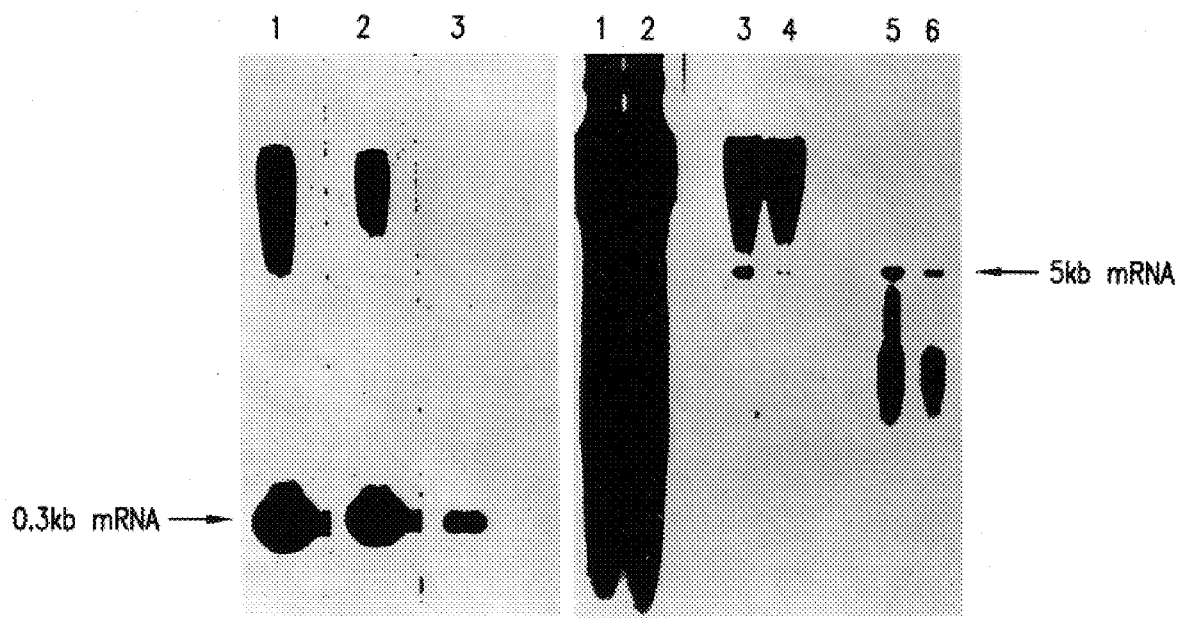

FIGS. 10A and B show the results of a Northern blot analysis of epiA (10A) and epiB (10B) expression in *S. epidermidis*, in which total RNA (40 μg, lanes 1, 3, and 5, or 20 μg, lanes 2, 4, and 6) were separated on 1.2% agarose gels and hybridization was performed with an antisense RNA probe (SP6 transcript. Filters were washed with increasing stringency; lanes 1, 2:1×SSC, 0.1% SDS, exposition time, 4 h, lanes 3, 4:0.5×SSC, 0.1% SDS, exposition time 16 h; lanes 5,6:0.1×SSC, 0.1% SDS, exposition time, 3 days). The positions of 23S and 16S RNAs were used as a size standards.

FIG. 11 shows sequence homologies between EpiP and different serine proteases at the active sites (SUBSI, subtilisin I168 precursor of *B. subtilis* (Terzaghi et al., *Appl. Microbiol.* 29: 807–813 (1975); major intracellular serine protease from *B. subtilis* (Maniatis et al., *Molecular Cloning. A Laboratory Manual;* 2nd ed. Cold Spring Harbour Laboratory Press (1990); SUMYTV, thermitase from *Thermoactinomyces vulgaris* (Stahl et al., *J Bacteriol* 158: 411–418 (1984)). The strongly conserved asparagine (asp), histidine (his), and serine (ser) residues are marked by asterisks. Similar amino acid residues are indicated by points and identical amino acid residues by colons.

FIG. 12 shows sequence homologies between epiQ and PhoB (Makino et al., *J. Mol. Biol.* 190:37–44 (1986)). Similar amino acid residues are indicated by points and identical amino acid residues by colons.

Figure 13C:
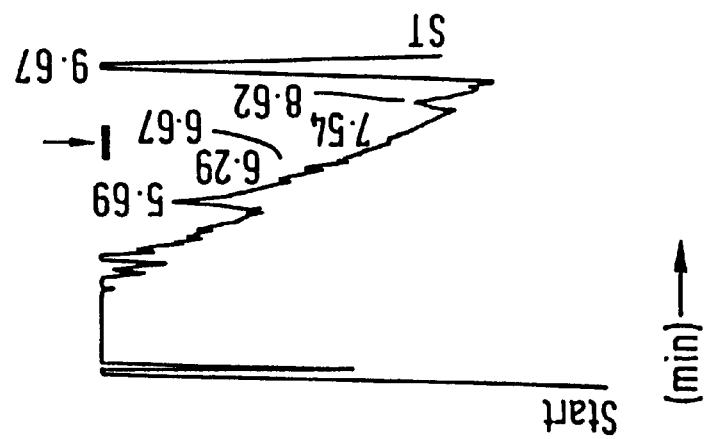
Figure 13B:
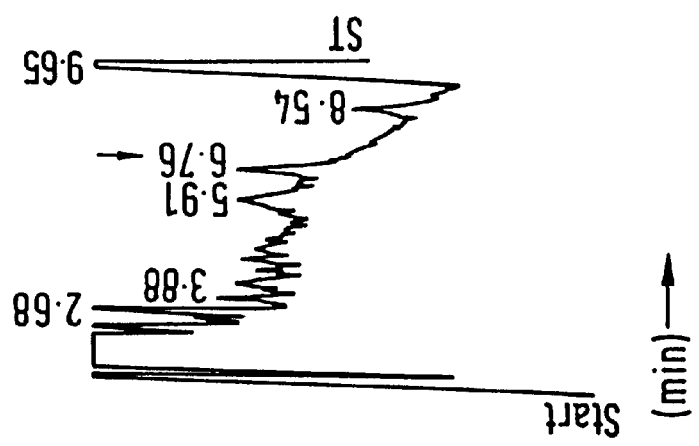
Figure 13A:
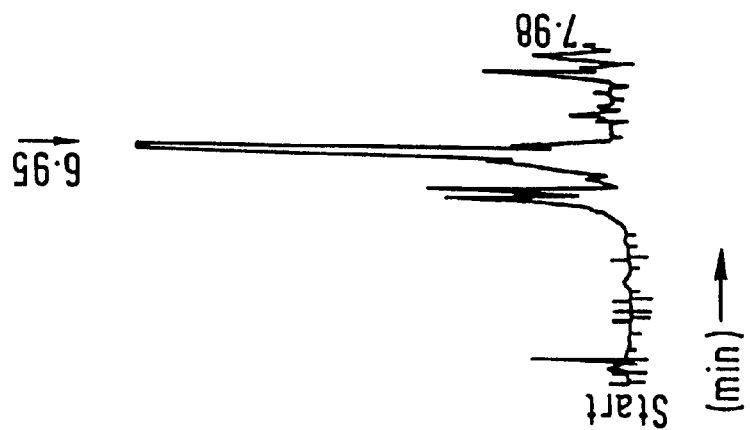

FIG. 13 is a HPLC elution profile of epidermin which was produced in *S. carnosus* TM300.

13A: Elution profile of epidermin standard substance (6.75 min, indicated by an arrow).

13B: Elution profile of epidermin standard substance (6.75 min, indicated by an arrow) isolated from culture filtrates of *S. carnosus* TM300 pTepi14. Culture filtrates were adsorbed to XAD 1180, eluted with methanol and finally concentrated by evaporation.

13C: Elution profile of untransformed *S. carnosus* TM300 culture filtrate treated as in 13B. The solid line indicates the elution region of epidermin.

Figure 14:
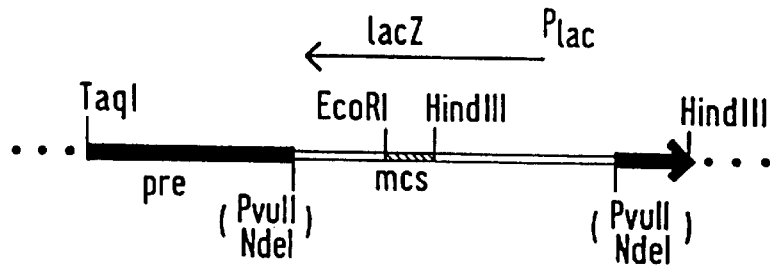

FIG. 14 shows the construction of pT181mcs. The PvuII$^{309}$-PvuII$^{631}$ fragment of pUC19, part of lacZ and the multiple cloning site (mcs), was inserted into the single NdeI site within pre of pT181 (Gennaro et al., *J. Bacteriol.* 169:2601–2610 (1987); Kahn et al, *Plasmid* 10:251–259 (1983)) by blunt-end ligation. lacZ is in the opposite orientation to a pre. Black bar, interrupted pre; open bar, inserted pUC19 fragment.

Figure 15:
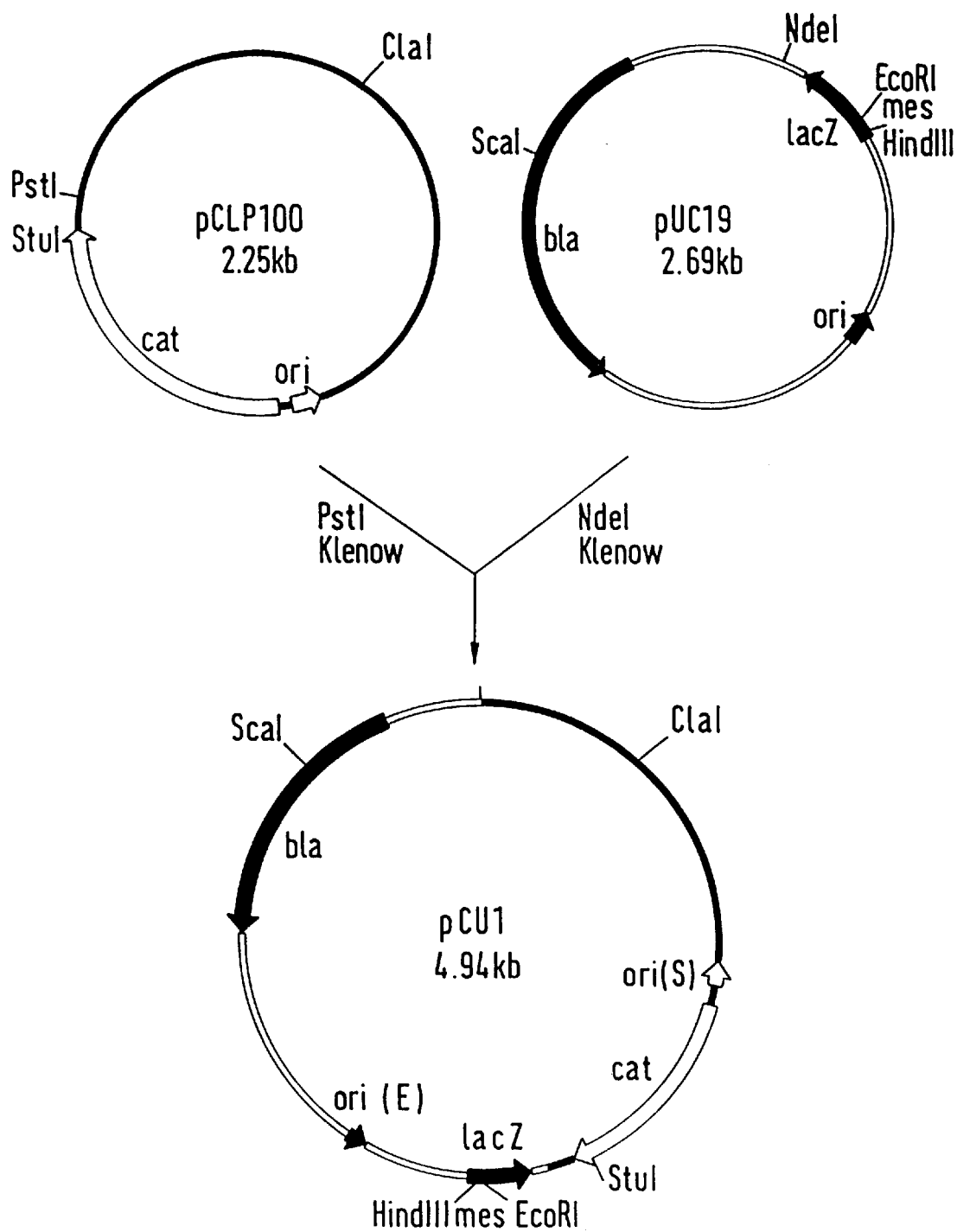

FIG. 15 shows the construction of pCU1. PCLP100 is a derivative of pC194 (Horinouchi et al, *J. Bacteriol.* 150:815–825 (1982)) containing a single Pst1 site which was generated by opening pC194 at the HindIII site, deleting the ends with Ba131 (approximately 950 bp) and inserting a PstI-linker by blunt-end ligation. PCU1 was then generated by blunt-end ligation of pCPL100 and pUC19 (Vieira et al., *Gene* 19:259–268 (1982)) via the single PstI and NdeI sites, respectively. The multiple cloning site (mcs) in front of lacZ was used for cloning various epi gene-containing fragments. This shuttle vector replicates both in staphylococci and *E. coli*.

FIG. 16 shows:

A) the generation of pTepi14 by cloning the 14 kb BglII fragment of pTü32 in pT181 mcs. This fragment containing the entire genetic information necessary for epidermin production in *S. carnosus*. The indicated ORFs and their transcriptional directions (indicated by arrows) are deduced from the DNA sequence. epiA, the structural gene, is presented by the black arrow.

B) various pTepi14 DNA fragments subcloned into pT181mcs (pT . . .) or pCU1 (pCU . . .). The respective plasmids were used to complement the *S. epidermidis* Epi$^{31}$mutants. The complete ORFs represent in the plasmid are indicated.

Figure 17:
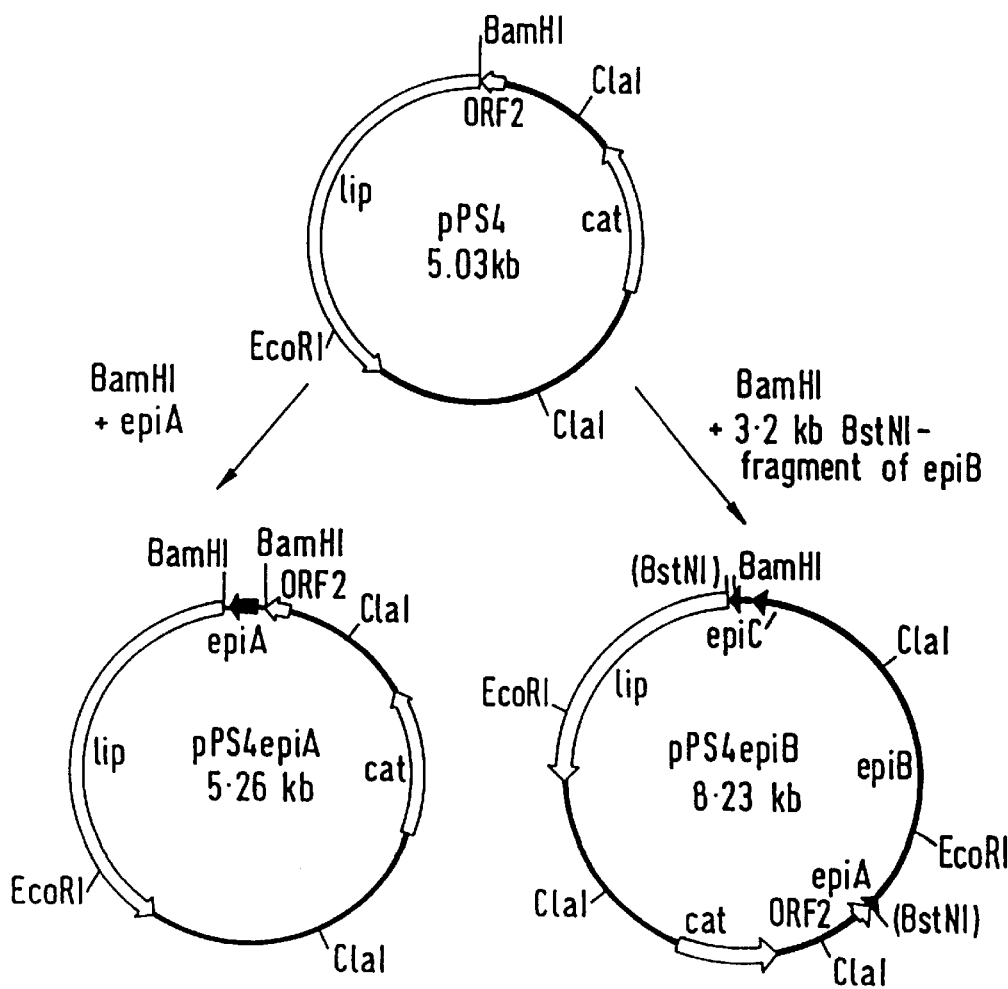

FIG. 17 shows the construction of pPS4epiA and pPS4epiB. pPS4 is a derivative of pLipPS1 (Liebl et al., *Mol. Gen. Genet.* 204:166–173 (1986)). A single BamHI site was inserted after a strong staphylococcal promoter. Cloning of genes into the BamHI site under the control of the ORF2 promoter normally leads to good expression in staphylococci. epiA was PCR-amplified and contained flanking BamHI sites. The 3.2 kb BstNI fragment containing epiB was inserted into the BamHI site by blunt-end ligation. The respective EMS-mutants were complemented only when epiA and epiB were under the control of the ORF2 promoter. lip, lipase gene; cat, chloramphenicol acetyl transferase gene; ORF2, *S. carnosus*-specific truncated ORF.

Figure 18:
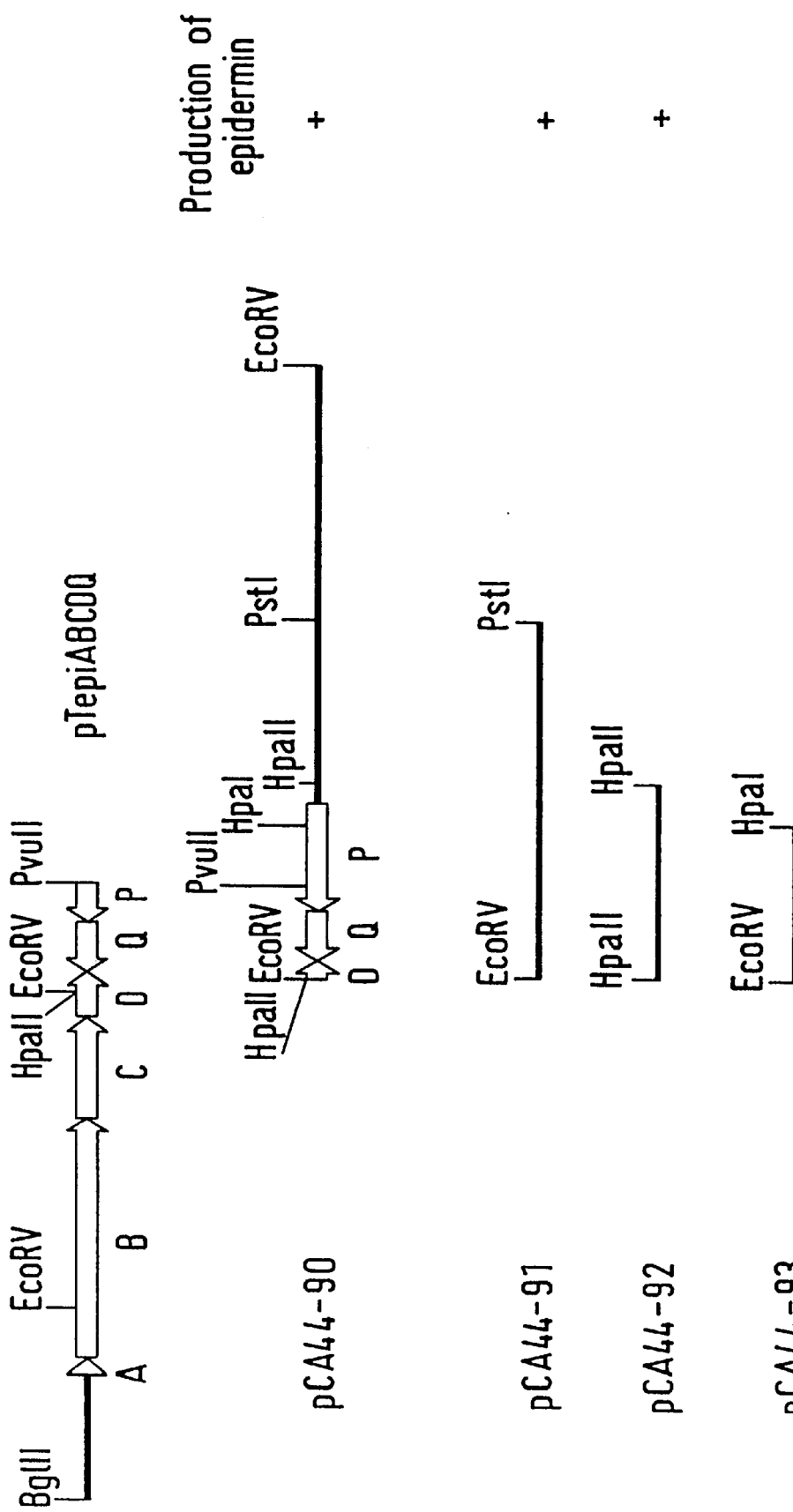

FIG. 18 shows the complementation of epidermin production in *S. carnosus* (pTepiABCDQ) by flanking DNA fragments. The fragments were subcloned into the compatible plasmid.

Figure 19A:
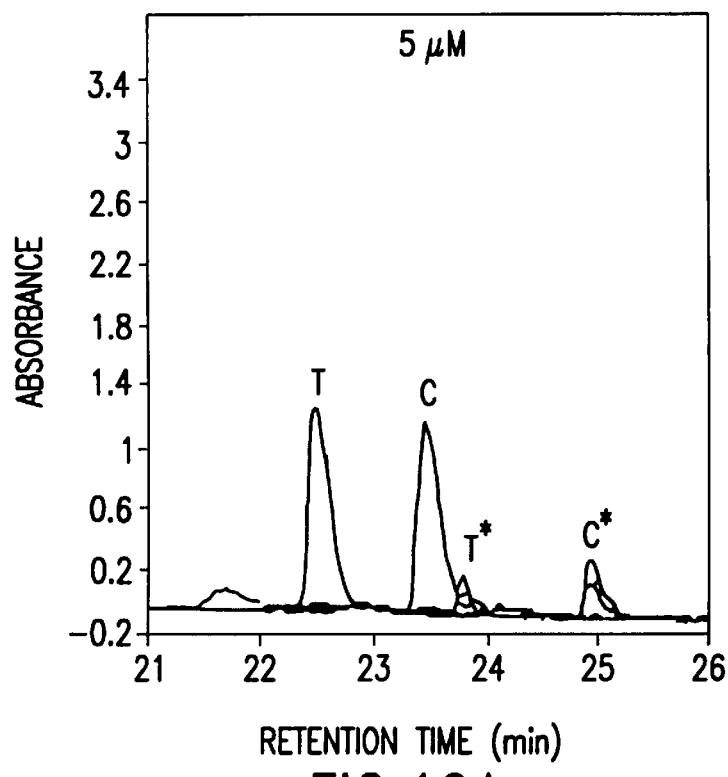
Figure 19B:
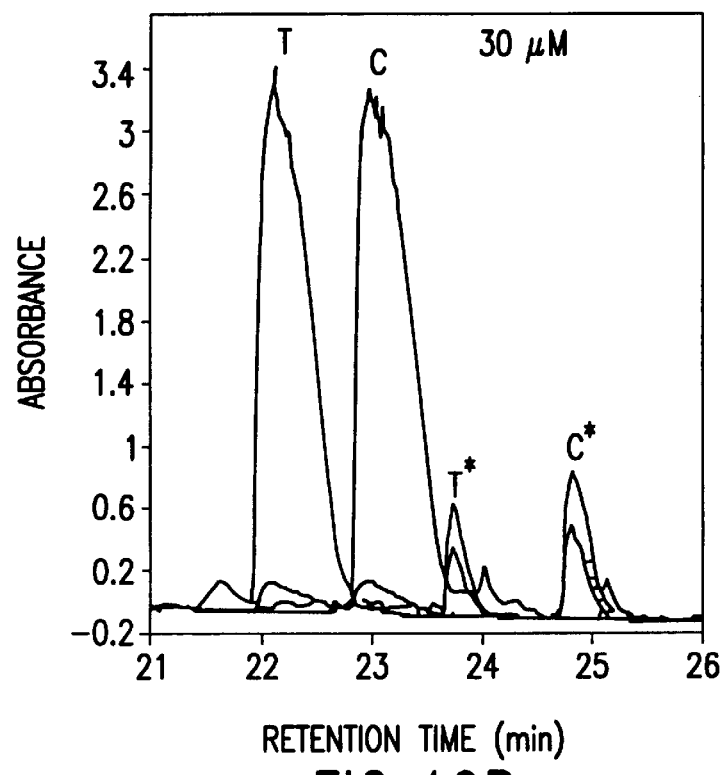

FIGS. 19A and 19B show in two graphs an analysis of the reaction of EpiD with SFNSYTC (SEQ ID NO:31)and SFNSYCC (SEQ ID NO:2). The reaction of EpiD with the single heptapaptides SFNSYTC (SEQ ID NO:21) (labeled with Thr) and SFNSYCC (SEQ ID NO:2) (labeled with Cys) was investigated. The assay (total volume of 1 ml) was carried out in 20 mM Tris/HC1 (pH 8.0) containing 3 mM dithiothreitol and 5 μM or 30 μM of one of the peptides and approximately 15 nM EpiD. The reaction was stopped after 15 min of incubation at 37° C. by adding 10 μl of trifluoroacetic acid. The reaction mixture was separated on a Pharmacia μRPC C2/C18 SC 2.1/10 column, and the elution was followed by absorbance at 214 nm (thin line) and 260 nm (thick line). For comparison of the reaction rates, the elution profiles of both peptide incubations were overlaid in one figure. The peak fractions were analyzed by ES-MS; T* and C* were identified as SFNSYTC (SEQ ID NO:31) –46 Da and SFNSYCC (SEQ ID NO:2) –46 Da, respectively.

FIGS. 20A–D show the product ion spectra of SFNSYTC, (SEQ ID NO:31) SFNSYTC (SEQ ID NO:31) –46 Da (20A and B) and SFNSYC, (SEQ ID NO:5) SFNSYSC –46 Da (20C and D). For SFNSYTC (SEQ ID NO:31) and SFNSYTC −46 Da, the amino-terminal fragments are labeled $B_1$–$B_6$, and the corresponding peptide sequence is indicated. The $B_1$–$B_5$ fragments were identical for all four peptides. SFNSYTC (SEQ ID NO: 31) has the same $B_6$ fragment as SFNSYTC (SEQ ID NO:31) −46 Da (700.5 m/z), and SFNSYSC (SEQ ID NO:5) the same as SFNSYSC (SEQ ID NO:5) −46 Da (686.5 m/z), showing that the last amino acid residue (cysteine) is modified. The mass difference between the educts and their $B_6$ fragments is 121 mass units; between the reaction products and their $B_6$ fragments, the difference is 75 mass units. SFNSYTC and SFNSYSC, as well as SFNSYTC −46 Da and SFNSYSC −46 Da, differ in their $B_6$ fragment by 14 Da, demonstrating the Thr/Ser exchange. Carboxyl-terminal fragments $Y_n$ were present only to a very small extent. $Y_n$ fragments are more pronounced if the COOH-terminal residue of the investigated peptide is a basic amino acid residue, such as lysine or arginine (Biemann, K., *Methods Enzymol.* 183:455–479 (1990)).

Figure 21A:
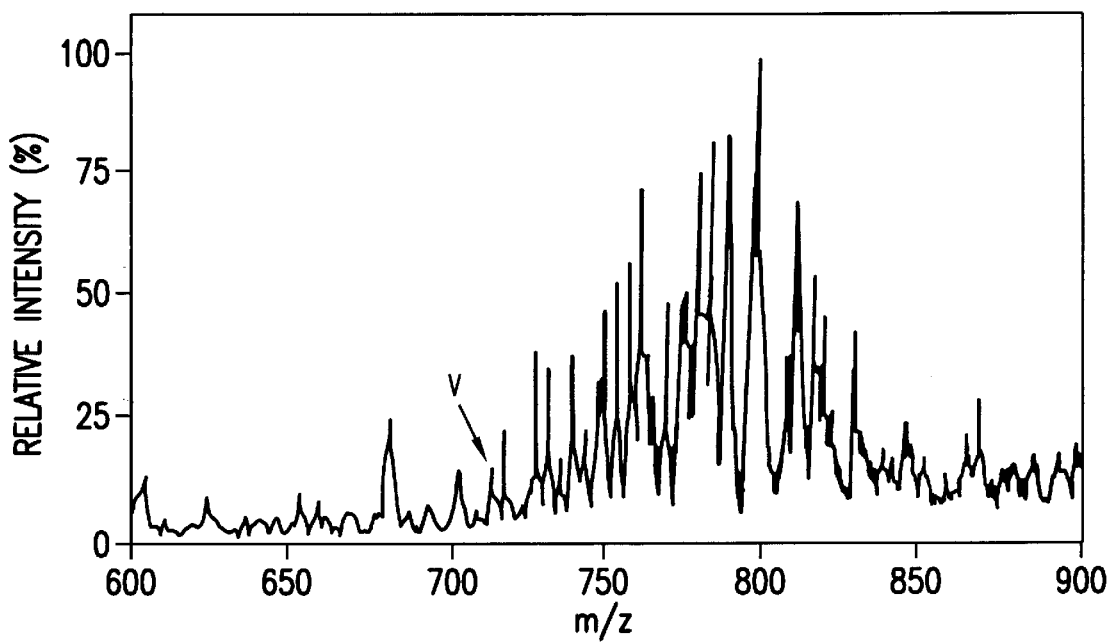
Figure 21B:
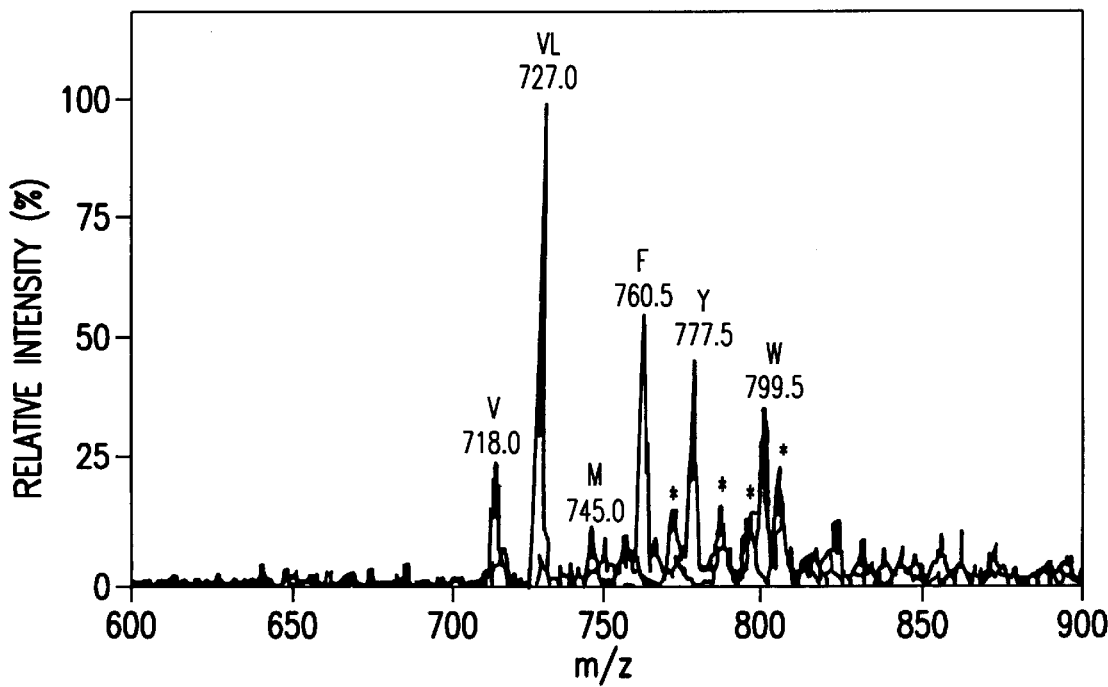

FIGS. 21A and 21B show the determination of the substrate specificity of EpiD using the peptide library SFNSXCC (SEQ ID NO:10). The peptide library SFNSXCC was incubated with EpiD. The reaction mixture containing educts and products was analyzed by ES-MS (21A) and by neutral loss mass spectrometry (neutral loss=75 mass units). Also recorded was a neutral loss mass spectrum of the peptide library before incubation with EpiD. The neutral loss scans are overlaid in FIG. 21B. By neutral loss mass spectrometry mainly the reaction products were filtered from the complex peptide mixture. Peptides detected by both neutral loss mass spectra are not reaction products and are labeled with an asterisk. In contrast, the reaction products were labeled with the one-letter code for amino acid residues; F indicates that SFNSFCC (SEQ ID NO:3) was a substrate of EpiD and that SFNSFCC −46 Da is, therefore, detected by neutral loss scans. The signal for SFNSMCC (SEQ ID NO:32) −46 Da was weak, so it is not certain if SFNSMCC (SEQ ID NO:32) is a substrate of EpiD. Some of the peaks obtained in the electrospray mass spectrum (21A) were also analyzed by product ion spectrum. SFNSVCC (SEQ ID NO:33) −46 Da was identified by this procedure.

Figure 22A:
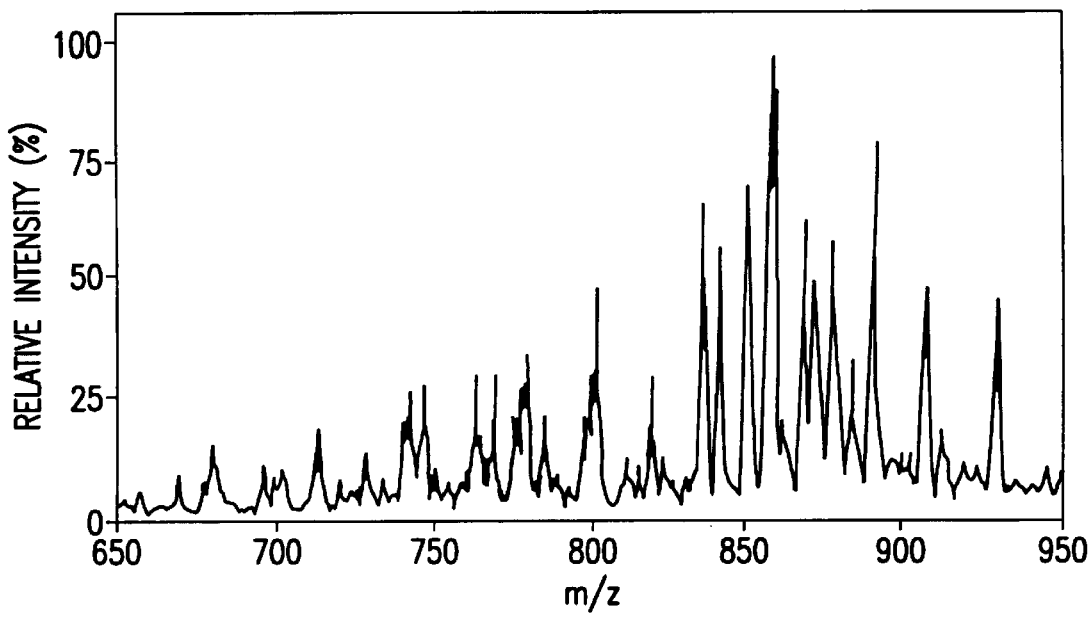
Figure 22B:
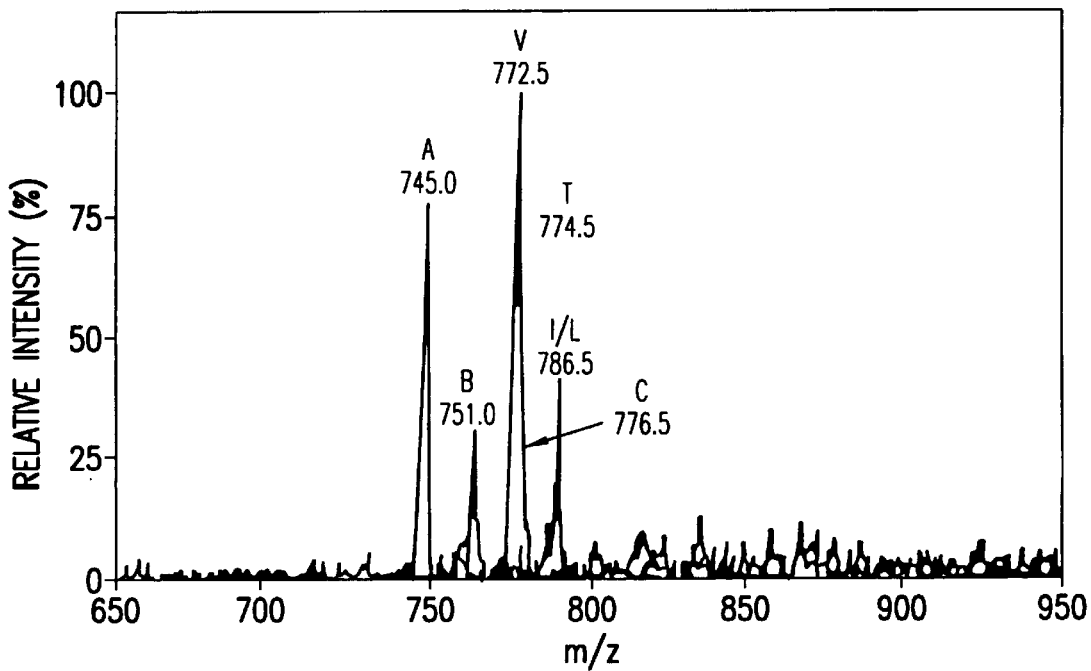
Figure 23A:
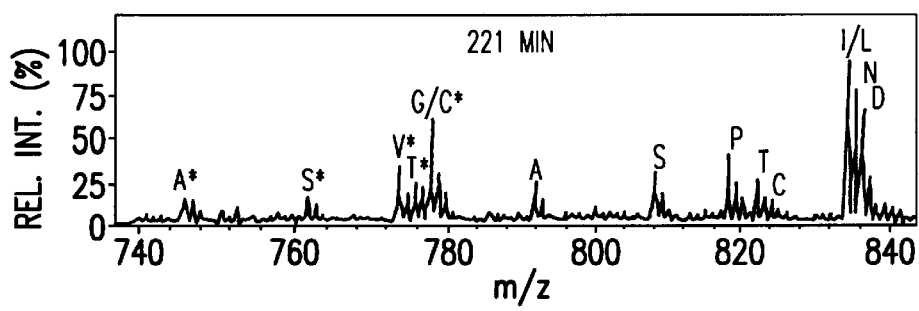
Figure 23B:
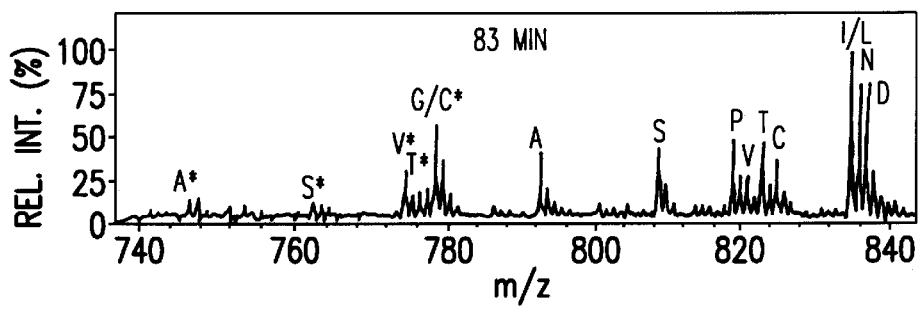
Figure 23C:
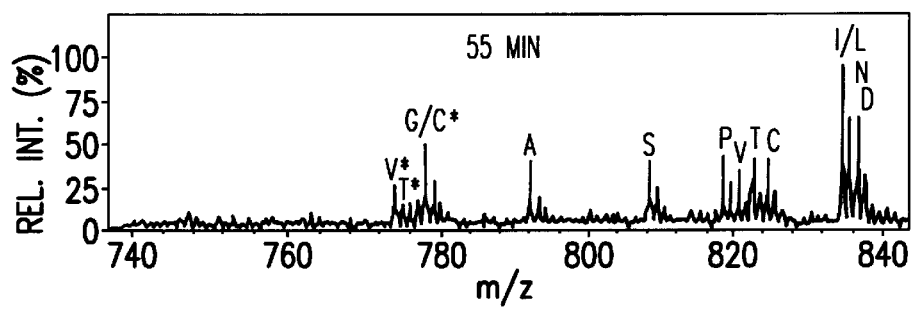
Figure 23D:
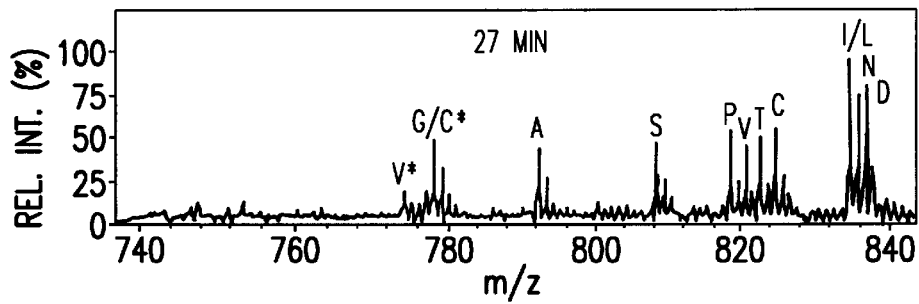
Figure 23E:
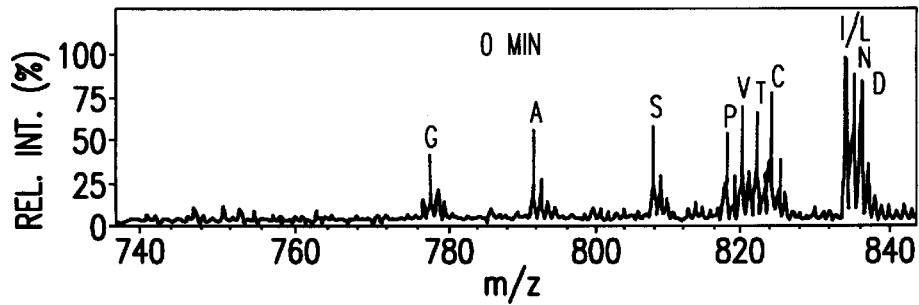

FIGS. 22A and 22B show that the cysteine residue $Cys^6$ of the heptapetide $S^1FNSYCC^7$ (SEQ ID NO:2) can be replaced by other amino acid residues. The peptide library SFNSYXC (SEQ ID NO:11) was incubated with EpiD. The reaction mixture containing educts and products was analyzed by ES-MS (22A) and by neutral loss mass spectrometry(22B) (Neutral loss=75 mass units). The neutral loss mass spectrum of the peptide library before incubation with EpiD (no dominant peaks were observed) was overlaid with the neutral loss mass spectrum of the complex peptide mixture (22B). The reaction products were identified as SFNSYXC (SEQ ID NO:11) −46 Da with X representing A, S, V, T, C, or I/L. The signal for SFNSYCC (SEQ ID NO:2) −46 Da was very weak, probably due to disulfide bride formation of the two cysteine residues, resulting in different fragmentation behavior of the peptide in collision-induced dissociation experiments.

FIGS. 23A, 23B, 23C, 23D and 23E show the kinetic analysis of the reaction of EpiD with the library SFNSYXC (SEQ ID NO:11). A solution of the peptide library SFNSYXC (600 μl of 0.4 mg/ml in 20 mM Tris/HCl, pH 8.0, 3 mM dithiothreitol) was incubated with 0.7 μg of EpiD at 23° C. After 0, 27, 55, 83, and 221 min., electrospray mass spectra of the reaction mixtures were recorded. A part of the spectra containing the signals for the educts SFNSY-A/S/P/V/T/C-C and for (SEQ ID NO:11) the products (labeled with an asterisk) is shown for the various incubation times (the monoisotopic peaks are labeled with the one-letter code for amino acid residues). When Cys was exchanged for Ile/Leu at position 6 of the heptapeptide, no reaction product was detectable by ES-MS. The very low amounts of SFNSYI/LC (SEQ ID NO:11) −46 Da (787 Da) present were only detectable using the more sensitive neutral loss mass spectrometry; it was therefore possible to normalize the spectra by setting the signal at m/z=833 to 100%. SFNSYGC (SEQ ID NO:34) (monoisotopic mass of 777 Da; not a substrate of EpiD) has the same mass as SFNSYCC (SEQ ID NO:2) −46 Da. The decrease in the signal intensity for the different educts (and the increase in the signal intensity for the corresponding products) correlates with the extent of conversion by EpiD. In a control experiment, it was confirmed that for a given peptide, the signal intensity in ES-MS was approximately directly proportional to the concentration of the peptide (concentration range of peptide library SFNSYXC (SEQ ID NO:11) used was 0.1–0.8 mg/ml; data not shown). The highest reaction rates were observed with SFNSYCC and SFNSYVC (SEQ ID NO:35).

Figure 24:
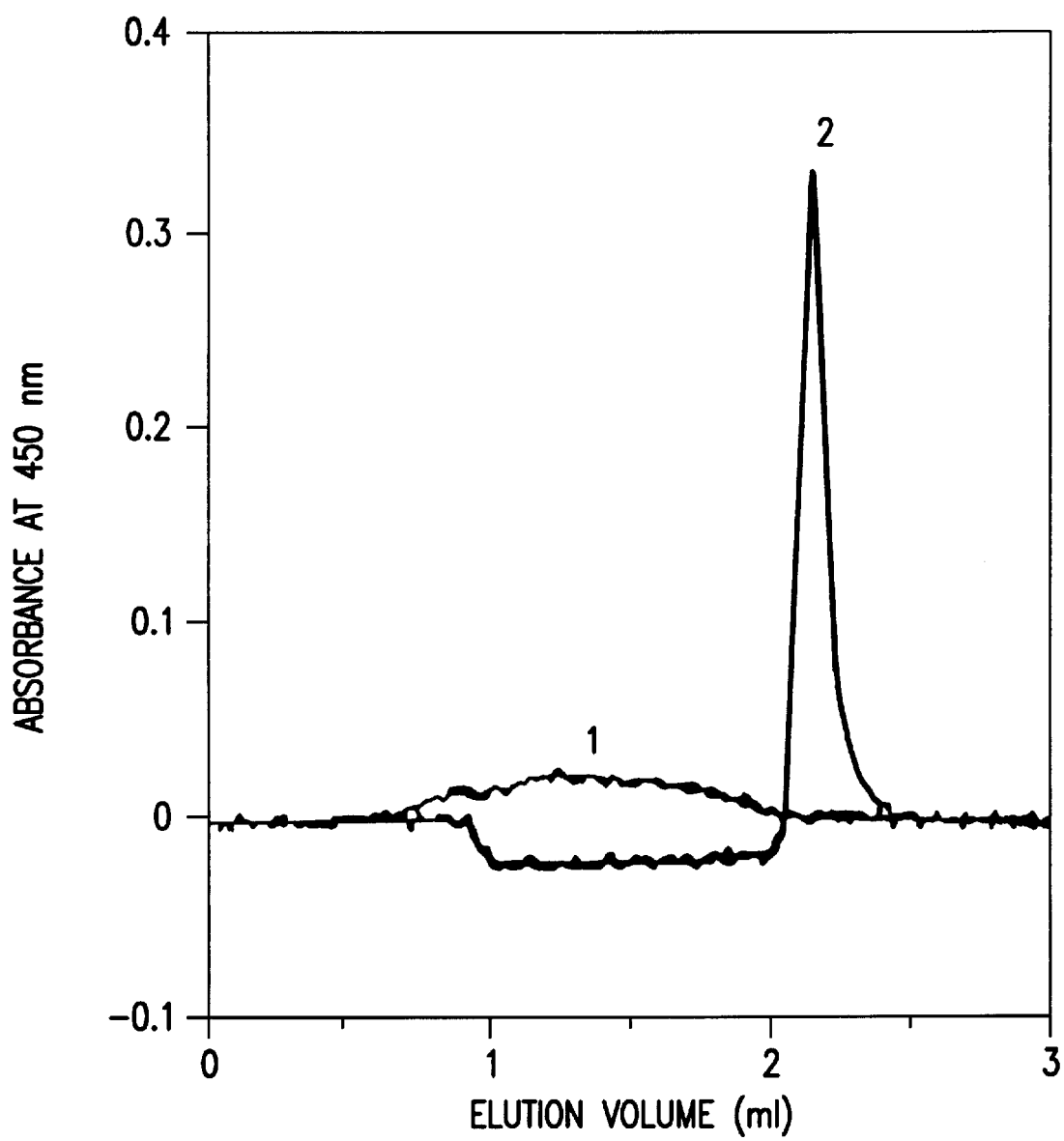

FIG. 24 shows the interaction between EpiD and an EpiA-HiTrap column. Purified EpiD was separated on an EpiA-HiTrap column under oxidizing (curve 1) and reducing conditions (curve 2). The elution of EpiD was followed by absorbance at 450 nm. When EpiD was separated under reducing conditions on a control column containing no coupled EpiA, the resulting chromatogram was the same as curve 1.

Figure 25:
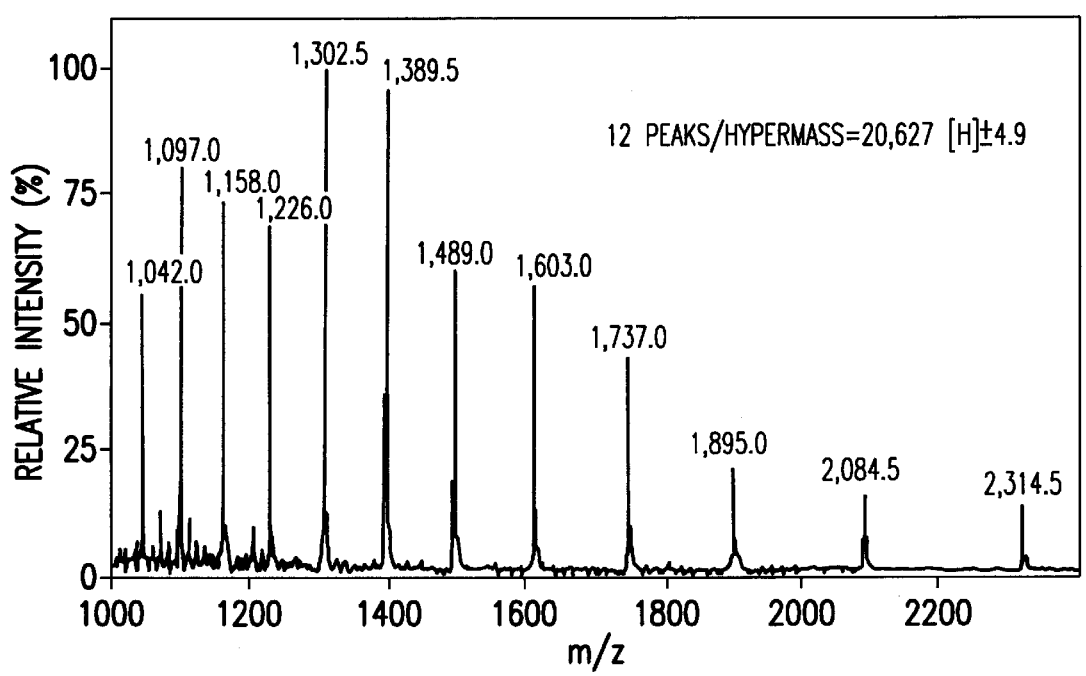

FIG. 25 shows the determination of the molecular mass of EpiD by electrospray mass spectrometry. From the series of multiple charged ions, an average molecular mass of 20,827±5 Da was calculated for EpiD (using the computer program MacSpec 3.22, Sciex). The use of electrospray mass spectrometry for the determination of molecular weights of proteins was described in detail by Jardine (*Methods Enzymol.* 193:441–455 (1990)).

Figure 26:
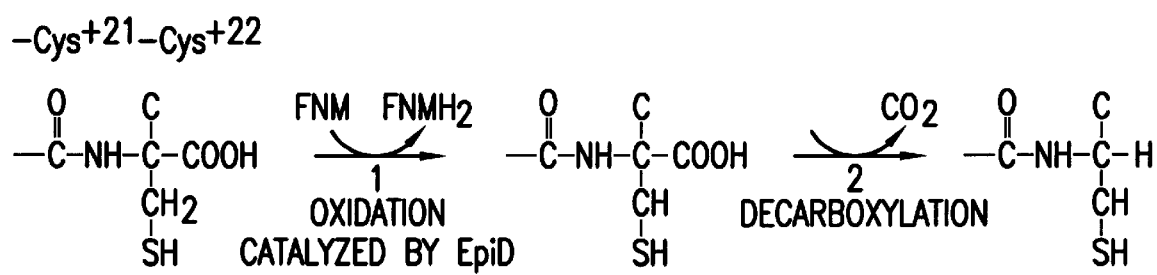

FIG. 26 shows a model of the C-terminal oxidative decarboxylation of unmodified precursor peptide EpiA and the role of flavoprotein EpiD. The C-terminal cysteine residues of the precursor peptide EpiA are shown. In the first reaction, EpiD catalyzes the removal of two reducing equivalents from the C-terminal cysteine residue $Cys^{+22}$. A double bond is formed, and FMN is reduced to $FMNH_2$. The C-terminal carboxyl group is then removed by a decarboxylase reaction either catalyzed by EpiD or occurring spontaneously. The formation of the S-[(Z)]-2-aminovinyl]-D-cysteine structure of mature epidermin can be explained by addition of the thiol group of the C-terminal thioenol to the double bond of didehydroalanine in position +19 in the dehydrated peptide.

Figure 27:
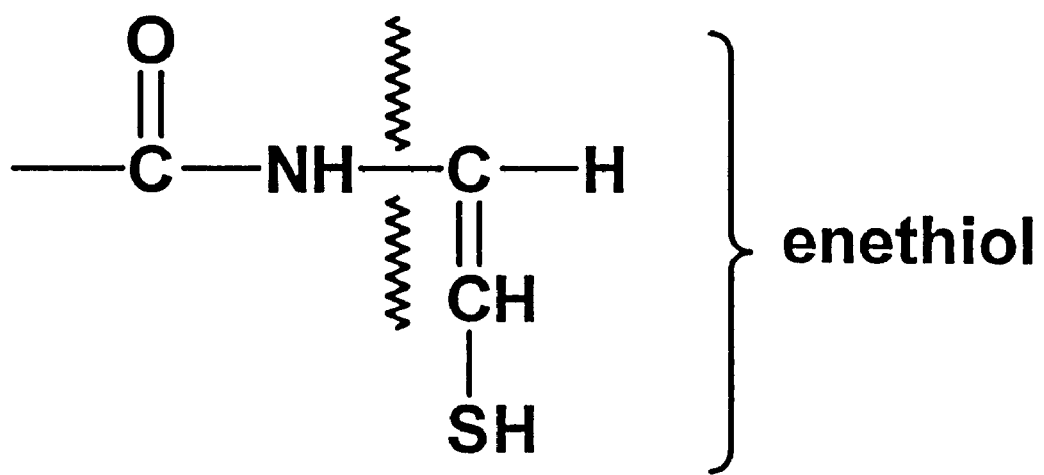

FIG. 27 shows the structure of reaction product of EpiD, wherein the enethiol moiety can be used as a precursor for further chemical reactions.

DETAILED DESCRIPTION OF THE PREFERRED EMBODIMENTS

Importantly, it has been unexpectedly discovered that EpiD can catalyze oxidative carboxylation in the absence of the remaining components of the multienzyme complex.

Broadly speaking the present invention provides in one aspect a bacterial host containing a plasmid, wherein said plasmid codes for a polypeptide which is not normally produced by said host, and wherein said host during cultivation provides a multi-enzyme complex whereby a polypeptide is produced which contains at least one dehydroamino acid and/or at least one lanthionine bridge, said produced polypeptide being foreign to said host. However, as noted above, EpiD can catalyze oxidative carboxylation in the absence of the remaining components of the multi-enzyme complex.

A suitable multi enzyme complex is one which is capable of effecting at least one of the following operations, namely water elimination and sulphide bridge formation; the complex may also effect oxidative decarboxylation.

Suitable hosts for carrying out the process of the present invention are those which, without modification of their genetic material, are capable of producing polypeptides containing a dehydroamino acid residue and/or lanthionine bridge and/or a methyl lanthionine bridge. Examples of such hosts are *Streptococcus lactis, Bacillus subtilis, Streptomyces cinnamoneus*, Streptomyces sp. *Streptoverticullum griseoverticillum, staphylococcus epidermis, Staphylococcus epidermin* strain 5, *Staphylococcus gallinarum* and mutant strains thereof, e.g., a mutant strain of *S. epidermin* DSM 3095 which is incapable of producing epidermin.

Strains which are of special interest are *Staphylococcus gallinarum* (F16/P57) Tü 3928 which has been deposited with the Deutsche Sammlung von Microorganismen under the terms of the Budapest Treaty on May 18, 1988 and has received the depository number Tü 3928 in DSM 4616 and *Staphylococcus zepidermis* DSM 3095 which was deposited by the present applicants with the Deutsche Sammlung von Microorganismen under the terms of the Budapest Treaty on Oct. 26th 1984.

In order to transform a suitable host, a suitable plasmid may be modified by known genetic engineering techniques.

Desirably a plasmid from a host which produces a polypeptide containing at least one dehydroamino acid residue and/or at least one sulfide bridge is treated by modifying or replacing the gene coding for a pre-polypeptide to provide a plasmid coding for a polypeptide foreign to said host and then transforming said host with the altered plasmid.

Any of a variety of methods may be used to replace or modify a gene coding for the pre-polypeptide.

DNA coding for the pre-polypeptide sequence of the desired compound can be prepared by chemical synthesis. Suitable chemical syntheses have been disclosed in *Anal. Biochem.* 121, 365 (1982). The known techniques allow the preparation of polynucleotides, e.g., of up to 60 to 100 bases to be prepared.

Suitable protected nucleotides can be linked by the phosophotriester method Agarwal et al, (*Agnew, Chem.* 84, 489 (1972)), the phosphotriester method (Reese, M., *Tetrahedron* 39, 3, (1983)) or the phosphitetriester method (Letsinger et al., *J. Am. Chem. Soc.* 98, 3655 (1976)) or the phosphoramidite method. The solid phase method allows for simplification of the synthesis of the polynucleotides.

The double stranded DNA can be constructed enzymatically from chemically prepared short but overlapping segments.

For example, overlapping polynucleotide sequences from both DNA strands can be used, which are held together in the correct conformation by base pairing and are then chemically linked by the enzyme DNA ligase (Khorana et al., *J. Biol. Chem.* 251, 565 (1976)).

Another possibility comprises incubating in each case one polynucleotide sequence from the two DNA stands with a short overlapping segment in the presence of the four required deoxynucleoside triphosphates with a DNA-polymerase, for example, DNA-polymerase I, the Klenow fragment of polymerase I or T4 DNA-polymerase, or with reverse transcriptase. The two polynucleotide sequences are thereby held together in the correct arrangement by base pairing and are supplemented with the required nucleotides by the enzyme to give a complete double-strand DNA (Narany et al., *Anal. Biochem.* 121, 365 (1982)).

Another suitable method for obtaining the DNA coding for a polypeptide comprises isolating the DNA from the genomic DNA of a tissue or cell culture or microorganism, lysing the cells e.g. with SDS or proteinase K, or if desired mechanically, and deproteinising the DNA by repeated extraction with phenol.

The RNA can be preferably digested with RNase. The obtained raw DNA is partially digested with suitable restriction enzymes e.g. HaeIII and AluI and fragments isolated and multiplied in a suitable phage or cosmid, e.g. in charon 4A or EMBL-3 phage and assayed for the desired sequences e.g. with a radioactively labeled DNA probe.

The DNA coding for a desired polypeptide can also be obtained by reverse transcription of isolated mRNA into cDNA. This may be the preferred method if the DNA structure is not known. In this method the DNA is obtained from genomic DNA in a cDNA library via the mRNA. The cDNA library comprises the genetic information which is complementary to the mRNA isolated from cells.

To obtain a cDNA library, the mRNA is isolated from cells expressing the desired basic (possibly unmodified) protein. This mRNA is converted into double stranded cDNA.

Standard methods well known in the art are applied in the preparation of mRNA. The cell membrane is broken and the cell content released from which the mRNA is isolated. The cell membrane is preferably broken by physical methods or lysis with detergents such as SDS, guanidine thiocyanate, definite salt conditions or homogenization, preferably by mixing. The mRNA is isolated by the standard methods of phenol extraction, ethanol precipitation, centrifugation and chromatography, preferably a combination of several methods. Centrifugation is preferably done over gradients, for example over a CsCl gradient. For chromatography, preferably columns are used, especially oligo-dT columns.

The total mRNA can be converted directly into Ds-cDNA following the methods of the art. Preferably the mRNA coding for a desired polypeptide is further enriched using several techniques, such as electrophoresis, chromatography and centrifugation, preferably sucrose gradient centrifugation.

Fractions containing mRNA coding for a desired polypeptide can be detected by various methods, such as in vivo or in vitro translations, followed by detection of a relevant activity or, when the nucleotide sequence is known, by hybridization with an oligonucleotide probe.

In vivo translation systems can be prokaryotic or eukaryotic systems. A preferred in vivo translation system is the Xenopus laevis oocyte system (see *Maniatis* et al, *Molecular Cloning, A Laboratory Manual,* Cold Spring Harbor Laboratory (1982)). In vitro systems are, for example, wheat germ and rabbit reticulocyte lysates, both of which are commercially available.

From any pool of mRNA derived from unfractionated or fractionated mRNA, ds-cDNA can be obtained by the well known methods of the art (preferred general methods are described in Maniatis et al. (supra), Okayam and Berg, *Molecular and Cell Biology* 2, 161–170 (1982) and Heidecker, *Nucleic Acid Research* 11, 4891–4906 (1983)). In general, the mRNA is converted first to ss-cDNA using reverse transcriptase or DNA-polymerase I (Klenow fragment). Two methods are alternatively used for priming the synthesis of the ds-cDNA. The first method was the natural loop formation of the ss-cDNA. The second method is that of tailing the ss-cDNA with a homopolymeric tail such as poly-dC or poly-DT.

The mRNA fraction of which the corresponding polypeptide shows the highest activity in the detection system is transcribed into the complementary cDNA by methods well known in the art. The mRNA and oligo-dT as a primer are mixed, dNTPs are then added as starting material and the synthesis of the cDNA-mRNA hybrid molecule is realized by the enzyme reverse transcriptase. The RNA molecules are degraded by addition of NaOH. DNA polymerase is admixed, preferably the Klenow fragment of the DNA polymerase I, and the mixture is incubated at a suitable temperature, preferably 12–15° C. The mixture is incubated with nuclease SI and the ds-cDNA corresponding to the mRNA coding for a desired polypeptide is obtained.

For amplification the obtained ds-cDNA can be spliced into suitable vector e.g. the plasmid pUC-KO and the obtained hybrid vector multiplied by use of a suitable host, e.g. *E. Coli* HB101. Reisolation of the hybrid vectors, and recovering the isolated cDNA therefrom allows a structure determination of the DNA coding for a desired polypeptide.

Preparation of a Hybrid Vector

A hybrid vector of the invention can be prepare by splicing a DNA coding for a polypeptide of the desired sequence into a suitable vector.

Suitable vectors are carriers for integrated passenger DNA, which can be used to transform a host microorganism.

Suitable as vectors are plasmids derived from microorganisms which in an untransformed state produce polypeptides which contain dehydroamino and/or sulfide groups. Suitable vectors carry the insert DNA at a defined position.

In general, such vectors may contain a replicon and a control sequence, i.e. a promoter, which are derived from the host cell or a species compatible with the host cell in which they are used. The vector ordinarily carriers a replicon site and may contain sequences (marker genes) which are capable of providing phenotype selection in transformed cells. Suitable marker genes may provide antibiotic resistance or resistance to heavy metals or they may complement a genetic defect of the host. Further useful sequences in such vectors are enhancer and activator sequences.

One suitable starting vector is a 54 Kbp plasmid pEpi32 from the strain *Staphylococcus epidermis* DSM 3095. This plasmid, which is characterized below, contains the epiA gene encoding for a 52-prepeptide, which is processed to a tetracyclic 21-peptide amide antibiotic. A vector carrying a passenger DNA is designated a hybrid vector.

The desired DNA is spliced into the starting vector by conventional methods.

A starting plasmid for example can first be linearised by a suitable restriction enzymes, e.g. the plasmid pEpi32 by HindIII, BamHI and EcoRI, then d/G-tailed in the presence of dGTP and the terminal deoxynucleotidyl transferase. The double stranded cDNA insert is dC-tailed in the presence of dCTP and terminal deoxynucleotidyl transferase. Combining both cDNA and vector results in the hybrid vector. Bacteriophages, such as lambda, are preferred for constructing genomic libraries. The lambda cloning systems are described by Maniatis (supra). The suitable vector DNA is digested to completion with the appropriate restriction enzyme, and the left and right arms are separated from the central fragments by velocity gradient centrifugation or gel electrophoresis. Another method is to digest parts of the stuffer fragments with restriction enzymes which lack recognition sites in the left and right arms. The isolated genomic DNA can be partially digested to fragments of 13–20 kb in length. Afterwards the arms are ligated with the fragments of foreign DNA having termini compatible with those of the arms.

The appropriate DNA insert is recloned from the original vector used for the original cloning, into a suitable expression vector. To this end appropriate restriction enzymes are used, possibly in combination with oxonucleones, to produce the desired DNA fragments.

The DNA insert may be subcloned into a multiple site of a suitable well known plasmid vector e.g. derivatives of pC194, pT181 and pUB110 at the restriction sites HindIII/BamHI/EcoRI.

The method of the invention can thus be used to prepare derivatives of known peptides and hormones, in which a cysteine residue in the unmodified peptide is replaced by sulfide-bridged amino acids and serine and thiamine are replaced by corresponding dehydroamino acid residues.

These fragments are integrated into an appropriate expression vector by using the cohesive ends directly or by the addition of appropriate chemically synthesized oligonucleotide bridges. For the modification of the ends for example HindIII and BglII can be used. The method is not limited to any special restriction enzymes. Any desired link can be made between the expression vector and the DNA insert using suitable restriction enzymes in combination with chemically synthesized oligonucleotide.

Appropriate DNA inserts can also be obtained which code for polypeptide having site directed mutagenesis.

A variety of methods may be used to induce mutations of underlying DNA so as to prepare the desired mutants.

One method may comprise first inserting a fragment of a native or basic gene, containing sequences coding for the region to be mutated, into the replicative form of a phage, e.g. phage MI3mp8 to form MI3mp8PA. A synthetic oligonucleotide, complementary to the inserted sequences but containing one or more nucleotide triplets which code for the amino acid to be substituted, is then annealed to the single stranded form of MI3mp8A to form a double stranded region. This region serves as a primer for DNA polymerase I synthesis of the remaining complementary strand. After replication and identification, the mutant sequence may be further modified or used to construct a suitable vector for expressing the mutated polypeptide.

In the work carried out on epidermin a wobbled DNA probe 5'GTG(A)CAT(G/A)ATG(A)AAT(C)TT-3' deduced (SEQ ID NO: 36) from a suitable pentapeptide segment of the proposed pre-sequence of epidermin LysPheIleCylThr was prepared. This DNA probe was hybridized against plasmid DNA from *S. epidermin* DSM 3095.

Restriction analysis of the isolated plasmid reveals seven DNA fragments with EcoRI (16, 11, 10, 6.5, 5.5., 3.5 and 2.5 kbp), nine DNA fragments with HindIII (17, 14, 10, 5.3, 2.8, 1.8, 0.8, 0.6 and 0.5 kbp) and five DNA fragments with BamHI (20, 19, 10, 3 and 1 kbp).

A 5.4 kbp HindIII fragment was subcloned and subjected to rehybridization whereby the structure gene epiA was located within a 2.2 kbp EcoRI/BglII fragment.

As a mixture of 24 different 14-mers was used as a hybridization probe. The probe was applied in a 30-fold excess as a sequencing primer in accordance with the techniques described in Novick et al. *Ann. N.Y. Acad. Sci.* 182, 279–294 (1971), Southern, *J. Molec. Biol.* 98, 503–517 (1975) and Heinrich et al., *Molecul. gen. Genet.* 209, 563–569 (1987). The peptide sequence of epidermin allowed identification of the open reading frame. A single methionine codon is in appropriate distance to a Shine-Dalgarno sequence. The structural gene of pre-epidermin terminates at the TAA stop codon, hence pre-epidermin consists of 52 amino acids (FIG. 1) and it is processed to the epidermin between Arg–1 and Ile$^{+1}$. Thus, as can clearly be seen, pre-epidermin is not a degradation product of a larger protein but is coded by a distinct structural gene.

Thus, it is apparent that, unexpectedly, the precursor protein of the antibiotics are coded by distinct structural genes.

Figure 2A:
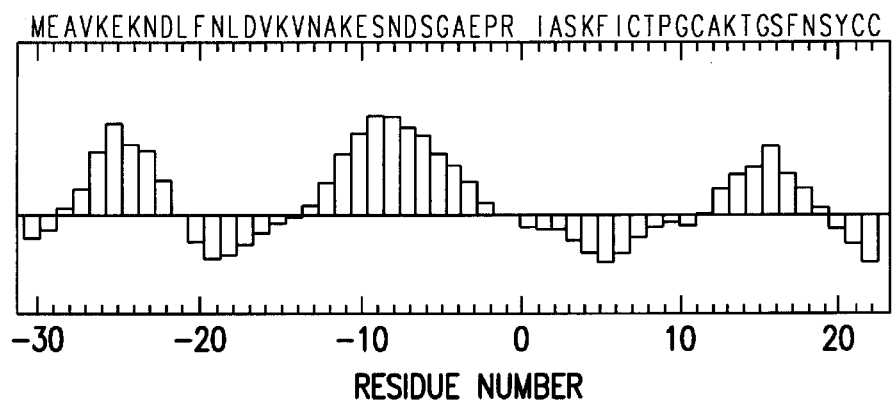
FIGS. 2A–F depict a prediction plot for pre-epidermin using a Hyron program, in which the respective bar charts show: (a) flexibility; (b) hydropathy; (c) hydrophilicity; (d) propensities for turn; (e) β-sheet; and (f) α-helix conformation.
Figure 2B:
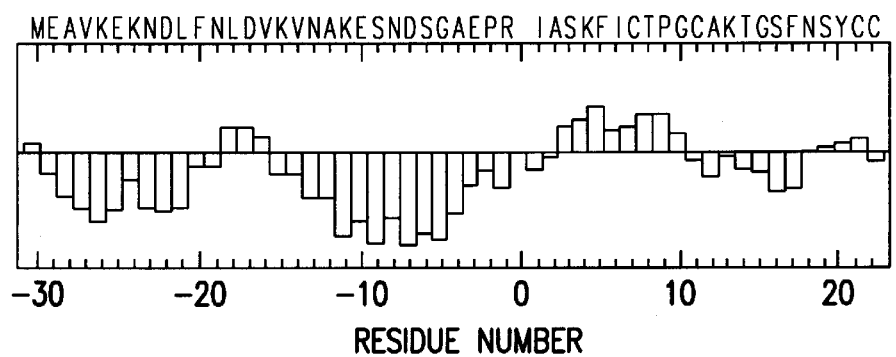
Figure 2C:
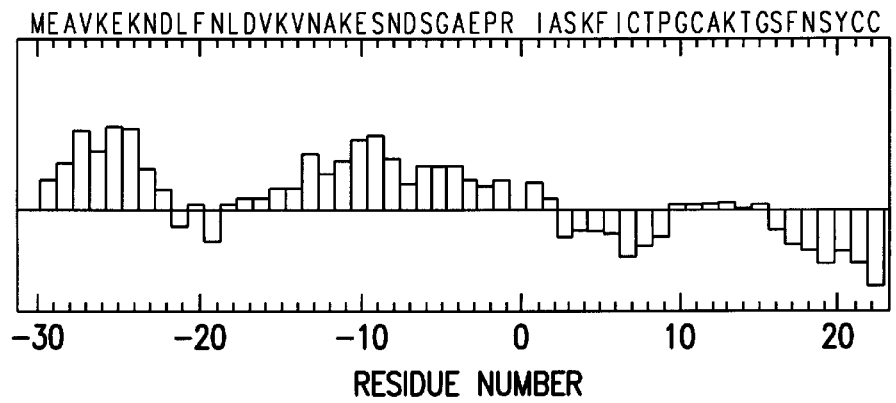
Figure 2D:
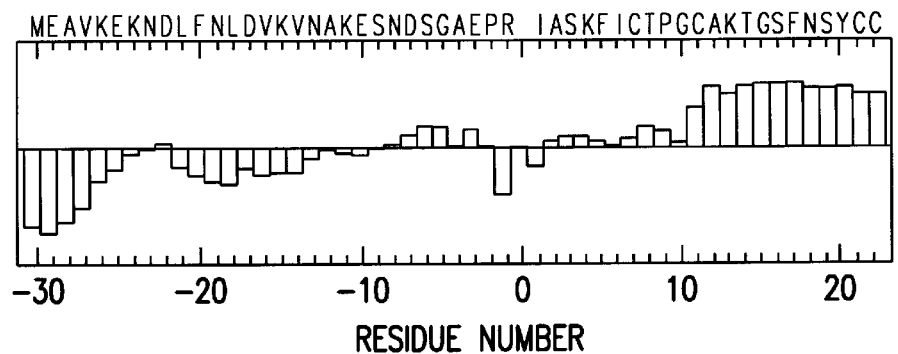
Figure 2E:
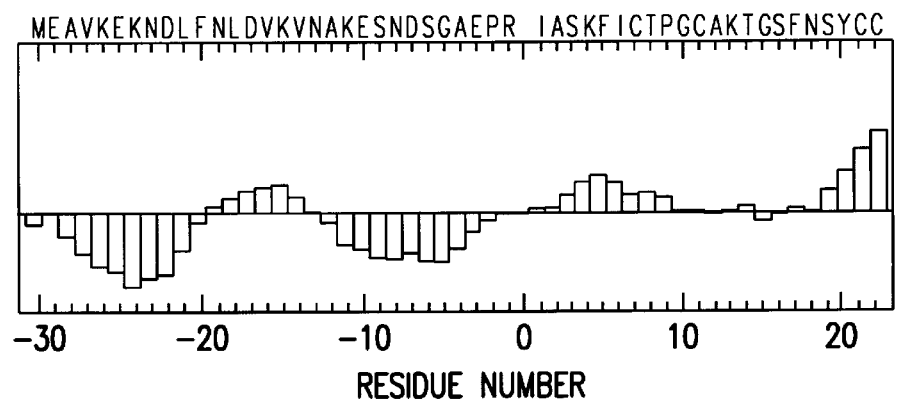
Figure 2F:
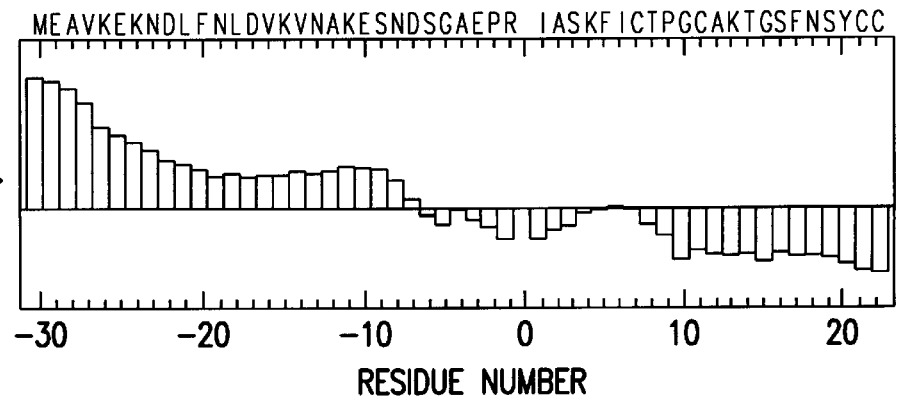
Figure 2G:
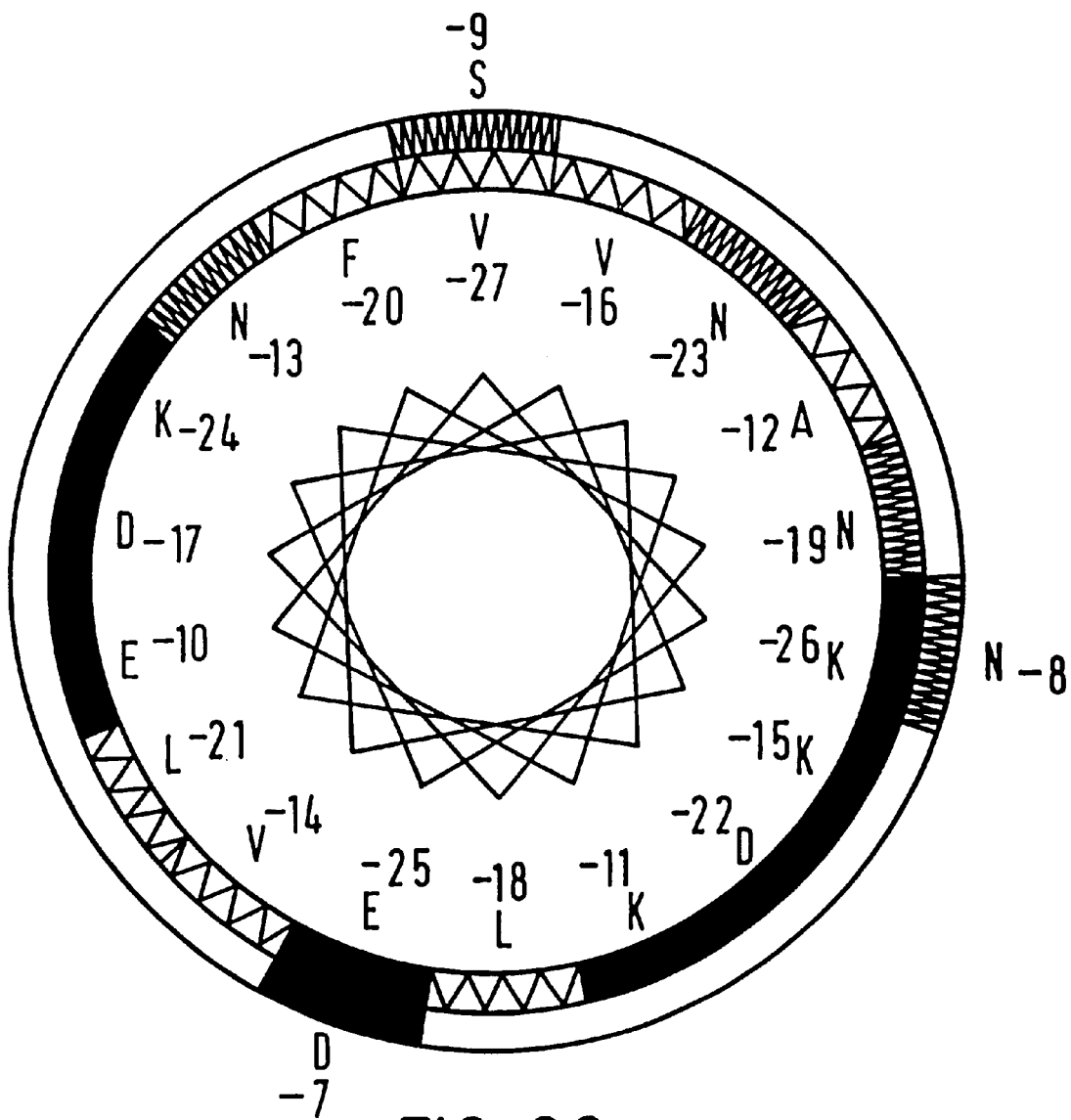
FIG. 2G depicts a helix wheel plot for pre-epidermin showing that the N-terminus may partially adapt an amphophilic α-helical conformation in an appropriate environment.

A combination of prediction profiles for secondary structure (α, β, turns), flexibility, hydropathy, hydrophilicity (FIGS. 2A–F) and helix wheel plot were made using a Hycon program (FIG. 2G). A high α-helix probability is predicted for pre-epidermin –30 to –8 whereas the C-terminal part 1–22 which corresponds to pro-epidermin exhibits very high turn probability. Moreover, the prediction plot shows clearly, that the N-terminus –30 to –1 highly hydrophilic, whereas the C-terminal part is more lipophilic. The N-terminal part –30 to –8 seems to fold partially into an amphophilic α-helix.

The N-terminal segment of pre-epidermin –30 to –1 does not contain any cysteine residues, whereas the C-terminal segment 1–22 contains the four cysteine residues, involved in sulphide bridge formation. Sequence –30 to –1 included many cleavage sites for endoproteases whereas even in the pre-epidermin state, sequence 1–22 is highly resistant to proteolytic degradation.

The mature antibiotic can only be attacked by trypsin at Lys in position 13. The processing site Arg$^{-1}$-Ile$^{+1}$ is hydrophilic and accessible, due to the turn forming Pro$^{-2}$ residue.

Figure 3:
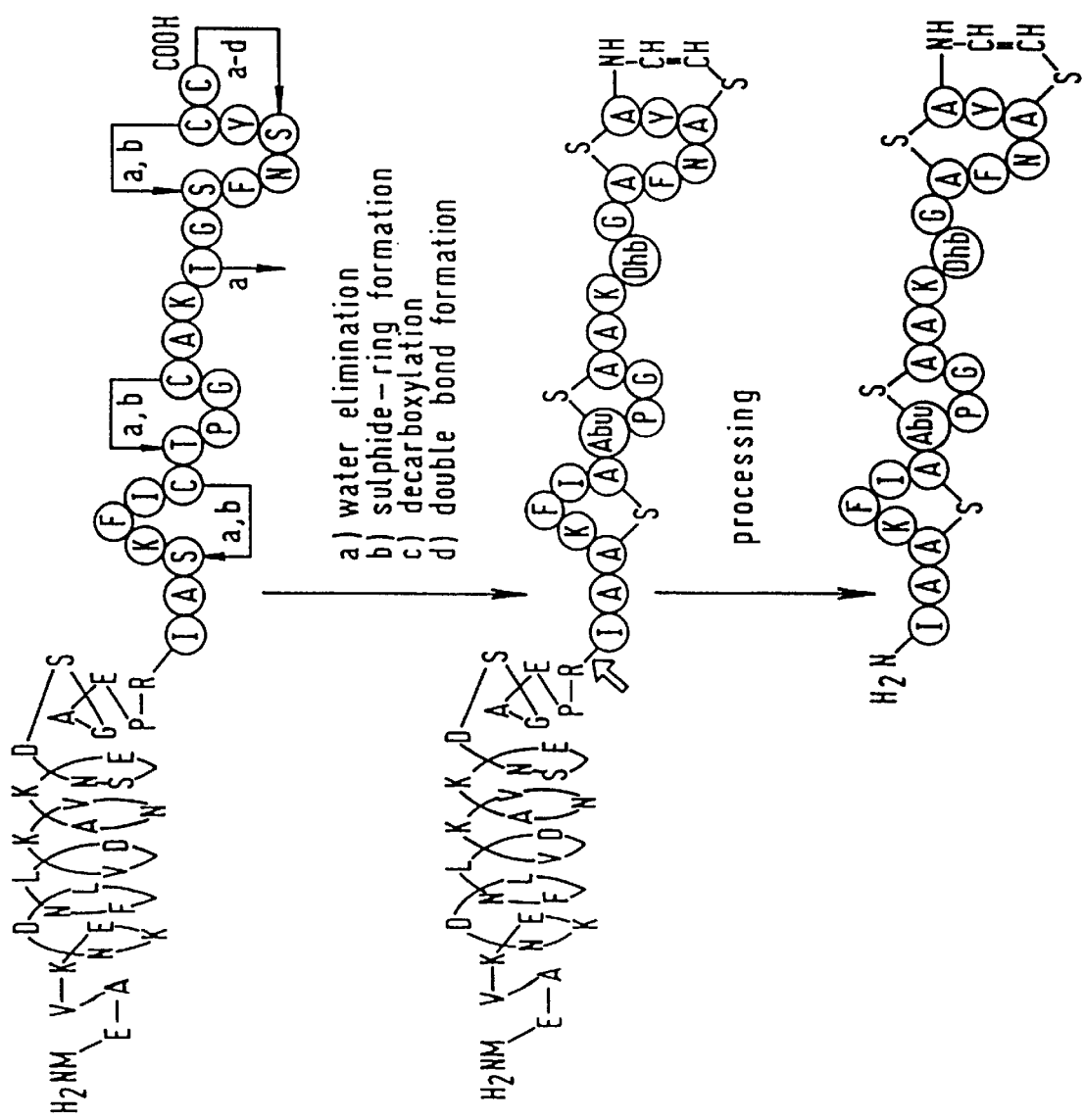
FIG. 3 depicts a postulated naturation procedure for epidermin. The translated polypeptide (pre-epidermin) consists of 52-amino acid residues. Structure predictions indicate a partially α-helical N-terminus from which residues −30 to −10 may form an amphilphilic α-helix conformation. Water elimination occurs at the indicated Ser and Thr residues (a). With the exception of $Thr^{+14}$, water elimination is followed by sulphide ring formation (b) and at the C-terminus, decarboxylation (c) and double bond formation (d) to produce proepidermin. The pro-epidermin structure is then processed by proteolytic cleavage to produce epidermin.
Figure 4:
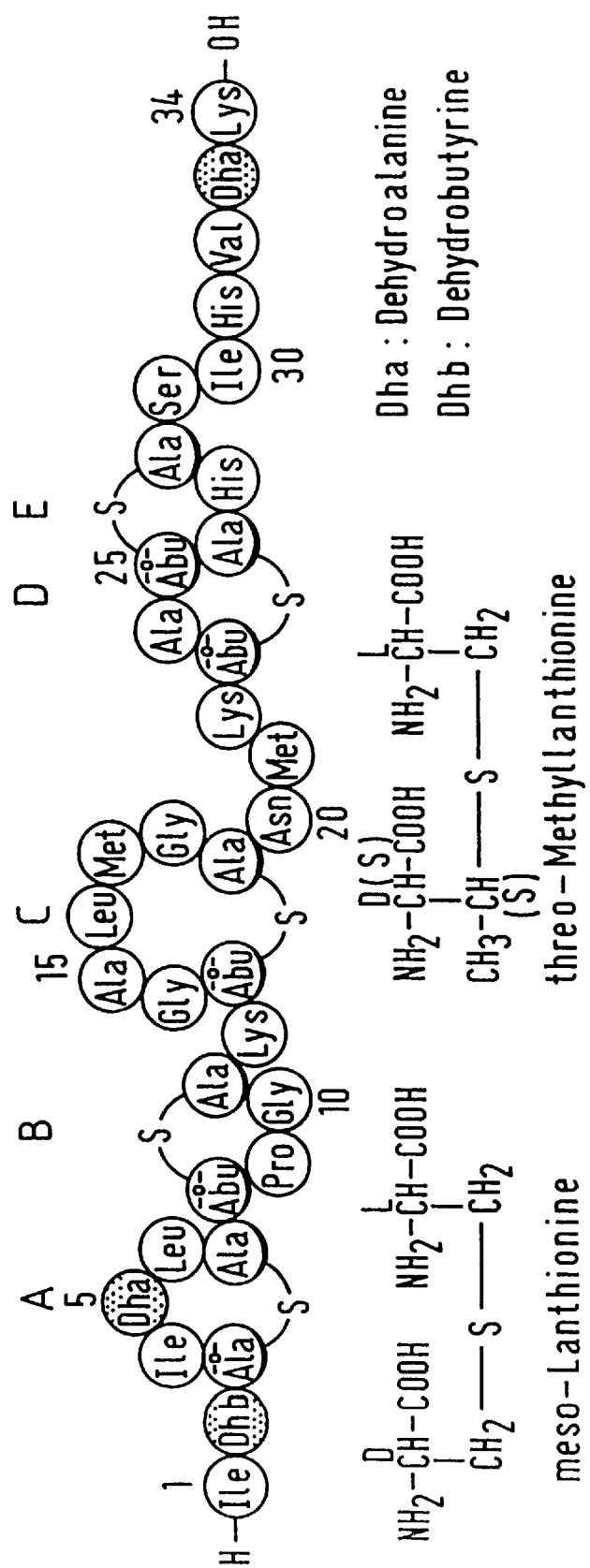
FIG. 4 depicts the structure of epidermin. The ring structures are designated as A, B, C, D and E. The structures of the amino acids mesolanthione and threo-methyllanthione, are set forth.

The various enzymatic reactions which occur in the production of the antibiotics such as epidermin include modifications of the pro-polypeptide part 1–22; cleavage of the N-terminal prepeptide fragment –30 to –1 and secretion of the matured antibiotic (see FIGS. 3 and 4).

The enzymatic modifications occur before cleavage of the prepeptide fragment. Enzymatic modification includes the elimination of water from Ser and Thr residues in position 5, 16, 19 and 8, 14 respectively to form dehydroalanine and dehydrobutyrine residues. Addition of thiol groups of Cys residues in position 2, 11, 21 and 22 to the C═C double bonds, also occurs, yielding the meso-lanthionine or (2S 3S, 6R) -3-methyl-lanthionine bridges. In addition, decarboxylation of residue 22 and double bond formation yields the C-terminal S-(2-aminovinyl)-D-cysteine. The reaction of C-terminally situated cysteine thiol groups with N-terminally located dehydroamino acids occurs with complete stereo-specificity in epidermin, nisin and subtilin. Accordingly, during modification these elimination-addition reaction imply a reversal of configuration of the Cα carbon atoms at pre-epidermin residues L-Ser and L-Thr to give D-configured Cα atoms. On the other hand, the L-configuration of the cysteine halves is still maintained.

The four sulphide rings are also formed, subsequently at the same catalytic site, which is supported by the interaction with the N-terminal amphophilic α-helix. Only Thr$^{+14}$ dehydrates without finding a cysteine. This position (Lys$^{+13}$-Dhb$^{+14}$) constitutes the enzymatic cleavage site at which trypsin inactivates the antibiotic epidermin. During sulphide ring formation C-terminal rigidity and hydrophobicity increases and may favor interaction of pro-epidermin with the lipid bilayer and may induce translocation.

Finally, the hydrophilic α-helical N-terminus –30 to –1 is cleaved by a specific protease at the characteristic cleavage site described above.

Using the techniques described above plasmids coding for lantibiotics can be modified either by mutation of the gene coding for the respective polypeptide or by replacement of such a gene by a gene coding for a different polypeptide and used to transform the original host or a different host, provided such host also, in its native state, is capable of expressing a lantibiotic.

Generally speaking, where the original functional gene codes for a pre-sequence, as discussed above for example in the case of epidermin, the DNA sequence coding for such a pre-sequence may be retained in the modified plasmid; in this case the DNA-sequence for the new, or mutated pro-polypeptide will be positioned directly upstream of the pre-sequence DNA similarly to the original pro-polypeptide sequence.

Cultivation of a bacterial host according to the present invention may be carried out under conventionally used cultivation conditions as described for instance in our co-pending British Patent Application No. 8811760.1 which was filed on May 18th 1988 and in European Patent Application Publication No. 0 181 578. Purification and isolation of the desired protein may also be carried out using the techniques or suitable modifications thereof described in the foregoing patent applications for epidermin and gallidermin, including the use of adsorbents, ion-exchange resins and if desired HPLC.

The process of the invention can be applied to the formation of novel compounds for experimental purposes, or to the formation of known compounds or derivatives of known compounds in new hosts. For instance a plasmid containing the gene coding for epidermin can be used to transform the species *Streptococcus lactis* to produce epidermin from that host, or the gene coding for Gallidermin (see our co-pending British Patent Application referred to above) can be used to replace the gene coding for the pro-polypeptide for epidermin in e.g. plasmid pEpi32 and used to transform *staphylococcus epidermis* DSM 3095 to produce gallidermin from this host. Similarly other biologically active peptide derivatives containing dehydroamino acid residues and/or lanthionine bridges and/or methyl-lanthionine bridges can be produced, such as derivatives of hormones such as human insulin, oxytocin, vasopressin, peptide antibiotics, hormone inhibitors such as elastase inhibitor and fibrinolytically active agents such as human tissue plasminogen activator. Such derivatives, as well as retaining biological activity of the parent compound can have increased stability and improved half-lives.

Ideally the DNA coding for the desired pro-polypeptide should include codons for cysteine and serine and/or for cysteine and threonine for the formation of thioether bridges.

For relatively short chain polypeptides these respective codons should normally be no more than eight and preferably no more than six codons apart, inclusive, although it is envisaged that, depending upon the steric conformation of the final polypeptide molecule much greater spacing is possible.

In respect of the formation of dehydroamino acids these will usually be derived from serine and threonine and, accordingly the DNA coding for the desired pro-polypeptide will include codons for such amino acids.

Figure 5A:
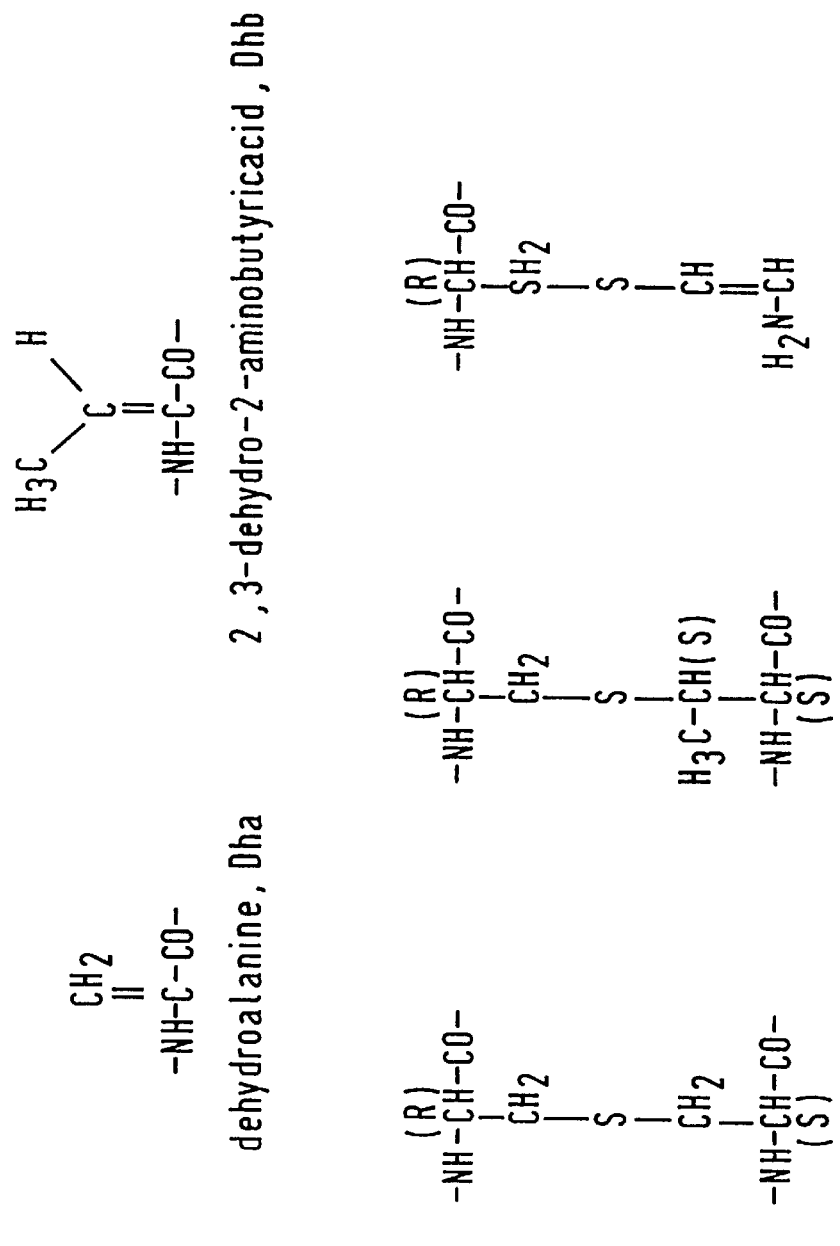
FIG. 5A–B depict examples of unusual amino acids which are found in lanthione antibiotics and which can be formed in peptide products using the method of this invention.
Figure 5B:
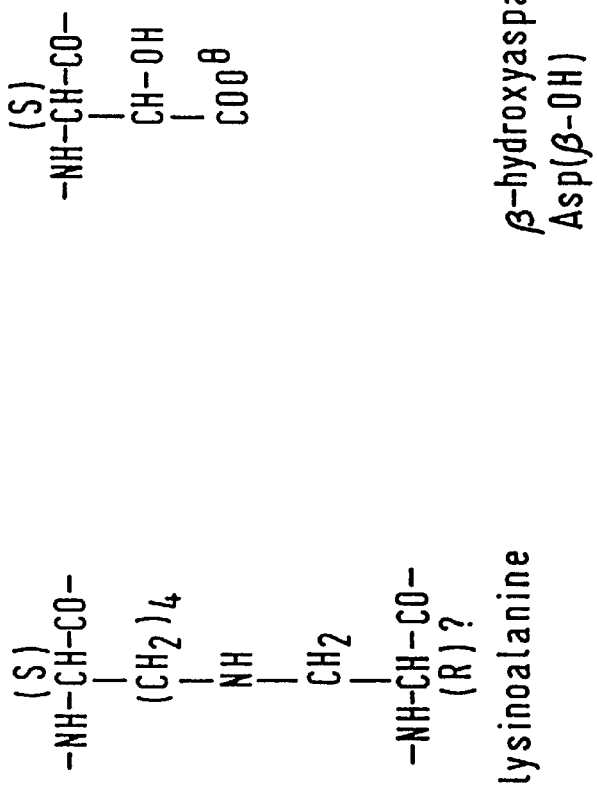

Among the unusual amino acids which may be present in a polypeptide produced according to the present invention are, dehydroalanine, 2,3-dehydro-2-aminobutyric acid, meso-lanthionine, (2S, 3S, 6R)-3methyl-lanthionine, S-(2-(Z)-aminovinyl)-D-cysteine, lysinoalanine and β-hydroxyaspartic acid; the structure of these residues are shown in FIG. 5.

It was unexpectedly found that the multi enzyme complex responsible for the posttranslational modification of pre-epidermin is located on the 54 kb plasmid pTü32 of *staphylococcus epidermis* Tü 3298/DSM 3095.

The six genes (ORFs) responsible for the production of epidermin are designated herein epi A, B, C, D, Q and P and are clustered within 8 kb and the proteins for which they code are designated Epi A, B, C, D, Q and P respectively; epi A encodes the 52 amino acid-long pre-epidermin. As described below, epi B, C and D are involved in the four enzymatic modification reactions (i) water elimination by a serine/threonine dehydratase, (ii) sulfur addition by a lanthinonine synthase, (iii) C-terminal decarboxylation by a cysteine decarboxylase and (iv) double bond formation. Epi P protein is believed to be responsible for cleaving the mature epidermin from the N-terminal leader peptide, based on its striking homologies with the essential domain of serine proteases (Koide et al., *J. Bacteriol.* 167:110–116 (1986); Meloun et al., *FEBS Lett.* 183:195–200 (1985); and Stahl et al., *J. Bacteriol.* 158:411–418 (1984)) while Epi Q is believed to be a regulatory protein regulating epidermin biosynthesis, based on its distinct homology to the pho B gene of *E. coli* (Makino et al., *J. Mol. Biol.* 190:37–44 (1986)), the fact that both proteins are of a similar size with 205 (epi Q) and 229 (pho B) amino acid residues, the observed homology of 24.2% extending over the 153 C-terminal amino acid residues and the hydrophilicity plots of both proteins.

As a result of the unexpected finding of the entire genetic information for the epidermin biosynthesis and the elucidation of the genes for the proteins epi B, C, D, Q and P, it is now possible to obtain the isolated DNA coding for the proteins, and to construct plasmids containing one or more of these genes so that upon cultivation of a host containing such plasmids one of these proteins alone or predetermined combinations of the proteins may be expressed and subsequently isolated.

The present invention therefore includes DNA sequences encoding respectively for the protein Epi B or Epi C, or Epi D, or Epi P or Epi Q. These sequences may be isolated DNA either single or double stranded, obtained by cleavage of and isolation from pTü32 in known manner or obtained by chemical synthesis or any other conventional procedure. The DNA may also be integrated in a plasmid, suitably an expression plasmid and under the control of a promoter regulator; such constructs when transformed into a suitable host which is then cultivated will express the protein Epi B, Epi C, Epi D, Epi P or Epi Q or combination of these proteins according to which DNAs were ligated into the plasmid. Alternatively plasmid pTü32 may be treated with suitable restriction nucleases to excise one or other of the DNA sequences, followed by religation after any necessary modification of the free ends of the digested plasmid, so as to create a modified plasmid containing DNA sequences coding for predetermined ones of epi B, C, D, P and Q.

A further variant comprises the substitution of the gene coding for epidermin in pTü32 with a DNA sequence coding for a predetermined amino acid sequence whereby cultivation of a suitable host with the modified plasmid will result in expression of a protein different from epidermin.

It is thus possible to substitute a DNA sequence encoding for gallidermin or mutant epidermin or other lantibiotic or other protein, for the epidermin coding sequence in pTü32 whereby the resulting plasmid can be transformed into a suitable host which may be a host normally incapable of producing a lantibiotic or any of the proteins Epi B, C, D, P or Q and to cultivate the host under conditions whereby the substituted DNA sequence and the genes epi B, C, D, P and Q are expressed, so as to obtain a protein which is gallidermin, mutant epidermin or other protein containing at least one structural feature of a lantibiotic.

Alternatively the genes coding for the proteins Epi B, C, D, P or Q may be inserted into a suitable vector, together with a DNA sequence encoding a predetermined amino acid sequence, the genes coding for the Epi proteins and the predetermined amino acid sequence being operably connected with suitable promoter regulator functions, the resulting plasmid being transformed into a suitable host which may be a host normally incapable of producing a lantibiotic or any of the proteins Epi B, C, D, P or Q, and the host cultivated so that the inserted genes cause the expression of a protein derived from said predetermined amino acid sequence but containing a lantibiotic structural feature, which protein may be gallidermin, epidermin, mutant epidermin, or another protein.

The present invention thus also includes within its scope DNA sequences capable of hybridizing, preferably under stringent conditions, with the DNA sequences described herein and coding for proteins having substantially the activity of the proteins Epi B, C, D, P or Q. Stringent hybridization conditions select for DNA sequences of greater than 85% or, more preferably, greater than about 90% homology. Screening of the cDNA library may be carried out under highly stringent conditions according to the method described in European Patent Application No. 88 119 602.9 and Kashima et al. (*Nature* 313:402–404 (1985)). The DNA sequences capable of hybridizing under stringent conditions with the DNA sequences disclosed in the present application may be, for example, allelic variants of the disclosed DNA sequences, may be naturally present in the particular microorganism but related to the disclosed DNA sequences, or may derived from other sources. General techniques of nucleic acid hybridization are disclosed by Maniatis, T. et al., In: *Molecular Cloning, a Laboratory Manual*, Cold Spring Harbor, N.Y. (1982), and by Haymes, B. D. et al., In: *Nucleic Acid Hybridization, a Practical Approach*, IRL Press, Washington, DC (1985), which references are herein incorporated by reference. The proteins Epi B, C, D, P and Q are valuable and interesting new reagents potentially useful in the preparation of novel proteins or other substances containing structural features such as dehydroalanine, dehydrobutynine, meso-lanthionine, 3-methyl-lanthione, and S-(2-aminovinyl)-D-cysteine.

As such, they may be utilized as isolated proteins, or as chemical catalytic reagents in chemical synthesis procedures to investigate the extracellular processing of proteins by such enzymes.

The invention also relates to the proteins Epi B, C, D, P and Q in substantially pure form. By the term "substantially pure" is intended that the protein is free of the impurities that are naturally associated therewith. Substantial purity may be evidenced by a single band by electrophoresis.

The polypeptides of the invention may be isolated and purified from the above-described recombinant molecules in accordance with conventional methods, such as extraction, precipitation, chromatography, affinity chromatography, electrophoresis, or the like. Preferably, the polypeptides are produced as part of a fusion protein which further comprises an auxiliary protein. Such auxiliary which facilitates the isolation and purification of the polypeptide of interest. Such auxiliary proteins include, for example, typical secretion signals, the maltose binding protein from *E. coli*, or protein A. Methods for preparing fusion proteins comprising protein A, the purification thereof by immunoaffinity chromatography, and the cleavage thereof to release the protein of interest is taught, for example, in PCT Application Publication No. WO84/03103 (1984).

A necessary condition to permit cleavage of the fusion protein is that it contains a unique cleavage site which may be recognized and cleaved by suitable means. Such a cleavage site may be a unique amino acid sequence recognizable by chemical or enzymatic means and located between the desired protein and the auxiliary protein. Such a specific amino acid sequence must not occur within the desired protein or auxiliary protein. Examples of enzymatic reagents include proteases such as collagenase which may recognize the amino acid sequence NH$_2$-Pro-X-Gly-Pro-COOH, (SEQ ID NO: 37) wherein X is an arbitrary amino acid residue, e.g. leucine; chymosin (rennin) which cleaves the Met-Phe bond; kallikrein B which cleaves on the carboxyl side of Arg in X-Phe-Arg-Y; (SEQ ID NO:⇒) enterokinase which recognizes the sequence X-(Asp)$_n$-Lys-Y, (SEQ ID NO: 39) wherein n=2–4, and cleaves it on the carboxyl side of Lys; thrombin which cleaves at specific arginyl bonds. Examples of chemical agents which may be used to cleave the fusion proteins include cyanogen bromide which cleaves after Met; hydroxylamine which cleaves the Asn-Z bond wherein Z may be Gly, Leu or Ala; formic acid which in high concentration (~70%) specifically cleaves Asp-Pro.

EpiD has been purified and identified as a flavoprotein with flavin mononucleotide as coenzyme (Kupke, T. et al., *J. Bacteriol.* 174:5354–5361 (1992)). The EpiD* gene of the epi-mutant *S. epidermis* Tü3298/EMS 11 has been expressed as a maltose-binding protein (MBP)-EpiD* fusion protein in *Escherichia coli*. Unlike MBP-EpiD, this fusion protein MBP-EpiD* cannot bind the flavin coenzyme. DNA sequencing of EpiD* had identified a point mutation that led to replacement of Gly$^{93}$ with Asp (Kupke, T. et al., *J. Bacteriol.* 174:5354–5361 (1992)).

The substrate peptide EpiA and the mutated peptide EpiAR-1Q have been purified by factor Xa cleavage from MBP fusions. The mutant K-EpiA has also been purified (Kupke, T. et al., *J. Biol. Chem* 269:5653–5659 (1994)). The identity of purified EpiA and EpiAR- 1Q have been confirmed by electrospray mass spectrometry (ES-MS) and amino acid sequencing (Kupke, T., et al, *FEMS Lett.* 112:43–48 (1993)). EpiA consists of an NH$_2$-terminal leader peptide (amino acids −30 to −1 ) and a COOH-terminal proepidermin (amino acids +1 to +22) (Schnell, N., et al., *Nature* 333:276–278 (1988)). The last two amino acids of EpiA are cysteine residues. EpiAR-1Q contains a mutation in the cleavage sequence of the EpiA leader, while K-EpiA includes an additional positive charge at the amino terminus of the leader (Kupke, T. et al., *J. Biol. Chem* 269:5653–5659 (1994)).

Recently, it has been demonstrated that under reducing conditions, EpiD reacts with unmodified precursor peptides EpiA and EpiAR-1Q and with the COOH-terminal proepidermin fragment of EpiA as shown by reversed phase chromatography and ES-MS (Kupke, T., et al., *J. Biol. Chem.* 269:5653–5659 (1994)). A decrease in mass by 46 Da was observed, and an increase in absorbance at 260 nm of the modified peptides. Sequence analysis of modified proepidermin indicates that one of the two last cysteine residues of proepidermin is modified by EpiD. A model, shown in FIG. 26, has been proposed wherein EpiD catalyzes the removal of two reducing equivalents from the side chain of the COOH-terminal cysteine residue (Kupke, T., et al., *J. Biol Chem.* 269:5653–5659 (1994)). A double bond is formed, and the flavin mononucleotide coenzyme is reduced. The COOH-terminal carboxyl group is then removed by a decarboxylation reaction resulting in the COOH-terminal enethiol side chain. The oxidated and decarboxylated peptide is unstable and is nonenzymatically converted to less hydrophobic peptides. The reaction is inhibited by Zn$^{2+}$, and the oxidative decarboxylated peptide is probably stabilized by Zn$^{2+}$(Kupke, T., et al, *J. Biol. Chem.* 269:5653–5659 (1994)). It has been concluded that the oxidoreductase EpiD is involved in formation of the COOH-terminal S-[(Z)-2-aminovinyl]-D-cysteine.

Furthermore, fusion proteins comprising EpiD have also been shown to catalyze oxidative decarboxylation. In particular, it has been demonstrated that a fusion of EpiD and Maltose binding Protein (MBP-EpiD) catalyzes the oxidative decarboxylation of EpiA, yielding the same reaction products as does EpiD (Kupke et al., *J. Biol. Chem.* 269(8): 5653–5659 (1994)).

As a reaction between EpiA and EpiD is only observed in the presence of a reducing agent such as dithiothreitol (DTT), β-mercaptoethanol, and glutathione, clearly either EpiA or EpiD (which has four oxidizable cysteine residues) have to be in the reduced state (Schnell et al., 1992; Kupke et al., *J. Biol. Chem.* 269(8):5653–5659 (1994). In the in vitro assay, reduced EpiD-FMNH$_2$ is probably reoxidized to EpiD-FMN by oxygen. However, the hydrogen acceptor in vivo is unknown (Kupke et al, 1994). It will be understood by those of skill in the art that other reducing agents a substance capable of reducing disulphide bridges besides DTT can be used in the oxidative decarboxylation of peptides by EpiD in vitro. Such reducing agents include, but are not limited to, β-mercaptoethanol and glutathione (γGlu-Cys-Gly).

The present invention relates to further characterization of this novel posttranslational modification reaction. One major question regarding posttranslational modifications concerns the specificity of the processing reactions in selecting only a few or sometimes even only one residue for modification (Yan, S. C. B., et al., *Trends Biochem. Sci.* 14:264–268 (1989)). Therefore, the substrate specificity of the enzyme EpiD was investigated using mutated precursor peptides, synthetic peptides, and peptide libraries. Synthetic peptide libraries are useful new tools for the identification of optimal peptide ligands, for example the determination of antigenic peptides (Houghten, R. A., et al., *Nature* 354:84–86 (1991); Lam, K. S., et al., *Nature* 354:82–84 (1991)). Even complex peptide libraries can be analyzed by ES-MS (Metzger, J. W., et al., *Anal. Biochem.* 210:261–277 (1994)). The enzymatic reaction products were characterized by tandem mass spectrometry and isoelectric focusing. The protein-peptide interaction between EpiD and EpiA coupled to N-hydroxysuccinimide-activated (NHS-activated) HiTrap was also investigated.

Determination of the Substrate Specificity of EpiD Using Mutant Precursor Peptides and Chemically Synthesized Peptides The precursor peptide EpiAC+22S altered by gene mutation was used to test the production of enols by reaction of peptides with COOH-terminal serine with EpiD. No reaction occurred, indicating the necessity for a COOH-terminal cysteine residue. EpiAS-19A was a substrate for oxidative decarboxylation, giving the first hint that EpiD had no absolute substrate specificity. However, not all peptides with a COOH-terminal cysteine residue were a substrate of EpiD, as demonstrated with the peptide EpiAdesC$^{+22}$ (Table 1).

The leader peptide of the precursor peptide EpiA has no significant influence on the reaction with EpiD (Kupke et al, 1994). For the determination of the minimal size of the substrate, synthetic peptides with increasingly larger deletions of the amino terminus were used (Table 1). Reaction products were identified by their increasing hydrophobicity, increased absorption at 260 nm in 0.1% trifluoroacetic acid/H$_2$O/acetonitrile (FIGS. 19A and 19B), and the mass decrease of 46 Da as compared with the unmodified peptides. Surprisingly, a weak reaction was even observed for the tetrapeptide SYCC. For a further study of the substrate specificity of EpiD, the heptapeptide SFNSYCC (SEQ ID NO: 2) was used. The serine and cysteine residues of the peptide SFNSYCC (SEQ ID NO: 2) form the COOH-terminal bicyclus of mature epidermin, and the possibility could not be excluded that amino acid exchanges in this peptide have an influence on the reaction with EpiD. The various investigated peptides are listed in Table 1; the assays were carried out as described below in Example 12; where the table indicates that no reaction with EpiD occurred, this indicates that using the given assay conditions, no reaction product was detected.

As EpiD does not require the presence of any amino acid sequence, much less a particular amino acid sequence, amino-terminal to the tetrapeptide SYCC (SEQ ID NO: 27) in order to catalyze oxidative decarboxylation of a peptide that has the required carboxy-terminal sequence, it will be understood by those of skill in the art that the process of the invention can be used to effect oxidative decarboxylation of peptides much larger that the 4–7 amino acid residue peptides specified in Tables 1 and 2. These larger peptides may of course be produced via expression in a prokaryotic or eukaryotic host of a DNA sequence engineered to encode the desired amino acid sequence. Engineering of such a DNA fragment is well within the ability of one of ordinary skill in the art. The general methods summarized in Example 10 which were used to effect the expression and purification of peptides can be applied equally well to the production of larger peptides.

In addition, such larger peptides may also be synthesized chemically using the procedures summarized in Example 11 for the chemical synthesis of the heptapeptide SFNSYCC, (SEQ ID NO: 2) as well as by other chemical procedures well known to those of ordinary skill in the art.

Interestingly, the penultimate cysteine residue can be exchanged with at least a serine or threonine residue (FIGS. 19A, 19B, and 20A–D). Modification or exchange of the COOH-terminal cysteine residue resulted in loss of the reaction with EpiD. Confirming the results obtained for the mutant precursor peptides, neither SFNSYCS, (SEQ ID NO: 41) SFNSYCM, (SEQ ID NO: 42) nor SFNSYC (SEQ ID NO: 43) were substrates of EpiD (introduced amino acids are in boldface type). The analog with a COOH-terminal ethyl-thioether structure (SFNSYCC(SEQ ID NO: 2)(Et)), the amide SFNYSCC-NH$_2$, (SEQ ID NO: 2) and the peptide SFNSYC(SEQ ID NO: 43)Hcy (COOH-terminal homocysteine residue) were not substrates of EpiD.

Mersacidin is another lantibiotic containing a COOH-terminal —NH—CH=CH—S— group probably formed by modification of a COOH-terminal cysteine residue (Kogler et al., in *Nisin and Novel Lantibiotics* (Jung, G., and Sahl, H. -G., eds) pp. 159–170, Escom, Sweden (1991)). No information is available on the enzymes involved in modification of the mersacidin precursor peptide. The COOH-terminal peptide TLTSECIC (SEQ ID NO: 44) of the mersacidin precursor peptide was not a substrate of EpiD.

Tandem Mass Spectra of Modified SFNSYTC and SFN-SYSC

Sequence and structure analysis of peptides can be carried out with tandem mass spectrometry (collision-induced dissociation) (Biemann, K., *Methods Enzymol* 183:455–479 (1990)). The reaction products were analyzed using product ion scans and neutral loss scans. A production scan is obtained by setting the first analyzer to transmit ions of a chosen m/z value to the collision cell of the mass spectrometer. The precursor ions are dissociated in the collision cell by collision with argon atoms, and the product ion spectrum is then scanned by the second analyzer. In the constant neutral loss scan, the first and second analyzer are scanned together such that there is a constant mass difference between the ions transmitted by the two analyzers. Under these conditions, only ions that lose a neutral fragment with a mass corresponding to the chosen mass difference will be detected.

In collision-induced dissociation experiments, peptides are preferentially cleaved at the peptide bonds between NH and CO, resulting in so-called amino-terminal B$_n$ fragments and COOH-terminal Y$_n$ fragments (Biemann, K., *Methods Enzymol* 183:455–479 (1990)). To verify that the COOH-terminal cysteine residue of the reaction products is modified, product ion scans of SFNSYTC (SEQ ID NO: 31) and SFNSYSC (SEQ ID NO: 5) and the corresponding reaction products were recorded (FIGS. 20A–D). These peptides were used to exclude intramolecular disulfide bridge formation in the peptide SFNSYCC(SEQ ID NO: 2). The B$_1$–B$_6$ fragments were identical for the peptide and its reaction product, proving that the COOH-terminal amino acid residue was modified. However, SFNSYTC (SEQ ID NO: 31) and SFNSYSC (SEQ ID NO: 5) and their reaction products differed from each other by 14 mass units in their B$_6$ fragments, showing the Ser/Thr exchange. The mass difference between the modified peptide and its B$_6$ fragment was 75 mass units; the mass difference between the unmodified peptide and its B$_6$ fragment was 121 mass units. It was, therefore, possible to identify the reaction products by neutral loss mass spectrometry (see below).

Determination of the Subtrate Specificity of EpiD Using Synthetic Peptide Libraries Tandem mass spectrometry methods have already been used to determine the composition of synthetic multicomponent peptide mixtures. For example, O-tert-butylated by-products of peptide libraries were identified by neutral loss scans (Metzger, J. W., et al., *Anal. Biochem.* 210:261–277 (1994)). However, neutral loss scans have not yet been used to identify the products of an enzymatic reaction in peptide mixtures.

Heptapeptide sublibraries with one variable amino acid residue (wherein the variable amino acid residue can be any one of the 20 common amino acids Ala, Arg, Asn, Asp, Cys, Gln, Glu, Gly, His, Ile, Leu, Lys, Met, Phe, Pro, Ser, Thr, Trp, Tyr, or Val) at positions 1–7 of the peptide substrate S$^1$FNSYCC$^7$(SEQ ID NO: 2) were synthesized and incubated with EpiD. Peptides were identified by their masses using product ion scans and neutral loss scans and by comparison of the mass spectra obtained after various incubation times. The heptapeptides with a single amino acid substitution at positions 1–4 were substrates of EpiD (Table 2). At positions 5–7 of the peptide, not all amino acid residues were possible, so the last three amino acids determined the substrate specificity for EpiD (Table 2). For the libraries SFNSX$^5$CC (SEQ ID NO: 10) (FIGS. 21A and 21B) and SFNSYX$^6$C (SEQ ID NO: 11) (FIGS. 22A and 22B) (wherein X can be any one of the 20 common amino acids noted above), the reaction products were identified by neutral mass loss spectrometry of the peptide mixtures. The tyrosine residue at position 5 can be replaced by the hydrophobic amino acid residues Val, Ile/Leu, Met (the signal from SFNSMCC (SEQ ID NO: 32) –46 Da in the neutral loss scan was weak), Phe and Trp; it is not possible to differentiate between Ile and Leu by ES-MS. The cysteine residue at position 6 can be replaced by Ala, Ser, Val, Ile/Leu (with very low reaction rates), and Thr. Peptides containing amino acids residues with acidic or basic side chains at position 5 or 6 were not substrates of EpiD. In position 7 of the peptide substrates, only cysteine was accepted (Table 2).

The intensity of the signals in the neutral loss scans cannot be used to determine the concentration of the reaction products since it was observed that the degree of fragmentation in collision-induced dissociation experiments depends on the structure of the individual peptide (compare the relative signal intensities obtained in the neutral loss scan of FIGS. 22A and 22B with the relative reaction rates of the peptides SFNSYX$^6$C (SEQ ID NO: 11) with EpiD as determined in FIGS. 23A–23E).

The libraries SFXXYCC, (SEQ ID NO: 20) SXXXYCC, (SEQ ID NO: 21) and XXXXYCC (SEQ ID NO: 22) were also incubated with EpiD, and neutral loss scans for the reaction mixtures were recorded. By comparison of the electrospray mass spectrum of the libraries with the neutral loss scans of the corresponding reaction mixtures, identifying the reaction products, a mass shift to lower masses for the neutral loss scans was observed. The results indicate the positions 1–4 of the peptide S$^1$FNSYCC$^7$ (SEQ ID NO: 2) can be varied to a very large extent. This is in accordance with the result that the tetrapeptide SYCC (SEQ ID NO: 27) is a substrate of EpiD.

Kinetic Studies Using Mass Spectrometry

In order to determine which of the peptide substrates were converted by EpiD at the highest rate, mass spectra of the reaction mixtures were recorded after defined time intervals. The kinetics were determined for the less complex libraries SFNS(F/W/Y)(C/S/T)C, (SEQ ID NO: 12) and SFNSYXC (SEQ ID NO: 11) (FIGS. 23A–23E). Interestingly, the valine and not the serine exchange at position 6 gives reaction rates similar to that observed for the original cysteine residue, whereas SFNSYTC, (SEQ ID NO: 31) for example, was converted by EpiD at a lower rate. From the nine peptides of the library SFNSC(F/W/Y)(C/S/T)C, (SEQ ID NO: 45) SFNSYCC gave the highest catalytic rate (data not shown).

To confirm the results obtained by ES-MS, the catalytic rates were compared by incubating each of the single peptides SFNSYTC (SEQ ID NO: 31) and SFNSYCC (SEQ ID NO: 2) with EpiD and determining the amount of products by UV absorbance (FIGS. 19A and 19B). For determination of $K_m$ values, a more precise assay for oxidative decarboxylation of peptides must be developed.

Determination of the Isoelectric Points of Modified Precursor Peptides

It had been predicted that the reaction of EpiA or EpiAR-1Q with EpiD would lead to the removal of the COOH-terminal carboxyl group (Kupke, T., et al., *J. Biol. Chem.* 269:5653–5659 (1994)). Therefore, the modified peptides should be more basic than the educts. In order to verify this hypothesis, the isoelectric points of the products and the educts were determined. In the immunoblot of the isoelectric focusing gel, several bands were observed in the case of the modified peptides, although purified peptides were used for the experiments, indicating the instability of the reaction products. All of the bands were more basic than the educts, and for determination of the isoelectric points, the most basic bands were used. In the case of EpiAR–1Q –46 Da, the most basic band was the most intense band. The isoelectric points of modified EpiA and EpiAR-1Q were determined to be pH 7.9 (unmodified: pH 6.4) and pH 6.45 (unmodified: pH 5.0), respectively (data not shown), consistent with the theoretical values obtained with the program CHARGPRO (PC/GENE, IntelliGenetics, CA) when the COOH-terminal carboxyl group was "blocked." The theoretical values were pH 7.84 for modified EpiA (unmodified: pH 6.33) and pH 6.33 for modified EpiAR-1Q (unmodified: pH 4.83).

To confirm the results, the migration behaviors of unmodified and modified EpiA were compared in a nondenaturating gel. Modified EpiA migrated more slowly than the unmodified peptide, indicating that it is more positively charged (data not shown).

Interaction between EpiD and EpiA

EpiA or EpiAR- 1Q was coupled to a NHS-activated HiTrap column in order to purify the enzymes involved in epidermin biosynthesis by affinity chromatography. Binding studies were performed with purified EpiD or extracts of induced *E. coli* K38 (pGP1-2, pT7-5epiD) cells. In both cases, the migration of EpiD was retarded only under reducing conditions (FIG. 24). The applied EpiD focused as a sharp yellow band on the EpiA-HiTrap column. Other proteins of the cell extract were not retarded, indicating the specificity of the interaction (data not shown). Even under reducing conditions, the interaction was weak, and EpiD already eluted with the loading buffer containing no salt. In a control experiment, the interaction was investigated using a column without any coupled peptide, and as expected, the migration of EpiD was not retarded.

Determination of the Molecular Mass of EpiD

To remove interfering substances, EpiD was purified by reversed-phase chromatography using the solvents $H_2O$/0.1% trifluoroacetic acid and acetonitrile/0.1% trifluoroacetic acid. Under these acidic conditions, the flavin coenzyme was removed from EpiD.

The mass of the flavin coenzyme was determined to be 455.5 Da (457 Da in a second experiment), closely agreeing with the theoretical value of 456.3 Da, confirming that the flavin component is FMN and not FAD (theoretical mass, 785.6 Da). The average molecular mass of EpiD was determined to be 20,827±5 Da (FIG. 25) (in two further experiments the molecular mass was determined to be 20,830±4 Da, and 20,825±3 Da, respectively), which is in close agreement with the theoretical value of 20,825 Da calculated for the DNA-derived protein sequence (calculated with the computer program MacProMass 1.04), indicating that EpiD was not covalently modified. The possibility of intramolecular disulfide bridge formation between the four cysteine residues of EpiD cannot be ruled out.

The first elucidated modification reaction of lantibiotic precursor peptides was the oxidative decarboxylation of EpiA catalyzed by EpiD (Kupke, T., et al., *J. Biol. Chem.* 269:5653–5659 (1994)). Since EpiD modifies a COOH-terminal amino acid, the investigation of substrate specificity is simplified. For the determination of the substrate specificity of EpiD, single peptides and peptide libraries were used (Tables 1 and 2). From the data presented, one can conclude that EpiD reacts with most of the peptides containing the following sequence motif at the carboxyl terminus: (V/I/L/(M)/F/Y/W)-(A/S/V/T/C/(I/L))-C. For the sublibrary SFNS(F/Y/W)(C/S/T)C, (SEQ ID NO: 12) it was demonstrated that simultaneous exchange of two amino acid residues at positions 5 and 6 was possible. The results demonstrated that the functional groups of the amino acid residues tyrosine (—OH) and the penultimate cysteine (—SH), were not essential for substrate binding to EpiD. Furthermore, no aromatic ring system in position –3 is required, since Tyr can be exchanged for other non-aromatic, hydrophobic amino acid residues. For the penultimate position, the size of the introduced amino acid residue is of importance since the cysteine residue can be replaced with the hydrophilic residues serine or threonine or with the hydrophobic residue valine (with Ile/Leu only very low reaction rates were observed) but not with glycine or phenylalanine.

One of the most interesting questions is whether unmodified EpiA or EpiA with a COOH-terminal meso-lanthionine ring structure is the natural substrate of EpiD. The result that SFNSYCC(Et) (SEQ ID NO: 2) was not a substrate of EpiD and the above-mentioned recognition motif provides evidence that EpiD does not react with a COOH-terminal meso-lanthionine structure. Since only the COOH-terminal tripeptide determines the substrate specificity, precursor peptides with dehydrated residues at positions +3, +8, +14, +16, and +19 should also react with EpiD. Oxidative decarboxylation and dehydration of the precursor peptide may occur simultaneously, followed by thioether formation. In vivo instability of the oxidative decarboxylated precursor peptide is not a problem if dehydration and lanthionine formation take place with high reaction rates. High reaction rates are facilitated by organization of the modifying enzymes EpiB, EpiC, and EpiD in a multienzyme complex (substrate channeling).

The free thiol group and the negatively ionized carboxyl group of the COOH-terminal cysteine residue may be involved in binding of the substrate to EpiD since the amide SFNSYCC-$NH_2$ (SEQ ID NO: 2) and the thioether SFNSYCC(Et) were not substrates of EpiD. Interestingly, even homocysteine in the COOH-terminal position of the peptide was not a substrate of EpiD, indicating the necessity for a —$CH_2$—SH side chain. In all cases, no products were observed that were only oxidized and not decarboxylated.

The modification of the last cysteine residue was shown by tandem mass spectrometry and by the investigation of the substrate specificity. Since all substrates of EpiD with different side chains in positions 1–6 of the heptapeptide SFNSYCC (SEQ ID NO: 2) react to form products with the same mass difference of 46 Da, the modification must be in the last cysteine residue.

The substrate specificity of EpiD provides valuable information on the topology of the peptide binding site. In the future, the structure of EpiD and EpiD-peptide complexes can be determined using stable isotope labeling and multi-dimensional NMR methods (Withrich, K., *Science* 243:45–50 (1989); Markley and Kaninosho, "NMR of Macromolecules", (1993) pp. 101–152) to gain more insight into this novel enzyme catalysis. In a second approach, the FMN-binding site and the substrate binding site of EpiD will be investigated by site-directed mutagenesis. Of special interest is changing the residues of the peptide binding site of EpiD by mutation of the gene in order to change the substrate specificity of EpiD. The altered substrate specificity should be easily detected by using peptide libraries and neutral loss mass spectrometry and by determining the turnover rate of the various substrates.

Since EpiD has no absolute substrate specificity, its enzymatic function can be used to modify peptides, thus potentially altering the biological activities of these altered peptides. Knowledge of the substrate specificity of EpiD can also be used to construct epidermin with an altered COOH terminus by oligonucleotide-directed mutagenesis of the structural gene.

Reaction products of EpiD comprising the structure given in FIG. 27 (which contains an enethiol moiety) can be used as precursors for further chemical syntheses.

In future experiments, the mechanism of the oxidative decarboxylation will be analyzed; however, there are several problems left to be solved. It is unknown whether decarboxylation is catalyzed by EpiD or whether it is a spontaneous reaction. The oxidized intermediate peptide may be chemically modified to prevent decarboxylation. Determination of how the reduced coenzyme $FMNH_2$ is reoxidized in vivo will also be investigated. The structure of the reaction product has to be determined by NMR studies.

The method of the invention, which provides for the oxidative decarboxylation of a peptide, can be carried out in vitro under the following conditions, although it will be clear to those of ordinary skill in the art that the parameters given herein for carrying out the enzymatic reaction may be varied. The enzymatic reaction can be carried out at a temperature of 37° C. in 20 mMTris/HCl buffer (pH 8.0) containing 3 mM dithiothreitol, 1–2 μg of EpiD (the concentration of which is determined according to the method of Bradford, *Anal. Biochem.* 72:248–254 (1976)), and 10–50 μg of peptide, in a total volume of 1 ml. The enzymatic reaction is carried out for between 0.5 and 1 h.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

Example 1

1. Overproduction of gallidermin

A DNA fragment containing the open reading frame of gallidermin can be cloned in *Staphylococcus epidermidis* DSM 3095, the epidermin producing strain by using a medium copy plasmid such as pC194, pE194, pUB110, pT181 or pMK148 gallidermin. An increase of the gene doses usually correlates with an increase of product production; the correlation is not necessarily linear. High copy number plasmid derivatives of pC194 or pT181 can be used as cloning vehicles too.

2. Exchange of leader sequence

The leader-sequence of epidermin corresponding to amino acids −1 to −30, is involved in the secretion of epidermin. The sequence can be used to secrete other peptides in *S. epidermidis* such as gallidermin.

The leader-sequence DNA can be made portable by inserting respective linkers at the beginning and at the end of its sequence. Thus the leader sequence DNA can be isolated in large amounts from the plasmid and can be inserted at respective positions of other peptides and proteins. The leader-sequence DNA can also be produced by chemical synthesis.

Example 2

Production of Gallidermin using *S. epidermis* as host

Figure 6:
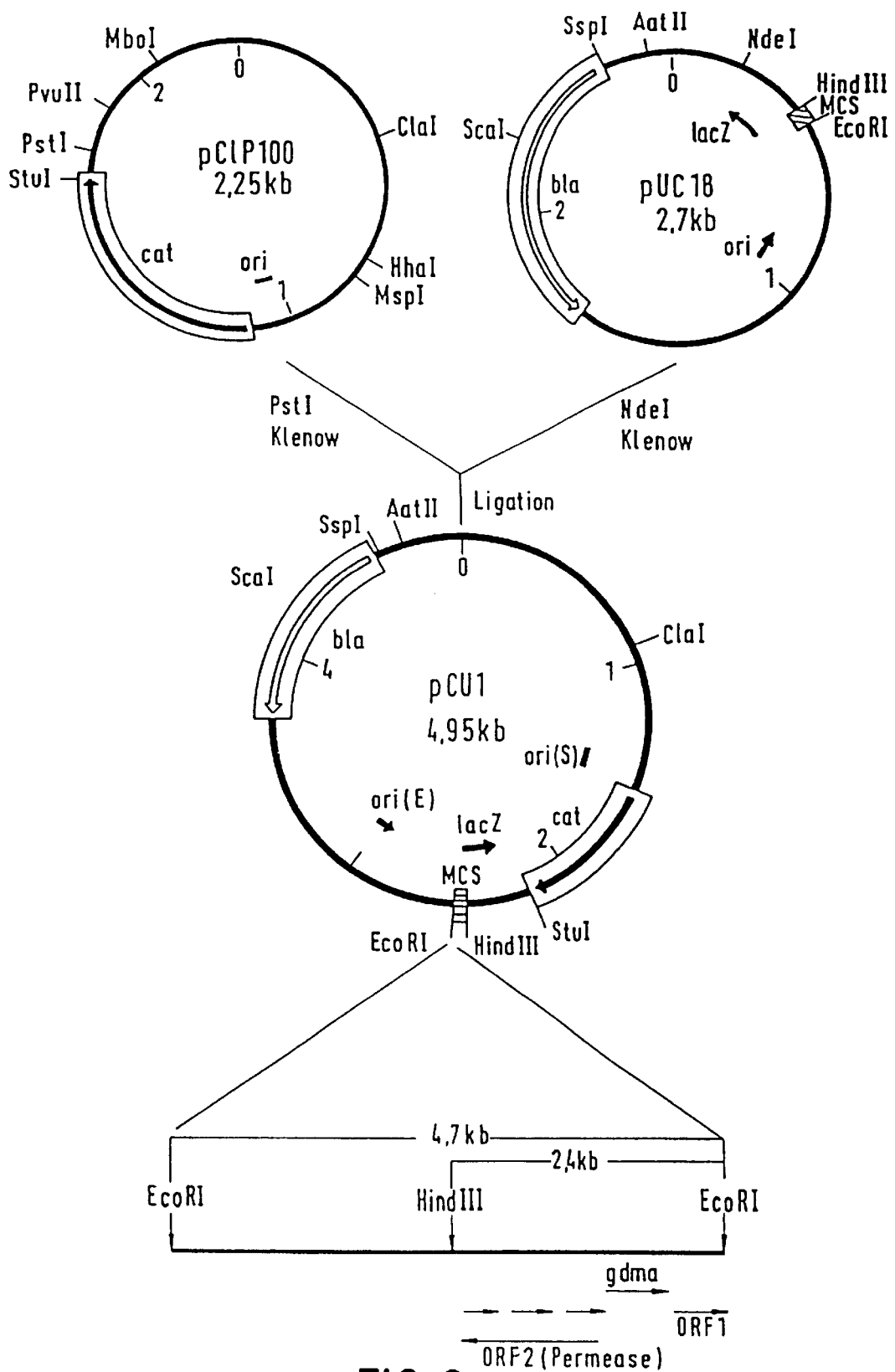
FIG. 6 depicts a schematic representation of the process for preparation of the pCUI plasmid from pCLP100 plasmid and pUC18 plasmid.

1. Preparation of plasmid (see FIG. 6)

a) Plasmid pCUI was prepared by ligating Pst1 digested pCLP100 and Ndel digested pUC18 using Klenow as described in the thesis "Molekular genetische Untersuchungen zur plasmidkodierten Arsenit und Arsenatrestistent bei Staphylococcen", by Dr. Ralf Rosenstein (available from the Technische Universitat, Munich, West Germany). The resulting plasmid was then digested with EcoRI.

b) Chromosomal DNA was isolated from *S. gallinarum* (DMS 4616) and was digested with EcoRI. A 4.7 kb fragment containing the gallidermin structural gene in a 2.4 kb long sequence between HindIII and EcoRI restriction sites was isolated using as a primer the sequence.

5' CAC ATC CAG GAG TAC 3' (SEQ ID NO: 46)

c) The 4.7 kb Fragment was then ligated into the EcoRI site of the digested pCUI plasmid from step a) to give a plasmid designated pCUgdml.

2. Preparation of a S. epidermis host

In this example a mutant strain of S. epidermis DSM 3095 incapable of producing epidermin was isolated.

The mutagenesis was carried out on a strain which was characterized by chromosomally coded Rifampicin resistance (20 ug/ml).

S. epidermis DSM 3095 grown on Agar plates was used to inoculate 30 ml basic broth medium which was cultivated overnight. 0.5 ml of the overnight cultivation was then used to inoculate 50 ml of production medium which was shake cultivated at 37° C. for three hours.

Cells were removed from the cultivation medium and suspended in 4.5 ml pre-warmed TM-Buffer (30 mM Tris-Maleate pH 6.5 (the resulting solution is designated Solution A)).

The solution A was checked for spontaneous mutations and for cell count ($1.25 \times 10^{10}$ cells/ml).

4 ml of solution A was thoroughly shaken with 1 ml ethyl methyl sulphonate (final concentration 47 $\mu$g/ml) and then maintained under shaking at 37° C. for one hour.

Cells were then extracted from the cultivation broth, washed twice in TM-Buffer and resuspended in 5 ml TM-Buffer (the resulting solution was designated Solution B and contained mutated cells).

Solution B was found to contain $2 \times 10^8$ cells/ml which corresponds to survival rate of 1.6%.

50 ml of solution B was added to 5 ml production medium and grown overnight at 37° C. (phenotypic expression). The resulting solution was designated Solution C. A cell count showed $7.3 \times 10^8$ cells/ml.

The solution was plated on BM-Agar plates and individual colonies were picked out. These were used to inoculate test plates (consisting of BM-Agar to which *Micrococcus luteus* has been laid on the surface). Those colonies which had no inhibitory effect on *M. luteus* were selected as non-producers of Epidermin.

BM Agar contains per liter:

10 gm Peptone No. 140

5 gm Yeast extract 1 mg Glucose 5 mg NaCl 1 mg $K_2HPO_4$ pH 7.5

A mutation rate of about 3% was noted.

The 45 non-producers which were found were sub-cloned 20 times to yield 16 stable non-producers.

All stable non-producers were found to contain the wild type plasmid pEpi32. From the restriction pattern this is identified as identical to the plasmid in the wild type strain.

Transformation of non-producing S. epidermis 750 ml of BM-medium was inoculated with 5 ml of medium obtained by overnight cultivation of a stable non-producing strain, and the inoculated medium was shake cultivated in a 2 liter flask at 37° C. with a shake speed of 120 rpm.

The initial optical density of the inoculated BM-medium was 0.03–0.04. When the optical density had reached 0.45–0.55 the cells were removed by centrifugation in a GS.-3-Rotor at 8500 rpm for 15 minutes at 4° C. The isolated cells were then washed successively in 750, 350, 40 and 10 ml of 10% glycerin, suspended in 2–3 ml 10% glycerin, and frozen in 110 ml portions in ERGs at −70° C. The cell count amounted to $1-5 \times 10^{10}$/ml.

The frozen cells were thawed at room temperature for 5 minutes, then 50 $\mu$l of cell suspension was incubated in an ERG with 2 $\mu$l plasmid pCUgdml in TE-Buffer for 30 minutes at room temperature.

The mixture was then introduced into an electroporation cuvette having a 0.2 cm electrode gap and immediately electroporated. Thereafter the cells were rapidly resuspended in 950 $\mu$l SMMP50-medium, transferred into a 2.5 ml ERG and shaken for 90 minutes at 37° C. The ERGs were inclined at 45° in order to provide for a good aeration of the medium.

SMMP50-medium contains pro 100 ml, 55 ml 2SMM, 40 ml 4 PAB and 5 mol 5% BSA. The 2SMM contains 1 mol saccharose, 0.04 mol maleic acid, 0.04 mol $MgCl_2$ and NaOH to pH 6.5. 4 PAB is a solution of 7 g/100 ml of Gibco antibiotic medium 3.

The cell suspension is diluted and spread on a BM-Agar containing gallidermin which is incubated for 20 hours at 37° C.

Testing of growing strains which produce gallidermin was carried out by selection of colonies from a *M. luteus* test plate and by cultivating the respective selected colonies and determining the presence of gallidermin by HPLC.

Three pCUgdml transformed mutants capable of producing gallidermin were located.

Determination of the presence of gallidermin produced by pCUgdml transformed S. epidermin a) Bio assay FP-Agar was inoculated with *M. luteus* ATCC 9341 and incubated at 37° C. for 18 hours. Half of the produced culture was removed with a loop and suspended in 100 ml FP-medium and was cultivated for 8 hours at 36° C. The cultivation was stopped when the optical density reached 1.0. FP-Agar was inoculated with 0.5% of this suspension, each 10 ml was poured into a Petri dish and stored for 3 weeks at 4° C.

The Plate diffusion test was carried out as described in Zähner and Maas, "Biology of Antibiotics", Springer Verlag, Berlin 1972. 10 ul of culture filtrate from cultivation of the transformed S. epidermin was captured on a filter paper and dried. The paper was placed on the test plate which was then incubated for 24 hours at 37° C.

b) HPLC

The selected transformed strain was cultivated for 26 hours in the production medium. The culture broth was centrifuged for 10 minutes at 13.000 rpm.

The isolated culture liquid was then subject to HPLC on a SP 8.700 liquid chromatography apparatus (Spectra Physics, Darmstadt, FRG) using as the mobile phase A) $H_2O$ with 0.5% 70% perchloric acid and B) Acetonitrile. Column packings were Nucleosil −100 C-18 of grain size 7 um and column sizes 125 mm×4.6 mm I.D. and 20 mm×4.6 mm ID for the pre-column.

Gradients were as follows:

| time (min.) | A [%] | B [%] |
|---|---|---|
| 0 | 77.5 | 22.5 |
| 8 | 63.0 | 37.0 |
| 8.5 | 0 | 100 |
| 9.5 | 0 | 100 |
| 10 | 77.5 | 22.5 |
| 14 | 77.5 | 22.5 |

Figure 7A:
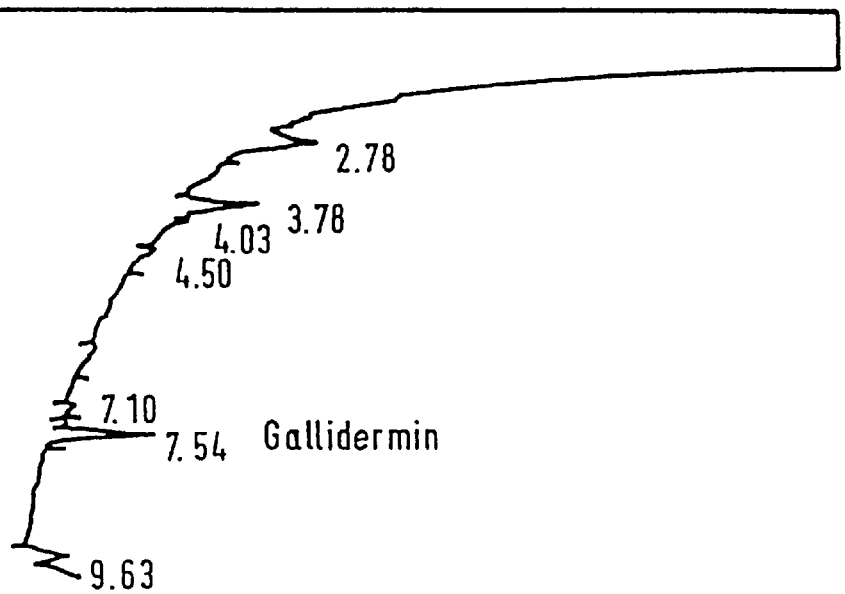
FIG. 7A depicts the elution pattern of the isolated culture medium prepared in Example 2.
Figure 7B:
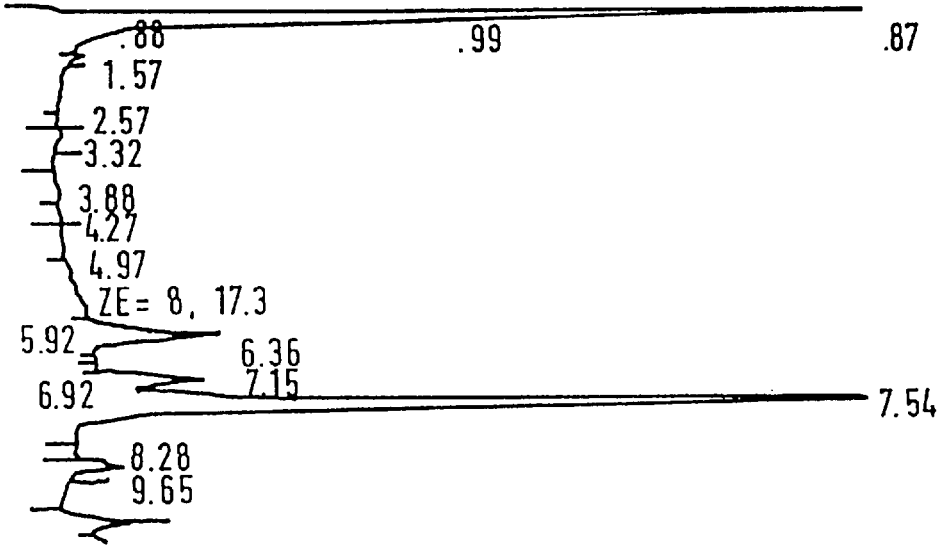
FIG. 7B depicts the elution pattern of a standard containing gallidermin. Gallidermin is eluted at 7.54 minutes.

The resulting chromatogram is shown in FIG. 7A. A standard curve is shown in FIG. 7B showing that gallidermin elutes at 7.54 minutes.

The following were used as culture medium.

| 1. FP-Agar | | |
|---|---|---|
| Meat extract | 4 g | |
| Peptone | 10 g | |
| NaCl | 3 g | |
| Na$_2$HPO$_4$ | 5 g | |
| Glucose | 10 g | |
| Complex agar | 15 g | |
| Water | 1 liter | |
| pH | 7.2 | |
| 2. FP-Medium | | |
| Meat extract | 4 g | |
| Peptone | 10 g | |
| NaCl | 3 g | |
| Na$_2$HPO$_4$ | 5 g | |
| Glucose | 10 g | |
| Water | 1 liter | |
| pH | 7.2 | |
| 3. Production medium | | |
| Meat extract | 33 g | |
| Malt extract | 30 g | |
| NaCl | 40 g | |
| Calcium Hydroxide | 3.8 g | |
| Water | 1 liter | |
| pH | 6.5 | |

Example 3

Plasmid Isolation

Plasmid DNA from *S. epidermis* Tü3298 was isolated according to a modified procedure of Norick et al., *Ann. NY-Acad. Sci.* 182:279–294 (1971). *S. epidermis* was grown on BM-media (1% peptone 140, Gibco, Neu-Isenburg, F.R.G., 0.5% yeast extract, Difco, Detroit, U.S.A., 0.1% glucose, 0.5% NaCl and 0.1% K$_2$HPO$_4$×2H$_2$O) until stationary phase. Cells were centrifuged and washed twice with 0.5 M EDTA. The pellet was resuspended in 80 ml NaCl buffer (50 mM Tris/HCl, pH 7, 50 mM EDTA, 2.5 M NaCl), 1.5 ml lysostaphin solution (0.5 mg/ml, Sigma, Heidelberg, F.R.G.) was added and the suspension was incubated at 37° C. for 20 min. Cells were lysed by the addition of 80 ml lysis buffer (50 mM Tris/HCl, pH 8, 300 mM EDTA, 500 mM Brij., 40 mM sodium deoxycholate and kept on ice for 1 h. The lysate was centrifuged (30 min, 13,000 rpm, 4° C.) and the supernatant was mixed with one quarter of its volume with 50% solution of PEG-6000. Plasmid DNA was precipitated at 4° C. overnight. The DNA suspension was centrifuged (20 min, 13,000 rpm, 4° C.), resuspended in 8 ml TE buffer and 50 μl of proteinase K solution (20 mg/ml) was added. After incubation at 37° C. for 15 min the DNA was precipitated with ethanol and further purified by CsCl centrifugation (1 g CsCl/ml, 40,000 rpm, 40 h, 20° C.).

RNA isolation and electrophoreses

*S. epidermin* was grown on SMS minimum medium (Terzaghi et al., *Appl. Microbiol.* 29:807–813 (1975)) and RNA isolated therefrom, using a modified procedure similar to that described for *Bacillus subtilis* RNA (Ulmanen et al., *J. Bacteriol.* 162:176–182 (1985)). Cells were lysed with lysostaphin (0.1 mg/ml) in protoplasting buffer and incubation was performed at 37° C. Total RNA was glyoxylated (McMaster et al, *Proc. Natl. Acad. Sci. USA* 74:4835–4839 (1977)) and separated on a 1.2% agarose gel using 10 mM Na$_2$PO$_4$, pH 7, as electrophoresis buffer. RNA was stained with ethidium bromide and blotted to a nitrocellulose membrane (Scheider and Schuell, Dassel, F.R.G.) by capillary transfer with 20×SSC buffer (0.15 M NaCl, 0.015 M tri sodium citrate, pH 9). 23SrRNA and 16SrRNA were used as size standards.

In vitro transcription

Single stranded RNA probes were obtained by cloning the respective fragment in a pSPT18/19 vector system (Boehringer Mannheim, Mannheim, F.R.G.). The plasmids were linearized with EcoRI or HindIII to get a linear DNA template. For transcription the protocol in Melton et al, *Nucl Acid Res.* 12:7035–7056 (1984), was modified according to the instructions of the commercial supplier. T7-RNA polymerase or SP6-RNA polymerase was used in the presence of α$^{32}$P-CTP (800 Ci/mMol). Unincorporated ribonucleotides were separated from labeled RNA by Sephadex G50 chromatography.

Northern hybridization

RNA was transferred after electrophoresis according to Thomas, P. S., *Proc. Natl. Acad. Sci. USA* 77: 5201–5205 (1980). After 2 h incubation at 80° C. the filter was shortly incubated in 20 Tris/HCl, pH 8, at 100° C. to reverse glyoxylation. Afterwards filters were prehybridized at 42° C. in 50% formamide, 5×SSC (0.15 M NaCl, 0.015 M tri sodium citrate, pH 9), 50 NaPO$_4$, pH 6.5, 0.1% ficoll 400 (Pharmazia, Freiburg, F.R.G.), 0.1% polyvinylpyrollidone, 0.1% bovine serum albumin and 0.25 mg/ml denatured salmon sperm DNA for 2 h. After probe addition hybridization was performed in the same buffer at 42° C. for 12 h. Filters were washed once in 1×SSC, 0.1% SDS at 42° C. for 15 min and exposed to Kodak-X Omat films at −70° C. for 4 h. Thereafter filters were washed twice with 0.5×SSC, 0.1% SDS at 70° C. for 15 min and autoradiograms were exposed at −70° C. for 16 h. Next day washing was continued with 0.1×SSC, 0.1% SDS at 70° C. for 30–60 min and afterwards again exposed to Kodak-X Omat films at −70° C. for 3 days.

Southern hybridization

For southern hybridization (Southern, E. M., *J. Mol. Biol.* 98:503–517 (1975)) 5' labeled oligonucleotides used as probes at 23° C. Oligonucleotides were labeled with gamma$^{32}$P-ATP using 4T polynucleotide kinase (Boehringer Mannheim, Mannheim, F.R.G.). Oligonucleotides and primers were synthesized on a 391 DNA synthesizer (Applied Biosystems, Weiterstadt, F.R.G.) and used without further purification.

DNA sequencing

DNA was sequenced radioactively and non-radioactively by the chain termination method (Sanger et al., *Proc. Natl. Acad. Sci. USA* 74:5463–5467 (1977)) using T7-DNA polymerase (Pharmazia, Freiburg, F.R.G.). Radioactive plasmid sequencing was performed as described in Hattori et al, *Anal. Biochem.* 152:232–238 (1984) with appropriate primers. The 3.6 kb BamHI/PstI fragment was sequenced non-radioactively on an Applied 373A DNA sequenator (Applied Biosystems, Weiterstadt, F.R.G.). The respective fragment was cloned in phagemid pBSK∓. The construction was digested with BamHI and SacI and the linearized DNA was unibidirectionally digested from the 5' end with exonuclease III (Boehringer Mannheim, Mannheim, F.R.G.) to obtain a set of nested deletions which were treated with mung bean nuclease (Boehringer Mannheim, Mannheim, F.R.G.) to receive blunt ends. After electrophoresis (1% agarose gel) fragments of appropriate size were isolated from the gel, religated and transformed into *E. coli* strain XL-1 Blue. Single stranded DNA was isolated by using helper phage CSM13 and sequenced with Taq Polymerase (Promega, Freiburg, F.R.G.) according to the protocol of the commercial supplier.

Plasmid Construction

The staphylococcal tetracycline resistance plasmid pT181 has been sequenced (Kahn et al, *Plasmid* 10:251–259

(1983)) and found to contain a single NdeI site within the pre-gene which is not necessary for plasmid replication (Gennaro et al, *J. Bacteriol.* 169:2601–2610 (1987)). The multiple cloning site (mcs) of the *E. coli* vector pUC19 (Yanisch-Perron et al., *Gene* 33:103–119 (1985)) was inserted into the NdeI site to form pT181mcs (see FIG. 14).

A staphylococcus-*E. coli* shuttle vector, pCUI (FIG. 10) was constructed from ppCLP100, a derivative of the staphylococcal chloramphenicol resistance plasmid pC194 (Horinouchi et al., *J. Bacteriol.* 150:815–825 (1982)) and the *E. coli* vector pUC19. PCUI is stably maintained in both hosts with an insert size up to approximately 6 kb. pT181mcs and pCUI are compatible in staphylococci and were used to subclone DNA fragments from pTü32.

Figure 8A:
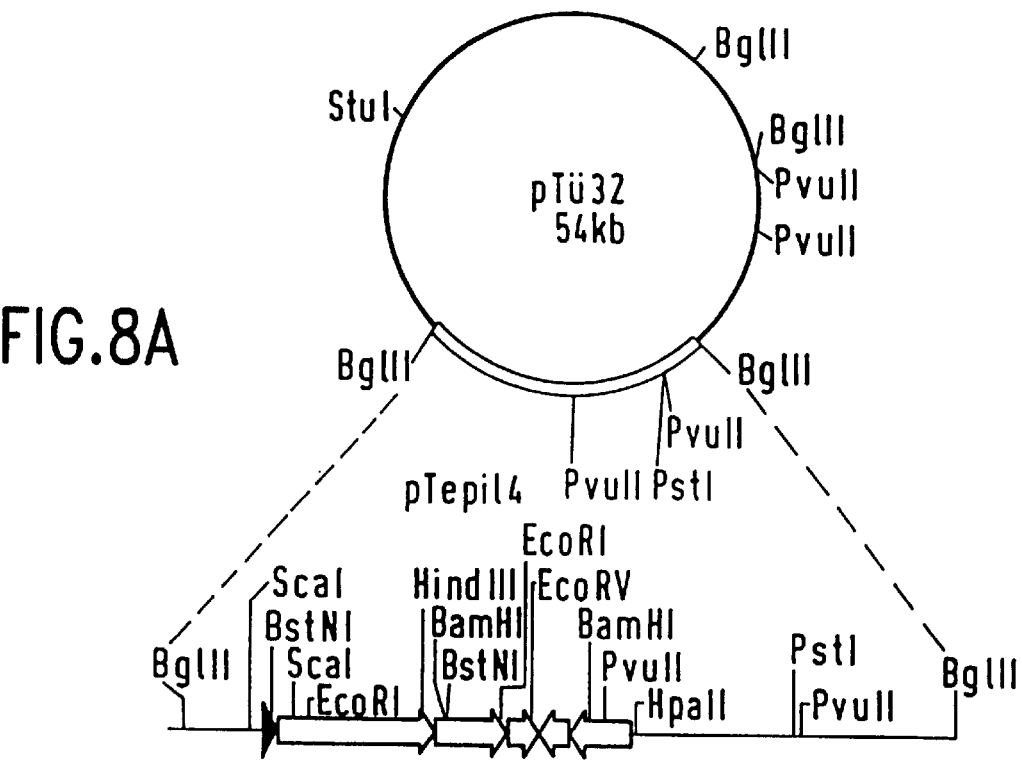
FIG. 8 is a genetic analysis of episome pTü32 of *S. epidermis* plasmid pTü32, including 8A: a restriction map of episome pTü32, and 8B: a restriction map of the 13.5 kb BglII fragment of pTü32. The filled arrow corresponds to the epiA structural gene. Open arrows represent reading frames epiB, C, D, P and Q.
Figure 8B:
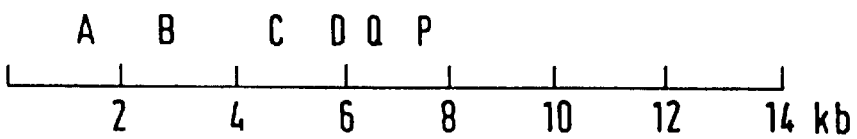
Figure 8C:
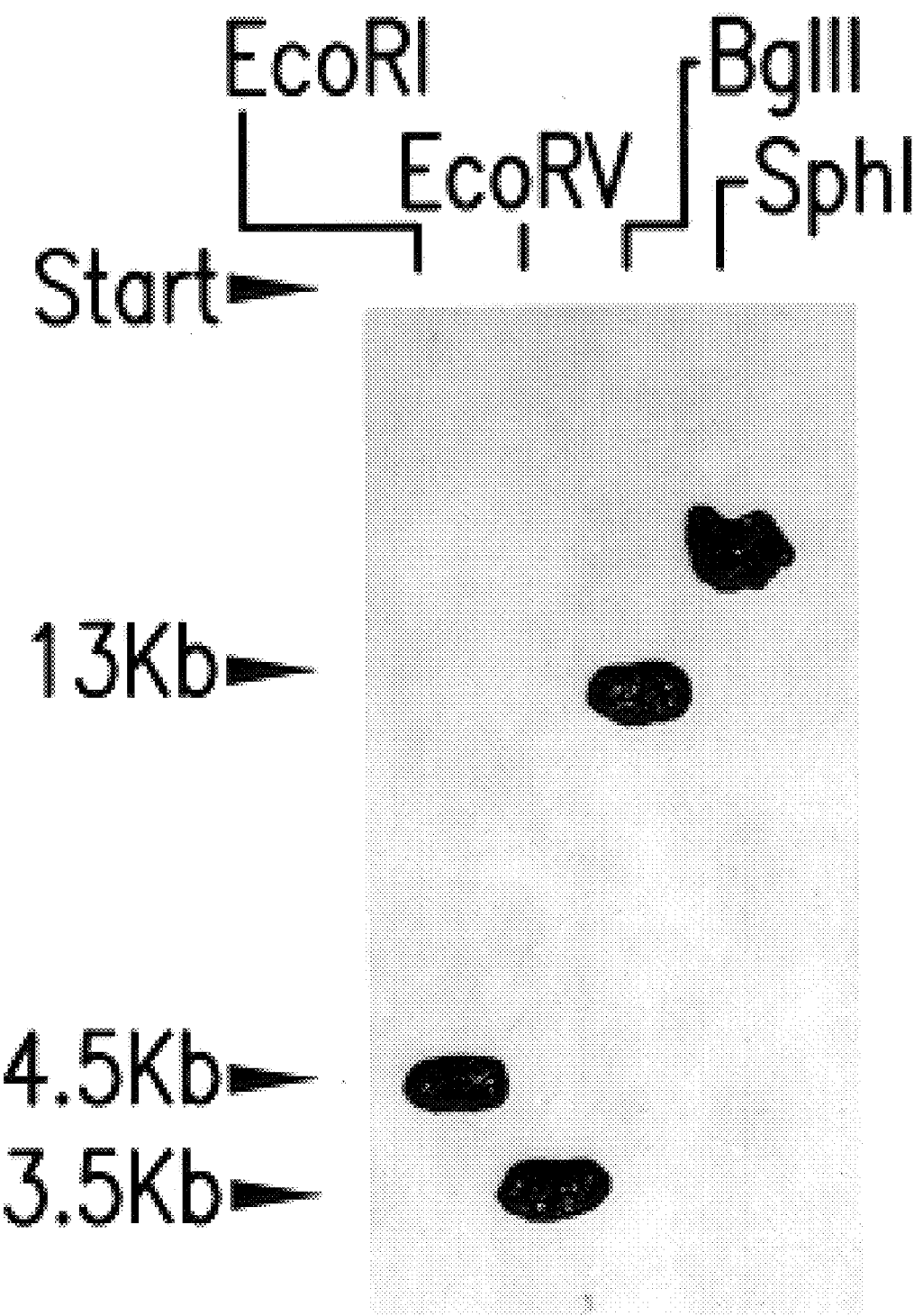

A HindIII fragment of pTü32 was cloned in pUC19 and used as a probe in Southern hybridization to identify further restriction sites near the HindIII fragment (FIG. 8C).

The 13.5 kbp BglII fragment of the 54 kbp episomal element pTü32 from *S. epidermis* was subcloned in pT181mcs to yield pTepi14 (FIG. 8A). For DNA sequencing subclones were made in the *E. coli* vector pUC19(Yanisch-Perron et al., *Gene* 33:103–119 (1985)) and pBluescript II$^R$ (Stratagene, Heidelberg, F.R.G). Single stranded RNA probes were obtained from DNA cloned in vector pSPT18/19 (Boehringer Mannheim, Mannheim, F.R.G.).

Gene Analysis

Sequencing the DNA region adjacent to the epidermin structural gene, epi A, revealed five additional complete open reading frames epi B, C, D, P and Q inside the 13.5 kbp BglII fragment of pTü32.

As can be seen in FIG. 9, directly adjacent to the sequence encoding for EpiA separated by only 50 nucleotides from the epiA ochre codon there is a large open reading frame preceded by a S/D sequence which spans 2,970 bp. A TTG codon for leucine which can also act as a translation start codon in staphylococci is in appropriate distance (86 p) to a S/D sequence. This open reading frame is designated epiB and as described herein can successfully be used for the complementation of epidermin biosynthesis mutants and an essential role in epidermin biosynthesis.

The protein coded for by epiB, starting from the TTG (Leu) has a molecular weight of about 115kDa, a net charge of −3 at pH 7, and is moderately hydrophobic (41% hydrophobic residues) as may also be predicted from a hydrophilicity plot according to Kyte et al.,*J. Mol. Biol.* 157:105–132 (1982).

At the 3' end of epiB no palindromine structure characteristic of transcription termination can be seen. There is, however, a 122 bp overlap with an other reading frame epiC, shifted by −1 base pair also to be seen in FIG. 9.

Independently cloning and sequencing the respective 47 kbp HindIII-fragment twice from two independent plasmid isolations has established that this result is not an artifact. This was also confirmed by mutant complementation with an epiC containing fragment as described herein.

Inside the overlapping region of epiB and epiC reading frames the first TTG codon (Leu) which is only 36 bp 3' to an AGGA element serves as a translational start codon, indicating that both reading frames overlap by about 40 codons. The actual amino-terminus of the EpiC protein was determined by N-terminal sequencing. Reading frame epiC encodes a protein with 445 amino acid residues commencing with starting codon TTG (Leu). The reading frame EpiD directly follows 3' to epiC with a start ATG 86 p 3' to a AGGAGG S/D sequence. 3' to EpiD is a classical rho dependent transcription terminator structure; EpiD encodes a protein of 181 amino acid residues with ATG (Met) on start codon.

None of the proteins EpiB, C, D, P and Q show any similarity with protein sequences filed in the protein data bases Swiss Prot and Gene Bank, and thus represent unknown types of enzymes and regulatory proteins.

Transcription of the biosynthetic genes

Single stranded RNA probes were obtained by cloning the desired fragment in a pSPT 18/19 vector system (Boehringer Mannheim, Mannheim, F.R.G.) as described above.

Two transcripts differing considerably in size were obtained as illustrated in FIG. 10. A hybridization probe specific of epiA identified a small transcript of about 300 bp. Transcripts of similar size were also found for the lantibiotics nisin (Buchmann et al., *J. Biol. Chem.* 263:16260–16266 (1988)) and subtilin (Banerjee et al, *J. Biol. Chem.* 263:9508–9514 (1988)). Additionally a large transcript of approximately 5 kb can be identified with a hybridization probe specific for epiB. As there were no *E. coli*-like promoter sequences in front of epiB, whereas appropriate sequences were located 5' to epiA it can be seen that the epiA promoter acts as a promoter for a polycistronic mRNA.

Downstream open reading frames

The open reading frames epiP and epiQ are located on the opposite DNA to epiB, C and D with epiQ sharing a termination structure with EpiD a perfect hairpin with a 6 bp loop.

Exactly within this loop structure the TAA stop codons for both reading frames EpiD and epiQ share two of three nucleotides.

The epiP reading frame starts with an ATG codon which is in appropriate distance (6 bp) to a S/D sequence. Taking the ATG codon as the translational start of epiP a protein of 461 amino acid residues with molecular weight of 51.8 kD. epiP shares characteristic homologies with the conserved amino acid motives of serine proteases (see FIG. 11) indicating that epiP is implicated in cleaving the natured lantibiotic from the modified prepeptide.

The epiQ reading frame also starts with an ATG codon and encodes 205 amino acid residues (FIG. 9). A S/D sequence is present 6 bp distance to the ATG codon and a molecular weight of 243 kD can be deduced from the DNA sequence. The epiQ protein shares characteristic homologies with PhoB (see FIG. 12) which is a positive regulatory factor for the phosphate regulatory of *E. coli* so that epiQ is implicated as a regulatory factor in lantibiotic synthesis.

Preceding epiP is an *E. coli*-like-10 region (5'-TATAAA) 12 bp in front of the S/D sequence which may serve as a promoter in staphylococci. The distance between the epiP stop codon and the ATG start codon of epiQ is only 10 nucleotides and the epiQ S/D sequence overlaps with the epiP termination codon as shown in FIG. 9.

5'to epiA, B, C, D a further reading frame with opposite orientation can be seen which potentially encodes a maximum of 148 amino acids. A characteristic S/D sequence is present but none of the previously described start codons for staphylococci (ATG, TTG, GTG). With a −1 frame shift a further reading frame follows which exceeds the isolated BglII fragment illustrated in FIG. 9.

These two reading frames are homologous to a single open reading frame, gdmY, identified adjacent to the structural gene of gallidermin (Schnell, N., *Biosynthese der Peptid-Antibiotika Epidermin und Gallidermin*; Doctoral Thesis, University of Tubingen, F.R.G. (1989)). The homologous reading frames on the *S. epidermis* plasmid are designated epiY' and epiY".

Example 4

*S. carnosus* TM300 was transformed with the plasmid pTepi14, prepared as described above, using standard techniques. The transformed strain was then grown on BM-media (see above).

The resulting transformants were found to be capable of inhibiting the epidermin sensitive tester strain *Micrococcus luteus* ATCC9341. In this assay 1 ml of an overnight culture of *M. luteus* (adjusted to an $OD_{578}$ of 1.0) was added to 500 ml molten BM-Agar. Petri dishes usually contained 10 ml of this agar. Dilutions of *S. epidermis* cultures were spread on the agar surface. Epidermin positive colonies were detected as a zero of growth inhibition of *M. luteus* around the colonies.

Cells were grown on 3% meat extract, 3.8% malt extract, 0.6% $CaCl_2 \times 2H_2O$ and 4.6% NaCl, pH 6.5. According to the transformation used, tetracycline or chloramphenicol was added. After 24 h incubation (37° C., 160 rpm) in 500 ml Erlenmeyer flasks with one extension containing 100 ml medium, the culture both was centrifuged at 10,000 rpm in a Servall centrifuge for 10 min.

Supernatants of liquid transformant cultures were purified by adsorption chromatography (XAD1180, impurities eluted with water/methanol (1:1) and epidermin eluted with methanol/0.1N HCl (9:1); after evaporation the eluate was adjusted with 3N NaOH to pH 3.5 and filled up with water to 10 ml) and detected by HPLC chromatography. The inhibitory activity co-migrated with mature epidermin at 6.75/6.76 min (see FIGS. 13A and 13B). Untransformed *S. carnosus* culture media treated similarly had no peak in this elution region (6.72 to 6.79 min, FIG. 13C). These results clearly confirmed the heterologous epidermin biosynthesis in *S. carnosus* and demonstrated that pTepi14 contains all information necessary for epidermin biosynthesis.

As pTepi14 contains the 13.5 kbp BglII fragment this indicates that the epiY' and epiY" reading frames are not necessary for the production of epidermin in this system as epiY' lacks a translational start codon and epiY" is incomplete on this fragment.

Example 5

A number of epi⁻mutants of *S. epidermin* Tü3298 were prepared by ethylmethane sulfonate (EMS) mutagenesis. This procedure was carried out according to Miller, J. H., *Experiments in molecular genetics*, Cold Spring Harbor Laboratory; Cold Spring Harbor, N.Y. (1972). The mutants were screened for epidermin production, or lack of epidermin production using the *M. luteus* assay described above. Epi-mutants were transferred several times to test their stability. Of the 40 epi⁻mutants isolated, only 10 were stable; the unstable mutants produced epidermin again after several transfers. All stable epi⁻mutants still contained plasmid pTü32 which suffered no deletions or rearrangements as tested by restriction endonuclease analysis. The 10 epi⁻mutants were used for complementation studies.

Various restriction fragments of plasmid pTü32 were cloned in *S. carnosus* to test for heterologous epidermin production. The fragments were inserted into plasmid vectors T181mcs and pCU1 as described above and the various ORFs which were subcloned as shown in FIG. 16B.

Cloning was first carried out in *S. carnosus* (by protoplast transformation (Gotz et a., *FEMS Microbiol. Lett.* 40:285–288 (1987)) or *E. coli* (using $CaCl_2$; Cohen et al., *Proc. Nat. Acad. Sci. USA* 69:2110–2114 (1972)) and then the recombinant plasmids were isolated and transferred into the various *S. epidermis* epi mutants by electroporation (Augustin et al., *FEMS Microbiol. Lett.* 66:203–208 (1990)). Enzymes used for molecular cloning were obtained from Boehringer Mannheim (Mannheim, F.R.G.), BRL (Eggenstein, F.R.G.) or Pharmacia (Sweden). This indirect transformation method was necessary since transformation of *S. epidermin* strains was only successful with circular covalently closed (ccc) plasmids; when ligation products were used, transformants could only be isolated occasionally.

The results of the complementation studies are summarized in Table 3.

Figure 16A:
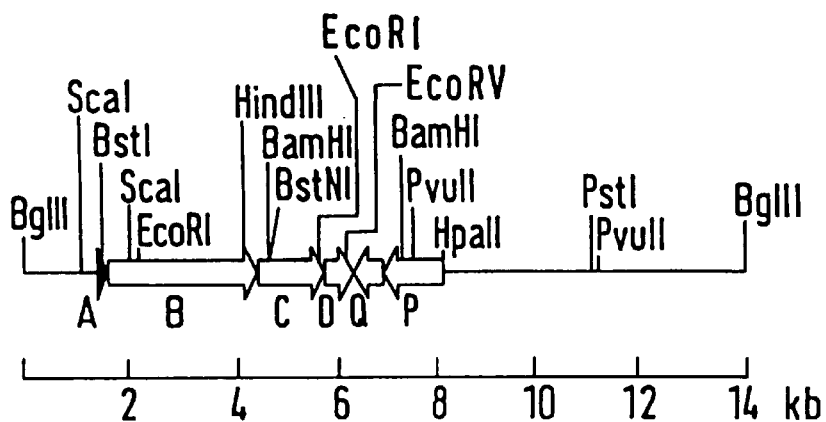
Figure 16B:
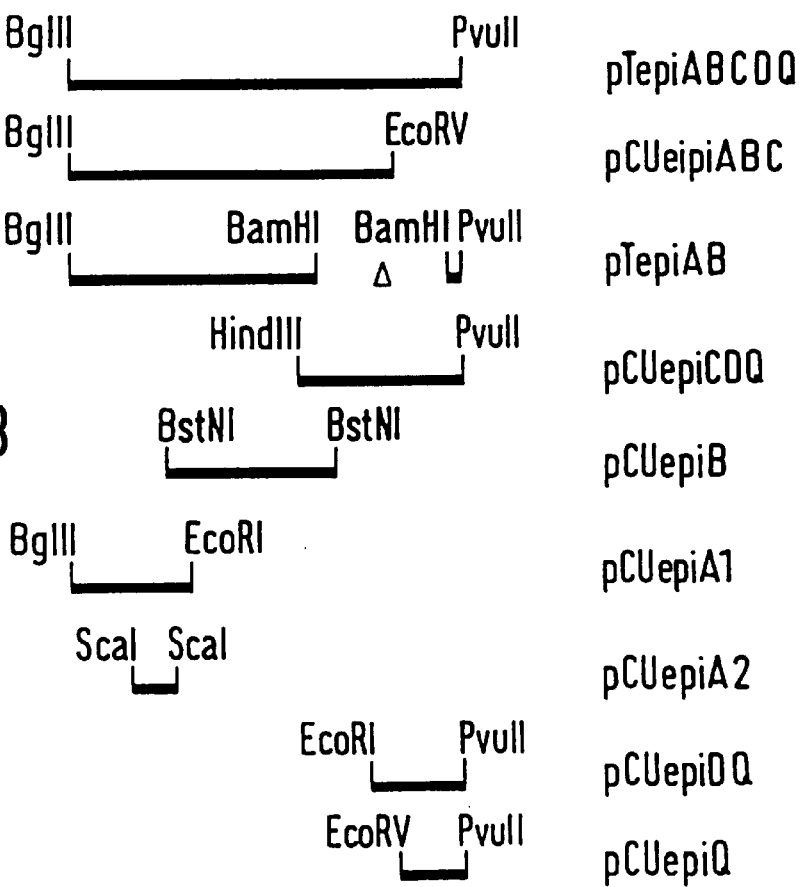

A series of plasmids were constructed which carry various epi genes (A, B, C, D, P and Q) (FIG. 16B). Two plasmids pTepi14 and pTepiABCDQ were able to complement all epi⁻mutants. The other constructed plasmids pCUepiABC, pTepiAB, pCUepiCDQ, pCUepiB, pCUepiA₁, pCUepiA₂, pCUepiDQ and pCUepiQ contained the indicated genes.

The various plasmids were able to complement only certain classes of mutants which are classified herein as follows:

EMS 5 and 6—epiA mutants,
EMS 18, 33 and 45—epiB mutants,
EMS 12, 13, 19 and 39—epiC mutants,
EMS 11—EpiD mutant.

The results as shown below indicate at least that the four ORFs epiA, B, C and D are required for epidermin biosynthesis.

The plasmid pCUepiA₁ carries the structural gene epiA as the only complete ORF and an additional 1400 bp upstream and 602 bp downstream, the latter encoding 190 amino acids of the epiB N-terminus. Transformation using pCUepiA₁ resulted in the complementation of the epidermin mutants EMS 5 and 6 identifying them as epiA mutants. The smaller epiA-containing ScaI fragment cloned in both orientations in pCUepiA₂ failed to complement the epi⁻mutants as the epiA promoter was cut by this enzyme.

pCUepiB carries a BstN1 fragment containing the complete epiB and an upstream region of 100 bp which includes 75 bp of the 3' terminus of epiA; the epiA promoter is missing. Transformation with pCUepiB failed to complement any *S. epidermis* mutant to epidermin production, indicating that epiB lacks its own promoter and is very likely co-transcribed from the epiA promoter.

This is in agreement with the results obtained with pTepiAB (FIG. 16B; Table 3) which contains epiA promoter and the complete epiA and B genes and the use of which complements both the epiA and epiB mutants.

Plasmid pCUepiCDQ was able to complement both epiC and EpiD mutants and plasmid pCUepiDQ was only able to complement the EpiD mutant (Table 3). The complementation was independent of the orientation of the cloned DNA fragment. These results show that both epiC and EpiD possess their own promoters.

Example 6

The epiA mutated pTü32 derivatives were isolated from EMS 5 and 6 and the respective epiA ORFs were sequenced. Both plasmids had point mutations within epiA; in the EMS 5 plasmid the codon AGT (Ser³) was changed to AAT (Asn³) and in the EMS 6 plasmid the codon GGA (Gly¹⁰) was changed to GAA (Gln¹⁰); both these mutations were located at crucial sites within the unmodified epidermin.

Example 7

An epiB (on a BstN1-fragment) was put under the control of the promoter on plasmid pPS4 (FIG. 17). The resulting plasmid pPS4epiB was able to complement the epiB mutants EMS 18, 33 and 45. A plasmid containing epiB in the opposite orientation did not complement the mutations. This also establishes that pCUepiB was unable to complement any of the EMS mutants, because the epiA promoter is missing.

Example 8

As described above, the presence of pTepi4 (FIG. 16A) resulted in epidermin biosynthesis in S. carnosus; however, the presence of pTepiABCDq did not. The minimum size of DNA required which leads to heterologous epidermin expression in S. carnosus was determined by complementing S. carnosus (pTepiABCDQ) with distally located DNA fragments (FIG. 18). Transformation of S. carnosus (pTepiABCDQ) with plasmids pCA44-90, pCA44-91 and pCA44-92 led to epidermin production, pCA44-92 containing the complete epiQ and epiP ORFs consisted of the smallest DNA fragment able to complement epidermin production. These results indicate that the epidermin biosynthetic genes are clustered within an 8 kb DNA fragment containing the six ORFs; epiA, B, C, D, Q and P and that no other genes are involved in epidermin biosynthesis.

In these examples staphylococcal plasmid DNA was prepared by the cleaved lysate method (Makino et al., *J. Mol. Biol.* 190:37–44 (1986)). Cells were lysed by the addition of lysostaphin (8 μg/ml) and the DNA was isolated by CsCl-centrifugation. *E. coli* supercoiled plasmid DNA was prepared by the modified alkaline lysis method (Birnboim et al., *Nucl. Acid Res.* 7:1513–1518 (1979)).

The DNA sequence of the PCR-amplified epiA-containing fragment and the two mutated epiA regions of the *S. epidermis* mutants, EMS 5 and 6, was determined by double-stranded DNA sequencing using the dideoxy procedure (McMaster et al., *Proc. Natl. Acad. Sci. USA* 74:4835–4839 (1977)), the "sequence" list of Pharmacia and (α-$^{35}$S)-dATP from Amersham. Primers used for DNA sequencing and PCR amplification were synthesized using the DNA-synthesizer of Applied Biosystems. The sequences of the two primers for PCR amplification of epiA are as follows:

a) 5'-GGGTTTTAGG(TA)ATCCTTTTTAATAAATTTTTAGGAG-3' (SEQ ID NO:47)

b) 5'-CCTCAAAATTAAGACG(A)GAT(G)CCTCTATTGAAGCCC-3' (SEQ ID NO:48)

Primer a) binds in front of the RBS of epiA and primer b) after the epiA stop codon. These bases indicated by bold letters represent (shown in brackets) used to create BamHI sites in front and at the end of epiA; the epiA promoter is absent in the amplified DNA fragment.

For determination of the DNA sequence of the mutated epiA in the mutants EMS 5 and 6, plasmid pTü32 was isolated and the DNA region was amplified by PCR using another set of DNA primers binding upstream of the postulated epiA promoter region (5'-GGTTTGGTTATTTTCC-3') (SEQ ID NO: 49) and downstream of the stop codon (5'-CCTCAAAATTAAGACAGAGCCTC-3'); (SEQ ID NO: 50) the DNA sequence of epiA is also shown in Schnell et al., *Nature* (Lond.) 333:276–278 (1988).

Example 9

The epi D gene was isolated from the plasmid pTepi14, multiplied by PCR amplification and cloned into the StuI-restriction site of vector pIH902 (New England, Biolabs) by "blunt end" ligation, with the result that the epi D gene is fused without any intervening base pairs immediately at the Factor Xa cleavage site of vector pIH902, which was then transformed into *E. coli*.

Cultivation of the *E. coli* resulted in expression of the enzyme Epi D fused to the Maltose binding protein of *E. coli*. The resulting fusion protein was purified by affinity chromatography on Amylose column material.

It was found that the enzyme EpiD could be cleaved from the fusion protein in low yield by means of Factor Xa. A modification of the amino acid sequence at the cleavage region will enable the cleavage rate to be improved.

The fusion protein was sequenced at the DNA level from the fusion position to the 3' end of EpiD. The EpiD sequence corresponded to the wild type sequence of *S. epidermis*.

The following examples were disclosed in Kupke et al., *J. Biol. Chem.* 270(19):11282–11289 (1995), the contents of which are fully incorporated by reference herein.

Example 10

*Expression and Purification of Precursor Peptides Containing Alterations at the Carboxyl Terminus*—The mutated precursor peptides were expressed as malE fusions as described for EpiA and EpiD (Kupke, T., et al., *FEMS Lett.* 112:43–48 (1993); Kupke, T. et al., *J. Bacteriol.* 174:5354–5361 (1992)). The epiA gene (Schnell, N., et al., *Nature* 333:276–278 (1988)) was amplified by polymerase chain reaction and inserted into the polylinker StuI site of the vector pIH902 (a derivative of the vector pIH821 (Riggs, P. D., "Current Protocols in Molecular Biology", John Wiley & Sons Inc., New York (Struhl et al. eds., 1990, pps. 16.6.1–16.6.12)). Using the 5'-primer (5'-d(ATGGAAGCAGTAAAAG)-3'), (SEQ ID NO: 51) the epiA start codon ATG (Met) was ligated directly to the last codon AGG (Arg) of the factor Xa cleavage sequence of the pIH902 polylinker. The following 3'-primers were used for the construction of the mutant precursor peptides EpiAC+22S, EpiAdesC$^{+22}$, and EpiAS+19A; (i) 5'-d(CTGAATTA ACTACAATAACTGTTAAAACTACC)-3' (SEQ ID NO: 52) exchanging the COOH-terminal cysteine Cys$^{+22}$ residue for serine, (ii) 5'-d(CTGAATTA TCAACAATAACTGTTAAAAC)-3', (SEQ ID NO: 53) deleting the COOH-terminal cysteine residue, and (iii) 5'd (CTGAATTAACAACAATAAGCGTTAAAACTACC)-3', (SEQ ID NO:54) exchanging the residue Ser$^{+19}$ for Ala$^{+19}$. The sequences of the mutated epiA genes were verified by DNA sequencing using appropriate primers.

The precursor peptide altered by mutation of the gene were purified as described previously for EpiA (Kupke, T., et al., *FEMS Lett.* 112:43–48 (1993)). The masses of the purified peptides were verified using ES-MS.

Example 11

*Chemical Synthesis of Peptides and Peptide Libraries*— Single peptides and peptide libraries were synthesized by solid-phase peptide synthesis on preloaded Wang (40 mg/0.6 mmol/g) or 2-chlorotritylchloride resin (40 mg/0.58 mmol/g) using Fmoc/tBU (fluorenylmethoxycarbonyl/tert-butyl) strategy on a SYRO multiple peptide synthesizer. DIC/HOB$_t$ (diisopropylcarbodiimide/1-hydroxybenzotriazole) activation and deprotection times of 13 and 25 min, respectively, were used. For single peptides and fixed positions in the libraries, we used a 10-fold excess of amino acids and a coupling time of 60 or 90 min, respectively. For the variable positions in the libraries, we used an equimolar mixture of all 20 amino acids. Two couplings were made with 120 min for each variable position. The first coupling was performed with an equimolar amount of the amino acid mixture and the second with a 3- or 5-fold excess. Cleavage from the resin and deprotection was achieved by treatment with trifluoroacetic acid/phenol/thioanisol/ethanedithiol/water (82.5:5:5:2.5:5) for 2 h. The peptides were precipitated using diisopropyl ether. The purity was checked by reversed phase chromotagraphy and ES-MS. In the single substitution libraries, all of the expected peptides were present with relative amounts between 0.4 and 1.0, as concluded from the signal intensity of the peptides in ES-MS (Metzger, J. W., et al., Anal Biochem. 210:261–277 (1994)). Multiple peptide synthesis methods and their applications are reviewed in Jung and Beck-Sickinger (Jung, G. & Beck-Sickinger, A. G., Angew. Chem. Int. Ed. Engl. 81:367–388 (1992)). The synthesized peptides are listed in Tables 1 and 2.

Example 12

*Purification of EpiD and Enzyme Assay*—EpiD was purified as described previously using *E. coli* expression plasmid pT7-5apiD (Kupke, T. et al, *J. Bacteriol.* 174:5354–5361 (1992)). The concentration of the EpiD solution was determined according to Bradford (Bradford, M. M., *Anal. Biochem.* 72:248–254 (1976)); the concentrations of the precursor peptide solutions were estimated by the absorbance at 205 nm using an extinction coefficient of 31 for a protein solution of 1 mg/ml (Janson, J. C., & Ryden, L., *Methods Enzymol.* 193:441–455 (1990)); the synthetic peptic substrates were weighed out. The enzyme was assayed for 0.5–1 h at 37° C. in 20 mM Tris/HCl buffer (pH 8.0) containing 3 mM dithiothreitol, 1–2 µg of EpiD, and 10–25 µg of precursor peptide or 50 µg of synthetic peptide in a total volume of 1 ml. The reaction mixture was then separated by reversed phase chromatography using a µRPC C2/C18 SC 2.1/10 column (Pharmacia Biotech Inc.). Peptides were eluted with a linear gradient of 0–50% acetonitrile, 0.1% trifluoroacetic acid in 3.8 ml with a flow rate of 200 µl/min. The absorbance was measured simultaneously at 214, 260, and 280 nm. The peptides were collected by the peak fractionation method, dried with a vacuum concentrator, stored at −70° C., dissolved in 30% acetonitrile, and analyzed by ES-MS.

Peptide libraries were dissolved to a concentration of 1–2 mg/ml in 20 mM Tris/HCl buffer (pH 8.0) containing 3 mM dithiothreitol. The peptide mixture (250 µl) was then incubated with 2–3 µg of EpiD at 20° C. Using flow injection (carrier flow 100 µl/min., methanol/water (1:1) (v/v)) 5 µl of the reaction mixture was applied with an autosampler (Gilson Abimed, model 231) to ES-MS (see below) at defined time intervals. Neutral loss scans were recorded after 3 h of incubation.

Example 13

*Electrospray and Tandem Mass Spectrometry*—Electrospray mass spectra (Bruins, A. P., et al., *Anal. Chem.* 59:2642–2646 (1987); Covey, T. R., et al., *Rapid Commun. Mass Spectrom.* 2:249–256 (1988)) were recorded on a triple quadrupole mass spectrometer API III with a mass range of m/z 10–2400 equipped with a nebulizer-assisted electrospray ("ion spray") source (Sciex, Thornbill, Ontario, Canada). The mass spectrometer was operated in a positive ion mode under conditions of unit mass resolution (80% valley definition) for all determinations. Mass spectra were obtained by acquiring data points every 0.5 Da with a dwell time of 0.5 or 1 ms. The potential of the spray needle was held at +4.8 kV; orifice voltages were between +80 and +140 V. For mass calibration, a solution of CsI (0.5 mg CsI in 0.5 ml methanol/water (1:4) (v/v)) was used. Peptide solutions were either continuously infused with a medical infusion pump (model 22, Harvard Apparatus, South Natik, Mass.) at a flow rate of 5 µl/min. or flow-injected with an autosampler.

The tandem mass spectrometer consisted of an arrangement of three consecutive quadrupole systems in which the second one served as the collision region (Yost, R. A. & Boyd, R. K., *Methods Enzymol.* 193:154–200 (1990)). Tandem mass spectrometry (collision-induced dissociation (Hayes, R. N., & Gross, M. L., *Methods Enzymol.* 193:237–268 (1990)) was performed with argon as collision gas and collision energies ranging from 30 to 60 eV.

Example 14

*Determination of the Isoelectric Point of the Reaction Products*—The purified peptides EpiA and EpiAR-1Q, and the corresponding reaction products 3 (oxidative decarboxylated peptides) (Kupke, T., et al., *J. Biol. Chem.* 269:5653–5659 (1994)) were dissolved in water, and 10 µg of each peptide was applied to a Servalyt PreNet 3–10 gel (Serva, Heidelberg, FRG). The peptide mixture Serva No. 39211 was used as an isoelectric focusing standard. Isoelectric focusing was carried out according to the instruction manual of Serva. The focused peptides were blotted on nitrocellulose and detected with an anti-MBP-EpiA antiserum (Kupke, T., et al., *FEMS Lett.* 112:43–48 (1993)) using the ECL system (Amersham Corp.).

Example 15

*Coupling of EpiA to NHS-Activated HiTrap*—Approximately 2 mg of EpiA or EpiAR-1Q was dissolved in 1 ml of coupling buffer (0.2 M $NaHCO_3$, 0.5 M NaCl, pH 8.3) and was coupled to 1 ml of N-hydroxy-succinimide activated Sepharose High Performance column (HiTrap column) according to the instruction manual of Pharmacia. As a control, for the third column, the coupling procedure was carried out with coupling buffer containing no peptide. Binding studies were performed with 20 mM Tris/HCl buffer (pH 8.0) containing 5 mM dithiothreitol. The binding of EpiD to the EpiA-HiTrap column was followed by measurement of the absorbance at 450 nm and by Western blot analysis using the anti-MBP-EpiD antiserum (Kupke, T. et al, *J. Bacteriol.* 174:5354–5361 (1992)).

From the foregoing description, one skilled in the art can easily ascertain the essential characteristics of this invention, and without departing from the spirit and scope thereof, can make various changes and modifications of the invention to adapt it to various usages and conditions.

TABLE 1

Determination of the substrate specificity of the flavoprotein EpiD
(single peptide determinations)

| Peptide | Reaction with EpiD |
|---|---|
| EpiA, EpiAR-1Q, K-EpiA | + |
| EpiAS + 19A | + |
| EpiAC + 22S | − |
| EpiA*des*C$^{+22}$ | − |
| Proepidermin | + |
| Synthetic proepidermin | + |

TABLE 1-continued

Determination of the substrate specificity of the flavoprotein EpiD (single peptide determinations)

| Peptide | Reaction with EpiD |
|---|---|
| AKTGSFNSYCC (SEQ ID NO:55) | + |
| SFNSYCC (SEQ ID NO:2) | + |
| FNSYCC (SEQ ID NO:56) | + |
| NSYCC (SEQ ID NO:57) | + |
| SYCC (SEQ ID NO:27) | + |
| YCC | − |
| AFNSYCC (SEQ ID NO:58) | + |
| SANSYCC (SEQ ID NO:59) | + |
| SFASYCC (SEQ ID NO:60) | + |
| SFNAYCC (SEQ ID NO:61) | + |
| SFNSACC (SEQ ID NO:62) | − |
| SFNSYGC (SEQ ID NO:34) | − |
| SFNSYCS (SEQ ID NO:41) | − |
| SFNSYC (SEQ ID NO:43) | − |
| SFNSYCC—NH$_2$(SEQ ID NO:2) | − |
| SFNSYCC(Et) (SEQ ID NO:2) | − |
| SFNSYCHCy (SEQ ID NO:69) | − |
| SFNSYCM (SEQ ID NO:42) | − |
| SFNSYSC (SEQ ID NO:5) | + |
| SFNSYTC (SEQ ID NO:31) | + |
| SFNSFCC (SEQ ID NO:3) | + |
| SFNSWCC (SEQ ID NO:4) | + |
| SFNYYCC (SEQ ID NO:63) | + |
| SYNSYCC (SEQ ID NO:64) | + |
| SWNSYCC (SEQ ID NO:65) | + |
| TLTSECIC (COOH terminus of mersacidin) (SEQ ID NO:44) | − |

TABLE 2

Determination of the substrate specificity of the flavoprotein EpiD (peptide libraries)

| Peptide libraries | Reaction with EpiD |
|---|---|
| XFNSYCC[a] (SEQ ID NO:6) | + |
| SXNSYCC (SEQ ID NO:7) | + |
| SFXSYCC (SEQ ID NO:8) | + |
| SFNXYCC (SEQ ID NO:9) | + |
| SFNSXCC (SEQ ID NO:10) | |
| SFNSVCC[b] (SEQ ID NO:33) | + |
| SFNSI/LCC[b] (SEQ ID NO:9) | + |
| SFNSFCC (SEQ ID NO:3) | + |
| SFNSYCC (SEQ ID NO:2) | + |
| SFNSWCC (SEQ ID NO:4) | + |
| SFNSYXC (SEQ ID NO:11) | |
| SFNSYAC[b] (SEQ ID NO:67) | + |
| SFNSYSC (SEQ ID NO:5) | + |
| SFNSYVC[b] (SEQ ID NO:35) | + |
| SFNSYTC (SEQ ID NO:31) | + |
| SFNSYCC (SEQ ID NO:2) | + |
| SFNSYI/LC[c] (SEQ ID NO:11) | (+) |
| SFNSYCX (SEQ ID NO:69) | |
| SFNSYCC (SEQ ID NO:2) | + |
| SFNS(F/W/Y)(C/S/T)C (SEQ ID NO:12) | + |

[a]X represents any one of the 20 amino acid residues commonly found in proteins.
[b]These peptides were identified recording neutral loss scans and daughter ion scans of the reaction mixture.
[c]SFNSYI/LC—46 Da is present in very low amounts in the reaction mixture and only detectable by neutral loss mass spectrometry.

TABLE 3

Epidermin production by non-producing *S. epidermidis* mutants after transformation with various pTepi14DNA fragments

| Mutant | pTepi 14 | pTepi ABCDQ | pCUepi ABC | pTepi AB | pCUepi A1 | pCUepi A2 | pCUepi CDQ | pCUepi DQ | pCUepi Q | pCUepi B | Mutation locus |
|---|---|---|---|---|---|---|---|---|---|---|---|
| EMS 5 | + | + | + | + | + | − | − | − | − | − | epiA |
| EMS 6 | + | + | + | + | + | − | − | − | − | − | epiA |
| EMS 11 | + | + | − | − | − | − | + | + | − | − | epiD |
| EMS 12 | + | + | + | − | − | − | + | − | − | − | epiC |
| EMS 13 | + | + | + | − | − | − | + | − | − | − | epiC |
| EMS 18 | + | + | + | + | − | − | − | − | − | − | epiB |
| EMS 19 | + | + | + | − | − | − | + | − | − | − | epiC |
| EMS 33 | + | + | + | + | − | − | − | − | − | − | epiB |
| EMS 39 | + | + | + | − | − | − | + | − | − | − | epiC |
| EMS 45 | + | + | + | + | − | − | − | − | − | − | epiB | pCU: Fragments cloned in pCU1; pT: Fragments cloned in pT181mcs
+ complementation (epidermin production; − no complementation)

What is claimed is:

1. A method of oxidatively decarboxylating a peptide, comprising combining a peptide with EpiD, (SEQ ID NO: 24) said peptide comprising at its carboxy terminus the amino acid sequence $X_1X_2X_3X_4X_5X_6C$ (SEQ ID NO: 1), wherein $X_1$, $X_2$, $X_3$ and $X_4$ are any one of the twenty common amino acids, $X_5$ is Tyr, Val, Met, Phe, Ile, Leu or Trp, and $X_6$ is Cys, Ala, Ser, Val, or Thr, with the proviso that the carboxy terminus of said peptide is not SFNSYCC (SEQ ID NO: 2), SFNSFCC (SEQ ID NO: 3), SFNSWCC (SEQ ID NO: 4) or SFNSYSC (SEQ ID NO: 5), whereby the oxidative decarboxylation of said peptide occurs.

2. The method of claim 1, wherein the carboxy terminus of said peptide comprises an amino acid sequence selected from the group consisting of $X_1$FNSYCC (SEQ ID NO: 6); $SX_2$NSYCC (SEQ ID NO: 7); $SFX_3$SYCC (SEQ ID NO: 8); $SFNX_4$YCC (SEQ ID NO: 9); $SFNSX_5$CC (SEQ ID NO: 10); $SFNSYX_6$C (SEQ ID NO: 11); $SFNSX_5X_6$C (SEQ ID NO: 12); $SFX_3X_4$YCC (SEQ ID NO: 20); $SX_2X_3X_4$YCC (SEQ ID NO: 21); and $X_1X_2X_3X_4$YCC (SEQ ID NO: 22).

3. The method of claim 2, wherein the carboxy terminus of said peptide comprises the amino acid sequence $SFNSX_5X_6$C (SEQ ID NO: 12), wherein $X_5$ is Tyr, Val, Met, Phe, Ile, Leu, or Trp, and $X_6$ is Cys, Ala, Ser, Val, or Thr.

4. The method of claim 2, wherein the carboxy terminus of said peptide comprises the amino acid sequence $SFNSX_5$CC (SEQ ID NO: 10), wherein $X_5$ is Ile, Leu, Val or Met.

5. The method of claim 2, wherein the carboxy terminus of said peptide comprises the amino acid sequence $SFNSYX_6$C (SEQ ID NO: 11), wherein $X_6$ is Ala, Val, or Thr.

6. A method of oxidatively decarboxylating a peptide, comprising combining a peptide with EpiD, said peptide comprising at its carboxy terminus the amino acid sequence SYCC (SEQ ID NO: 27), whereby the decarboxylation of said peptide occurs, with the proviso that the amino acid sequence immediately amino terminal to SYCC (SEQ ID NO: 27) is not SFN.

7. The method of claim 1, wherein said oxidative decarboxylation occurs in vitro in the presence of a substance capable of reducing disulphide bridges.

8. The method of claim 7, wherein said substance is selected from the group consisting of dithiothreitol, β-mercaptoethanol, and glutathione.

9. The method of claim 7 wherein said substance is dithiothreitol.

10. The method of claim 1, wherein said oxidative decarboxylation occurs in a bacterial host expressing
(a) a recombinant DNA molecule encoding said peptide; and
(b) a recombinant DNA molecule encoding the protein EpiD having the amino acid sequence set forth in FIG. 9 (SEQ ID NO: 24).

11. A bacterial host cell expressing
(a) a recombinant DNA molecule encoding a peptide capable of being oxidatively decarboxylated by EpiD, with the proviso that said DNA molecule not encode a peptide comprising at its carboxy terminus the amino acid sequence SFNSYCC (SEQ ID NO: 2), SFNSFCC (SEQ ID NO: 3), SFNSWCC (SEQ ID NO: 4) or SFNSYSC (SEQ ID NO: 5); and
(b) a recombinant DNA molecule encoding the protein EpiD having the amino acid sequence set forth in FIG. 9 (SEQ ID NO: 24).

12. A method of oxidatively decarboxylating a peptide, comprising combining a peptide with a fusion protein comprising EpiD, said peptide comprising at its carboxy terminus the amino acid sequence $X_1X_2X_3X_4X_5X_6$C (SEQ ID NO: 1), wherein $X_1$, $X_2$, $X_3$ and $X_4$ are any one of the twenty common amino acids, $X_5$ is Tyr, Val, Met, Phe, Ile, Leu or Trp, and $X_6$ is Cys, Ala, Ser, Val, or Thr, with the proviso that the carboxy terminus of said peptide is not SFNSYCC (SEO ID NO: 2), SFNSFCC (SEO ID NO: 3), SFNSWCC (SEQ ID NO: 4) or SFNSYSC (SEO ID NO: 5), whereby the oxidative decarboxylation of said peptide occurs.

13. The method of claim 12, wherein said fusion protein is Maltose Binding Protein—EpiD.

* * * * *